(12) United States Patent
Hashimoto et al.

(10) Patent No.: US 8,367,708 B2
(45) Date of Patent: Feb. 5, 2013

(54) PHENYL-ISOXAZOL-3-OL DERIVATIVE

(75) Inventors: Noriaki Hashimoto, Koga (JP); Yasuhiro Sasaki, Naha (JP); Chisato Nakama, Tokyo (JP); Makoto Ishikawa, Tsukuba (JP)

(73) Assignee: MSD K.K., Tokyo (JP)

( * ) Notice: Subject to any disclaimer, the term of this patent is extended or adjusted under 35 U.S.C. 154(b) by 609 days.

(21) Appl. No.: 12/516,025

(22) PCT Filed: Nov. 29, 2007

(86) PCT No.: PCT/JP2007/073099
§ 371 (c)(1),
(2), (4) Date: May 22, 2009

(87) PCT Pub. No.: WO2008/066131
PCT Pub. Date: Jun. 5, 2008

(65) Prior Publication Data
US 2010/0130559 A1    May 27, 2010

(30) Foreign Application Priority Data
Dec. 1, 2006    (JP) ................. 2006-325220

(51) Int. Cl.
*A01N 43/76* (2006.01)
*A01N 43/64* (2006.01)
*A01N 43/18* (2006.01)
*A01N 43/06* (2006.01)
*A01N 43/16* (2006.01)
*A01N 43/08* (2006.01)
*A61K 31/42* (2006.01)
*A61K 31/41* (2006.01)
*A61K 31/54* (2006.01)
*A61K 31/38* (2006.01)
*A61K 31/35* (2006.01)
*A61K 31/34* (2006.01)

(52) U.S. Cl. ............ 514/374; 514/359; 514/222.2; 514/432; 514/438; 514/451; 514/461

(58) Field of Classification Search ............ 514/374, 514/359, 222.2, 432, 438, 451, 461
See application file for complete search history.

(56) References Cited

U.S. PATENT DOCUMENTS

| | | | |
|---|---|---|---|
| 5,153,210 | A | 10/1992 | Ainsworth et al. |
| 6,005,116 | A | 12/1999 | Kojima et al. |
| 7,078,422 | B2 | 7/2006 | Sakuma et al. |
| 2004/0152744 | A1 | 8/2004 | Sakuma et al. |
| 2007/0105868 | A1 | 5/2007 | Kusuda et al. |
| 2008/0167378 | A1 | 7/2008 | Fukatsu et al. |
| 2008/0249137 | A1 * | 10/2008 | Lin et al. .......... 514/347 |

FOREIGN PATENT DOCUMENTS

| | | |
|---|---|---|
| EP | 0 236 624 A2 | 9/1987 |
| EP | 0 885 891 A1 | 12/1998 |
| EP | 1 371 650 A1 | 12/2003 |
| EP | 1 666 472 A1 | 6/2006 |
| JP | 11139975 A * | 5/1999 |
| JP | 199139975 A | 5/1999 |
| WO | WO97/31906 A1 | 9/1997 |
| WO | WO 0105391 A2 * | 1/2001 |
| WO | WO02/076957 A1 | 10/2002 |
| WO | WO2005/028453 A1 | 3/2005 |
| WO | WO2005/051373 A1 | 6/2005 |

* cited by examiner

*Primary Examiner* — Sreeni Padmanabhan
*Assistant Examiner* — Kendra D Carter
(74) *Attorney, Agent, or Firm* — Kenrick L. Vidale; John C. Todaro

(57) ABSTRACT

The present invention relates to a compound represented by formula (I), which has a GPR120 agonist action and thus is useful for treatment of diabetes mellitus or hyperlipidemia, or a pharmaceutically acceptable salt thereof. In the formula, (AA) represents a phenyl or the like, which may be substituted with a lower alkoxy group or the like; (BB) represents a divalent group or the like, derived by removal of two hydrogen atoms from a benzene which may be substituted with a halogen atom or the like; X represents a spacer having a main chain composed of 1-8 carbon atoms wherein 1-3 carbon atoms in the main chain may be substituted with an oxygen atom or the like; and Y represents a hydrogen atom or the like.

5 Claims, No Drawings

PHENYL-ISOXAZOL-3-OL DERIVATIVE

CROSS REFERENCE TO RELATED APPLICATIONS

This application is a U.S. National Phase application under 35 U.S.C. §371 of PCT Application No. PCT/JP2007/073099, filed 29 Nov. 2007, which claims priority under 35 U.S.C. §365(b) from Japanese No. JP2006-325220, filed 1 Dec. 2006.

FIELD OF THE INVENTION

The present invention relates to phenyl-isoxazol-3-ol derivatives that are useful in the pharmaceutical field. The compounds act as GPR120 receptor (14273) function regulating agents, which are useful as drugs for treating and/or preventing diabetes mellitus, obesity and hyperlipidemia.

BACKGROUND OF THE INVENTION

GPR120, a G protein-coupled receptor, causes intracellular signaling through binding with unsaturated long chain fatty acid, such as alpha-linoleic acid, to induce various biological reactions. Actions of GPR120 and its ligand have been reported to promote secretion of GLP-1 (glucagon-like-peptide-1) having the function of reducing a blood glucose level in the gastrointestinal cell lines. GLP-1, which is a peptide hormone released from L cells which are enteroendocrine cells present in the ileum, the large intestine and the like, has been found to induce insulin secretion depending on a blood glucose level. Accordingly, compounds having the action of promoting GLP-1 secretion are expected as agents for treating diabetes mellitus that allow avoidance of the risk of hypoglycemia due to drug overdosage. GLP-1 is also suggested to be efficacious for delaying the apoptosis of beta cells in type II diabetes mellitus or prolonging the efficacy of islet cell transplantation against type I diabetes mellitus because of having the action of inducing pancreatic beta-cell growth and differentiation from stem cells. GPR120 is known to be also expressed in adipocytes. GPR120 has been found to be increasingly expressed by adipose differentiation induction. In addition, actions of GPR120 and its ligand have been reported to suppress lipolysis in adipose-differentiated cells. A high blood lipid level is known to be one of the causes of insulin resistance. Suppression of lipolysis by a GPR120 agonist is thus expected to decrease the level of free fatty acid in blood to normalize a blood lipid level, resulting in improvement in insulin resistance. Furthermore, GPR120 is also expressed in the pituitary gland, and a GPR120 ligand is reported to suppress adrenocorticotropic hormone secretion. Adrenocorticotropic hormone promotes glucocorticoid secretion downstream thereof to induce action such as promotion of glyconeogenesis in the liver, inhibitory action against glucose uptake in muscle and peripheral tissue, lipolysis in adipose tissue or release of fatty acid or glycerol. Accordingly, GPR120 is considered to exhibit hypoglycemic action or blood lipid lowering action via suppression action against adrenocorticotropic hormone secretion even in the center. In light of the above description, a compound having GPR120 agonist activity is considered to be extremely useful as an agent for treating and/or preventing diabetes mellitus and hyperlipidemia.

Compounds structurally related to a compound according to an embodiment of the present invention include a compound represented by the following formula:

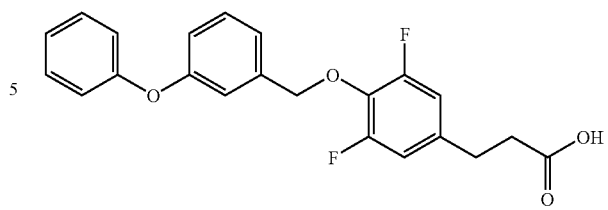

which is described (see WO 2005/051373).

The compound represented by the above formula has a commonality, with the compound according to an embodiment of the present invention, of having a GPR120 (14273) receptor) function regulating action. However, the compound represented by the above formula differs from the compound according to an embodiment of the present invention in that one end of a group bound to difluorophenyl is hydroxycarbonyl ethyl in the compound represented by the above formula whereas it is 3-hydroxyisoxazolyl in the compound according to an embodiment of the present invention.

Non-Patent Document 1: Nature Medicine, vol. 11, No. 1, January 2005, pp. 90-94

SUMMARY OF THE INVENTION

It is desirable to provide a novel phenyl-isoxazol-3-ol derivative having a GPR120 (14273) inhibitory action.

We, the present inventors have assiduously studied to develop a compound having a GPR120 (14273) function regulating action, particularly having an agonist action, and found that the compound according to an embodiment of the present invention is efficacious as the compound having the GPR120 (14273) function regulating action, and the invention was thus accomplished based on such findings.

Specifically, the present invention relates to a compound represented by formula (I):

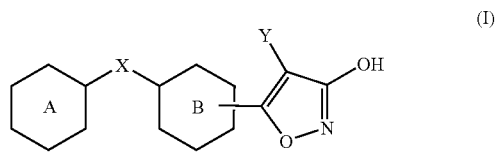

or a pharmaceutically acceptable salt thereof, wherein:

represents phenyl or 5- to 6-membered heteroaryl optionally substituted with same or different 1 to 4 groups selected from the group consisting of:

lower alkyl, cycloalkyl, lower alkylthio, lower alkyl, cycloalkylthio, lower alkylamino, cycloalkylamino, nitro, halogen atom, cyano, lower alkylsulfonyl, phenoxy, phenyl, heteroaryloxy and heteroaryl;

represents a divalent group in which 2 hydrogen atoms are eliminated from benzene, pyridine, pyrazine, pyrimidine or pyridazine optionally substituted with same or different, 1 to 4 groups selected from the group consisting of:
halogen atom, lower alkyl, lower alkoxy, cyano and lower alkylsulfonyl;
X represents a spacer having a main chain composed of 1 to 8 carbon atoms, and 1 to 3 carbon atoms of said main chain are optionally substituted with oxygen, sulfur or nitrogen;
said spacer is further optionally substituted with same or different, 1 to 3 lower alkoxy, hydroxy or oxo; and
Y represents hydrogen atom, lower alkyl optionally substituted with same or different, 1 to 3 lower alkyl or halogen atom, lower alkoxy or halogen.

The present invention also relates to a GPR120 function regulating agent containing a compound represented by formula (I) or a pharmaceutically acceptable salt thereof as an active ingredient. Particularly, the present invention relates to a GPR120 agonist containing a compound represented by formula (I) or a pharmaceutically acceptable salt thereof as an active ingredient.

Furthermore, the present invention relates to a pharmaceutical composition containing a compound represented by formula (I) and a pharmaceutically acceptable carrier.

A compound (I) according to an embodiment of the present invention or a pharmaceutically acceptable salt thereof has a strong GPR120 (14273) function regulating action, particularly an agonist action, and is useful for treating and/or preventing diabetes mellitus and hyperlipidemia.

DETAILED DESCRIPTION OF THE INVENTION

The meanings of terms as used herein are described below, and a compound according to an embodiment of the present invention is described in further detail.

The term "halogen atom" encompasses, for example, fluorine, chlorine, bromine and iodine atoms.

The term "lower alkyl group" means a linear or branched $C_{1-6}$ alkyl group, and includes, for example, methyl, ethyl, propyl, isopropyl, butyl, isobutyl, sec-butyl, tert-butyl, pentyl, isoamyl, neopentyl, isopentyl, 1,1-dimethyl propyl, 1-methyl butyl, 2-methyl butyl, 1,2-dimethyl propyl, hexyl, isohexyl, 1-methyl pentyl, 2-methyl pentyl, 3-methyl pentyl, 1,1-dimethyl butyl, 1,2-dimethyl butyl, 2,2-dimethyl butyl, 1,3-dimethyl butyl, 2,3-dimethyl butyl, 3,3-dimethyl butyl, 1-ethyl butyl, 2-ethyl butyl, 1,2,2-trimethyl propyl and 1-ethyl-2-methyl propyl.

The term "lower alkoxy" means a group, in which a hydrogen atom of a hydroxy is substituted with the above-mentioned lower alkyl, and includes, for example, methoxy, ethoxy, propoxy, isopropoxy, butoxy, sec-butoxy, tert-butoxy, pentyloxy, isopentyloxy, hexyloxy and isohexyloxy.

The term "cycloalkyl" means a $C_{3-7}$ cycloalkyl, specifically includes, for example, cyclopropyl, cyclobutyl, cyclopentyl, cyclohexyl and cycloheptyl.

The term "lower alkylthio" means a group, in which a hydrogen atom of a thiol is substituted with the above-mentioned lower alkyl, and specifically includes, for example, methylthio, ethylthio, n-propylthio, isopropylthio, butylthio and isobutylthio.

The term "cycloalkyloxy" means a group, in which a hydrogen atom of a hydroxy is substituted with the above-defined cycloalkyl, and specifically includes, for example, cyclopropyloxy, cyclobutyloxy, cyclopentyloxy and cyclohexyloxy.

The term "cycloalkylthio" means a group, in which a hydrogen atom of a thiol is substituted with the above-defined cycloalkyl, and specifically includes, for example, cyclopropylthio, cyclobutylthio, cyclopentylthio and cyclohexylthio.

The term "lower alkylamino" means a group, in which one or two hydrogen atoms of an amino are substituted with the above-defined lower alkyl which are same or different, and specifically includes, for example, methylamino, ethylamino, n-propylamino, isopropylamino, dimethylamino, diethylamino and ethylmethylamino.

The term "cycloalkylamino" means a group, in which one or two hydrogen atoms of an amino are substituted with the above-defined cycloalkyl which are same or different, and specifically includes, for example, cyclopropylamino, cyclobutylamino, cyclopentylamino and cyclohexylamino.

The term "lower alkylsulfonyl group" includes, for example, methylsulfonyl, ethylsulfonyl, propylsulfonyl and isopropylsulfonyl.

Each symbol used in formula (I) in accordance with an embodiment of the present invention

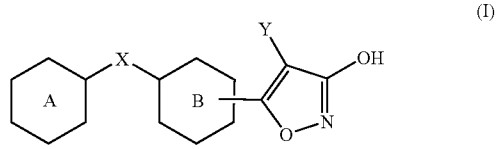

(I)

is specifically described.
In the formula (I), formula (A):

represents phenyl or 5- to 6-membered heteroaryl optionally substituted with same or different 1 to 4 groups selected from the group consisting of:
lower alkyl, cycloalkyl, lower alkylthio, lower alkyl, cycloalkylthio, lower alkylamino, cycloalkylamino, nitro, halogen atom, cyano, lower alkylsulfonyl, phenoxy, phenyl, heteroaryloxy and heteroaryl.

"5- or 6-membered heteroaryl" represented by formula (A) means a heteroaryl having 1-3 same or different hetero atoms selected from the group consisting of nitrogen, sulfur and oxygen atoms, and specifically includes, for example, pyridinyl, oxazolyl, isoxazolyl, thiazolyl, thiadiazolyl, imidazolyl, tetrazolyl and pyrazolyl.

"Phenyl or 5- or 6-membered heteroaryl" represented by formula (A) preferably include phenyl, pyridinyl, oxazolyl, isoxazolyl and thiazolyl, more preferably phenyl and pyridinyl.

A group represented by formula (A) may have, on the group, 1-4 same or different groups selected from the group consisting of lower alkoxy, cycloalkyloxy, lower alkylthio, lower alkyl, cycloalkylthio, lower alkyl, lower alkylamino, cycloalkylamino, nitros, halogen atoms, cyano, lower alkylsulfonyl, phenoxy, phenyl, heteroaryloxy and heteroaryl.

Lower alkoxy of the substituents have the same meaning as the above-defined "lower alkoxy" and specifically include, for example, methoxy, ethoxy, propoxy and isopropoxy.

Cycloalkyloxy of the substituents have the same meaning as the above-defined "cycloalkyloxy" and specifically include, for example, cyclopropyloxy, cyclobutyloxy, cyclopentyloxy and cyclohexyloxy.

Lower alkylthio of the substituents have the same meaning as the above-defined "lower alkylthio" and specifically include, for example, methylthio, ethylthio, propylthio and isopropylthio.

Lower alkyl of the substituents have the same meaning as the above-defined "lower alkyl" and specifically include, for example, methyl, ethyl, n-propyl, isopropyl and butyl.

Cycloalkylthio of the substituents have the same meaning as the above-defined "cycloalkylthio" and specifically include, for example, cyclobutylthio, cyclopentylthio and cyclohexylthio.

Lower alkylamino of the substituents have the same meaning as the above-defined "lower alkylamino" and specifically include, for example, methylamino, ethylamino, isopropylamino, dimethylamino, diethylamino and ethylmethylamino.

Cycloalkylamino of the substituents have the same meaning as the above-defined "cycloalkylamino" and specifically include, for example, cyclopropylamino, cyclobutylamino, cyclopentylamino and cyclohexylamino.

Halogen atoms of the substituents have the same meaning as the above-defined "halogen atoms" and specifically include, for example, fluorine, chlorine and bromine atoms.

Lower alkylsulfonyl of the substituents have the same meaning as the above-defined "lower alkylsulfonyl" and specifically include, for example, methylsulfonyl, ethylsulfonyl, propylsulfonyl and isopropylsulfonyl.

Heteroaryloxy of the substituents specifically include, for example, pyridinyloxy, pyrazinyloxy and pyrimidinyloxy.

Heteroaryl of the substituents specifically include, for example, pyridinyl, pyrazinyl, pyrimidinyl and pyridazinyl.

Lower alkoxy, cycloalkyloxy, lower alkylthio, lower alkyl, lower alkylamino, phenoxy, phenyl, heteroaryloxy and heteroaryl of the substituents may be substituted with same or different, 1-3 halogen atoms or lower alkoxy.

Preferred among these substituents which may be in the represented by formula (A) are a lower alkoxy, a cycloalkyloxy, a lower alkylthio, a lower alkyl, a lower alkylamino, a cycloalkylamino, a nitro, a halogen atom, a cyano or a lower alkylsulfonyl.

Formula (B)

represents a divalent group in which 2 hydrogen atoms are eliminated from benzene, pyridine, pyrazine, pyrimidine or pyridazine optionally substituted with same or different, 1 to 4 groups selected from the group consisting of:
halogen atom, lower alkyl, lower alkoxy, cyano and lower alkylsulfonyl.

A group represented by formula (B) may also have same or different, 1-4 groups selected from the group consisting of halogen atoms, lower alkyl, lower alkoxy, cyano and lower alkylsulfonyl on the ring.

Among the substituents which may be in the groups represented by formula (B), a lower alkyl or lower alkoxy may be substituted with a hydroxy, a lower alkoxy or same or different, 1-3 halogen atoms.

X represents a spacer having a main chain composed of 1 to 8 carbon atoms, and 1 to 3 carbon atoms of said main chain are optionally substituted with oxygen, sulfur or nitrogen;

said spacer is further optionally substituted with same or different, 1 to 3 lower alkoxy, hydroxy or oxo.

The number of atoms in the main chain of X is preferably from 1 to 4.

X may be substituted with same or different, 1-3 lower alkoxy, hydroxy or oxo.

X specifically includes groups represented by formula (II):

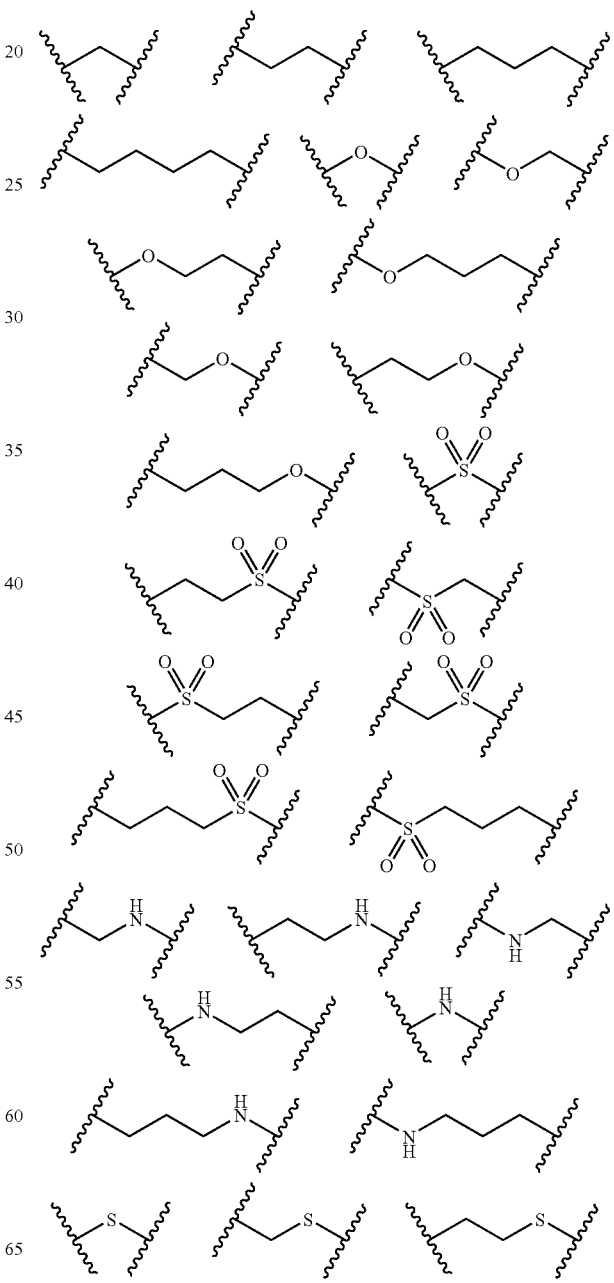

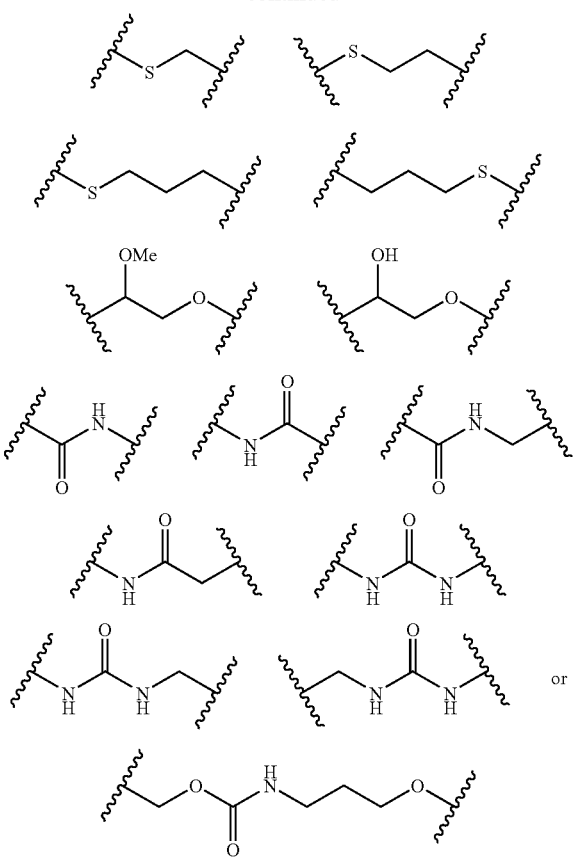

wherein

represents a binding position to

among which preferred are, for example, groups represented by

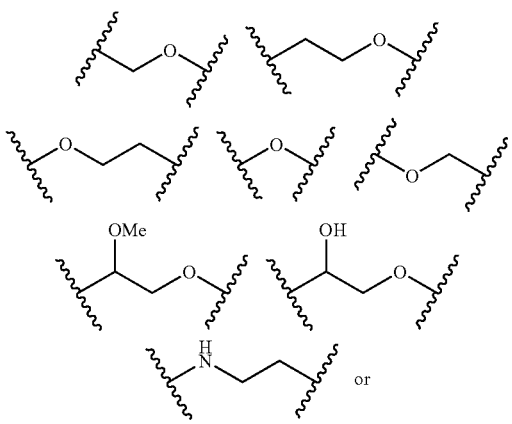

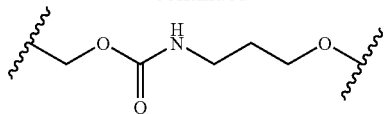

wherein each symbol has the same definition specified above, more preferred are groups represented by formula (II-2):

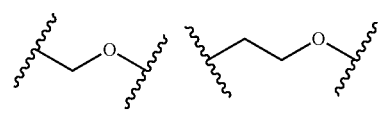
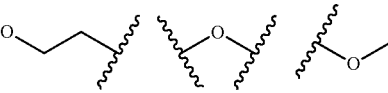
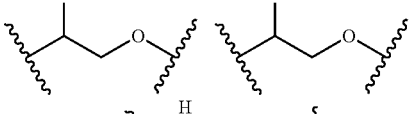
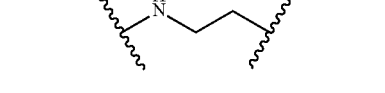

wherein each symbol has the same definition specified above.

Y means a hydrogen atom, a lower alkyl, optionally substituted with same or different, 1-3 lower alkoxy or halogen atoms, a lower alkoxy and a halogen atom.

A lower alkyl represented by Y has the same meaning as the above-defined a lower alkyl and specifically includes, for example, a methyl, ethyl, n-propyl and isopropyl.

The lower alkyl may be substituted with same or different, 1-3 lower alkoxy or halogen atoms.

A lower alkoxy represented by Y has the same meaning as the above-defined a lower alkoxy and specifically includes, for example, methoxy, ethoxy, n-propyloxy and isopropyloxy.

A halogen atom represented by Y has the same meaning as the above-defined a halogen atom and specifically includes, for example, fluorine, chlorine and bromine atoms.

(i) Preferred embodiments of the present invention include those wherein X represents formula (II):

(II)

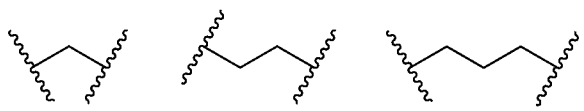
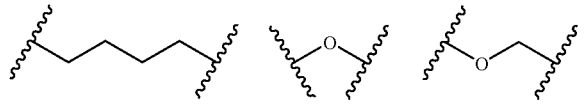
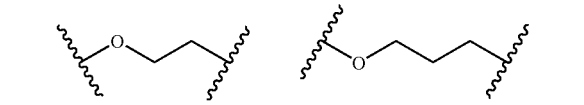
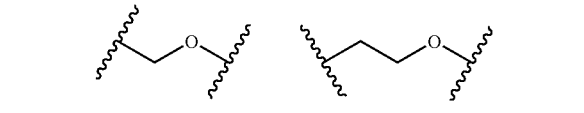

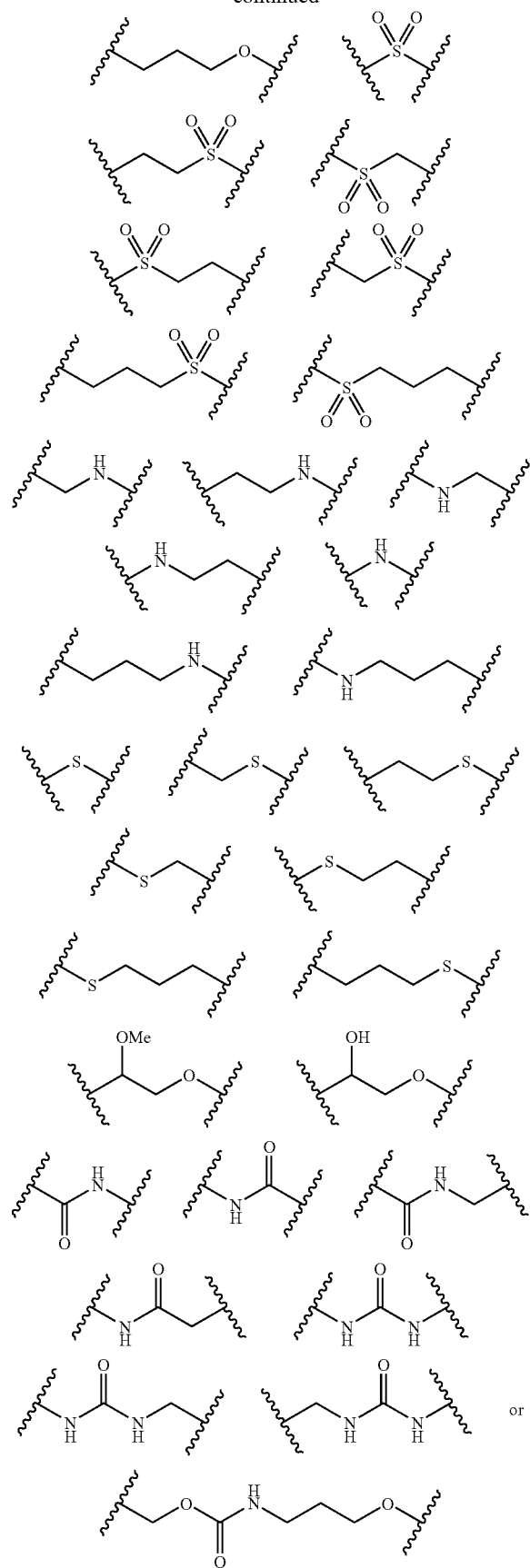

wherein represents a binding position to

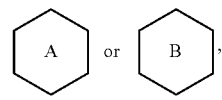

in the formula (I).

(ii) Furthermore, other preferred embodiments of the present invention include those wherein X represents formula (II-1):

(II-1)

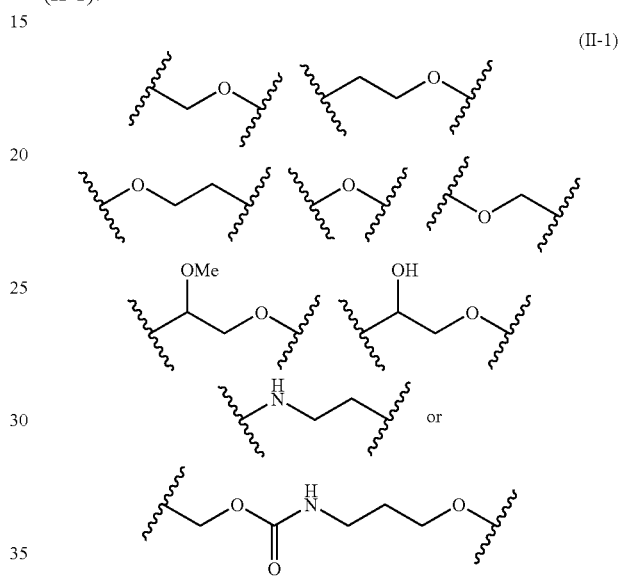

wherein represents a binding position to

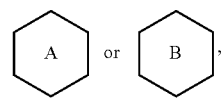

in the formula (I).

(iii) Furthermore, other preferred embodiments of the present invention include those wherein, in the foregoing (i), X in the formula (I) represents formula (II-2)

(II-2)

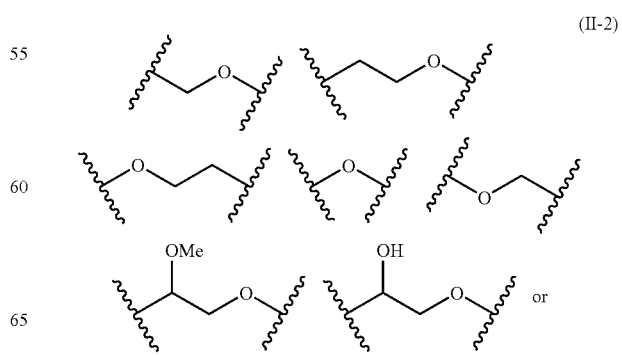

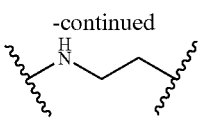

wherein each symbol has the same definition specified above.

(iv) Other preferred embodiments of the present invention include those wherein X in the formula (I) represents any of the formulas (II), (II-1) or (II-2), wherein

represents phenyl or 5- to 6-membered heteroaryl optionally substituted with same or different 1 to 4 groups selected from the group consisting of:
lower alkyl, cycloalkyl, lower alkylthio, lower alkyl, cycloalkylthio, lower alkylamino, cycloalkylamino, nitro, halogen atom, cyano, lower alkylsulfonyl, phenoxy, phenyl, heteroaryloxy and heteroaryl; and

represents a divalent group in which 2 hydrogen atoms are eliminated from benzene, pyridine, pyrazine, pyrimidine or pyridazine optionally substituted with same or different, 1 to 4 groups selected from the group consisting of:
halogen atom, lower alkyl, lower alkoxy, cyano and lower alkylsulfonyl.

(v) Furthermore, other preferred embodiments of the present invention include those wherein X in the formula (I) represents any of the formulas (II), (II-1) or (II-2), wherein

represents a phenyl, pyridinyl, oxazolyl, isoxazolyl or thiazolyl optionally substituted with same or different, 1-4 groups selected from the group consisting of lower alkoxy, cycloalkyl, lower alkylthio, lower alkyl, cycloalkylthio, lower alkylamino, cycloalkylamino, nitro, halogen atoms, cyano and lower alkylsulfonyl; and

represents a divalent group in which 2 hydrogen atoms are eliminated from a benzene, pyridine, pyrazine, pyrimidine or pyridazine optionally substituted with same or different, 1-4 groups selected from the group consisting of halogen atoms, lower alkyl, lower alkoxy, cyano and lower alkylsulfonyl.

(vi) Furthermore, other preferred embodiments of the present invention include those wherein X in the formula (I) represents any of the formulas (II), (II-1) or (II-2), wherein:

represents a phenyl, pyridinyl, oxazolyl, isoxazolyl or thiazolyl optionally substituted with same or different, 1-4 groups selected from the group consisting of lower alkoxy, cycloalkyl, lower alkylthio, lower alkyl, cycloalkylthio, lower alkylamino, cycloalkylamino, nitro, halogen atoms, cyano and lower alkylsulfonyl; and

represents a divalent group in which 2 hydrogen atoms are eliminated from a benzene, pyridine, pyrazine, pyrimidine or pyridazine optionally substituted with same or different, 1 to 4 groups selected from the group consisting of halogen atoms, lower alkyl, lower alkoxy, cyano and lower alkylsulfonyl (except that

represents a phenyl group optionally substituted with same or different, 1-4 groups selected from the group consisting of lower alkoxy, cycloalkyl, lower alkylthio, lower alkyl, cycloalkylthio, lower alkylamino, cycloalkylamino, nitro, halogen atoms, cyano and lower alkylsulfonyl; and

represents a divalent group in which 2 hydrogen atoms are eliminated from a benzene optionally substituted with same or different, 1-4 groups selected from the group consisting of halogen atoms, lower alkyl, lower alkoxy, cyano and lower alkylsulfonyl).

(vii) Furthermore, other preferred embodiments of the present invention include those wherein the formula (I) indicates a compound represented by formula (I-1):

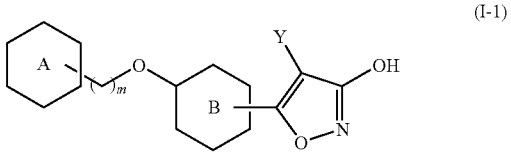

(I-1)

or a pharmaceutically acceptable salt thereof, wherein:

m represents an integer of from 0 to 2;

when m is 1 or 2, a methylene chain in

may be substituted with same or different, one or two hydroxy or lower alkoxy;

Y represents a hydrogen atom, a lower alkyl group optionally substituted with same or different 1-3 lower alkoxy or halogen atoms, a lower alkoxy or a halogen atom; and the other symbols have the same definitions specified above.

(viii) Furthermore, other preferred embodiments of the present invention include those wherein the formula (I) indicates a compound represented by formula (I-1)

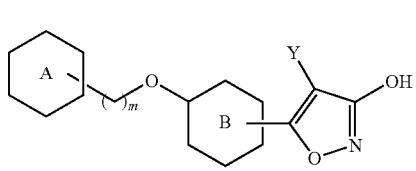

(I-1)

wherein m represents an integer of from 0 to 2;
when m is 1 or 2, a methylene chain in

may be substituted with same or different, one or two hydroxy or lower alkoxy;

Y represents a hydrogen atom, a lower alkyl optionally substituted with same or different 1-3 lower alkoxy or halogen atoms, a lower alkoxy or a halogen atom; and the other symbols have the same definitions specified above (except that

represents a phenyl optionally substituted with same or different, 1-4 groups selected from the group consisting of lower alkoxy, cycloalkyl, lower alkylthio, lower alkyl, cycloalkylthio, lower alkylamino, cycloalkylamino, nitro, halogen atoms, cyano and lower alkylsulfonyl; and

represents a divalent group in which 2 hydrogen atoms are eliminated from a benzene optionally substituted with same or different, 1-4 groups selected from the group consisting of halogen atoms, lower alkyl, lower alkoxy, cyano and lower alkylsulfonyl).

(ix) Furthermore, other preferred embodiments of the present invention include those wherein, in the foregoing (vii) or (viii), the formula (I-1) is formula (I-2),

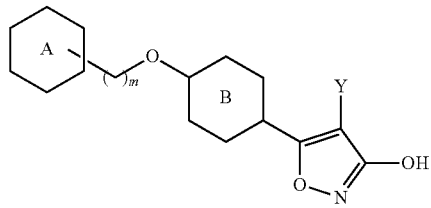

(I-2)

wherein each symbol has the same definition specified above.

(x) Furthermore, other preferred embodiments of the present invention include those wherein, in the foregoing (vii), (viii) or (ix),

represents a phenyl, pyridinyl, oxazolyl, isoxazolyl or thiazolyl optionally substituted with same or different, 1-4 groups selected from the group consisting of lower alkoxy, cycloalkyl, lower alkylthio, lower alkyl, cycloalkylthio, lower alkylamino, cycloalkylamino, nitro, halogen atoms, cyano and lower alkylsulfonyl; and

represents a divalent group in which 2 hydrogen atoms are eliminated from a benzene, pyridine, pyrazine, pyrimidine or pyridazine optionally substituted with same or different, 1-4 groups selected from the group consisting of halogen atoms, lower alkyl, lower alkoxy, cyano and lower alkylsulfonyl.

(xi) Furthermore, other preferred embodiments of the present invention include the foregoing (x) (except that

represents a phenyl optionally substituted with same or different, 1-4 groups selected from the group consisting of lower alkoxy, cycloalkyl, lower alkylthio, lower alkyl, cycloalkylthio, lower alkylamino, cycloalkylamino, nitro, halogen atoms, cyano and lower alkylsulfonyl; and

represents a divalent group in which 2 hydrogen atoms are eliminated from a benzene optionally substituted with same or different, 1-4 groups selected from the group consisting of halogen atoms, lower alkyl, lower alkoxy, cyano and lower alkylsulfonyl).

Furthermore, examples of specific compounds encompassed by formula (I) according to an embodiment of the present invention include compounds represented by
5-(4-((2-(cyclopentyloxy)pyridin-3-yl)methoxy)phenyl) isoxazol-3-ol;
5-(4-((2-isopropoxypyridin-3-yl)methoxy)phenyl)isoxazol-3-ol;
5-(4-((6-phenoxypyridin-2-yl)methoxy)phenyl)isoxazol-3-ol;
5-(4-((5-phenylisoxazol-3-yl)methoxy)phenyl)isoxazol-3-ol;
5-(4-((2-(3-fluorophenoxy)pyridin-3-yl)methoxy)phenyl) isoxazol-3-ol;
5-(4-((2-phenylpyridin-3-yl)methoxy)phenyl)isoxazol-3-ol;
5-(3-fluoro-4-((2-phenoxypyridin-3-yl)methoxy)phenyl) isoxazol-3-ol;
5-(3-fluoro-4-((2-phenoxypyridin-3-yl)methoxy)phenyl) isoxazol-3-ol;
5-(6-((2-phenoxybenzyl)oxy)pyridin-3-yl)isoxazol-3-ol;
5-(5-((2-phenoxybenzyl)oxy)pyridin-2-yl)isoxazol-3-ol;
5-(4-((2-phenoxypyridin-4-yl)methoxy)phenyl)isoxazol-3-ol;
5-(4-((2-phenoxypyridin-3-yl)methoxy)phenyl)isoxazol-3-ol;
5-(3,5-difluoro-4-((2-phenoxypyridin-3-yl)methoxy)phenyl)isoxazol-3-ol;
5-(4-((2-(4-fluorophenoxy)pyridin-3-yl)methoxy)phenyl) isoxazol-3-ol;
5-(4-((2-(isopropylthio)pyridin-3-yl)methoxy)phenyl)isoxazol-3-ol;
5-(4-((2-isopropoxybenzyl)oxy)phenyl)isoxazol-3-ol;
5-(4-((2-(pyridin-3-yloxy)benzyl)oxy)phenyl)isoxazol-3-ol;
5-(4-((3-fluoro-2-phenoxybenzyl)oxy)phenyl)isoxazol-3-ol;
5-(4-((2-fluoro-6-phenoxybenzyl)oxy)phenyl)isoxazol-3-ol;
5-(4-((2-(2,6-difluorophenoxy)pyridin-3-yl)methoxy)phenyl)isoxazol-3-ol;
5-(4-((5-fluoro-2-phenoxybenzyl)oxy)phenyl)isoxazol-3-ol;
5-(4-((3-isopropoxybenzyl)oxy)phenyl)isoxazol-3-ol;
5-(4-((3-phenoxypyridin-2-yl)methoxy)phenyl)isoxazol-3-ol;
5-(4-((2-isobutylpyridin-3-yl)methoxy)phenyl)isoxazol-3-ol;
5-(4-((3-phenoxybenzyl)oxy)phenyl)isoxazol-3-ol;
5-(3,5-difluoro-4-((2-phenoxybenzyl)oxy)phenyl)isoxazol-3-ol;
5-(4-((2-phenoxybenzyl)oxy)phenyl)isoxazol-3-ol;
5-(3-fluoro-4-((2-phenoxybenzyl)oxy)phenyl)isoxazol-3-ol;
5-(4-((2-phenoxybenzyl)oxy)benzyl)isoxazol-3-ol;
5-(4-(2-(5-methyl-2-phenyl-1,3-thiazol-4-yl)ethoxy)phenyl) isoxazol-3-ol;
5-(4-((5-phenylisoxazol-4-yl)methoxy)phenyl)isoxazol-3-ol;
benzyl(3-(4-(3-hydroxyisoxazol-5-yl)phenoxy)propyl)carbamate;
5-(4-(2-(5-methyl-2-phenyl-1,3-oxazol-4-yl)ethoxy)phenyl) isoxazol-3-ol;
5-(4-(2-(3-((6-fluoropyridin-3-yl)oxy)phenyl)ethoxy)phenyl)isoxazol-3-ol;
5-(6-(2-(3-isopropoxyphenyl)ethoxy)pyridin-3-yl)isoxazol-3-ol;
5-(4-(2-(3-ethoxyphenoxy)ethyl)phenyl)isoxazol-3-ol;
5-(4-(2-(3-nitrophenyl)ethoxy)phenyl)isoxazol-3-ol;
5-(4-(2-(3-(phenoxyphenyl)ethoxy)phenyl)isoxazol-3-ol;
5-(4-(1-naphthylmethoxy)phenyl)isoxazol-3-ol;
5-(4-(2-(6-(4-fluorophenyl)pyridin-2-yl)ethoxy)phenyl) isoxazol-3-ol;
5-(4-(2-(3-isopropylamino)phenyl)ethoxy)phenyl)isoxazol-3-ol;
5-(4-(2-(3-(6-fluoropyridin-3-yl)phenyl)ethoxy)phenyl) isoxazol-3-ol;
5-(4-(2-(3-(methoxymethyl)phenyl)ethoxy)phenyl)isoxazol-3-ol;
5-(4-(2-(3-propylphenoxy)ethyl)phenyl)isoxazol-3-ol;
5-(4-((3-phenoxyphenoxy)methyl)phenyl)isoxazol-3-ol;
5-(4-(2-(2-fluoro-5-methoxyphenyl)ethoxy)phenyl)isoxazol-3-ol;
5-(4-(2-(2-isopropoxypyridin-4-yl)ethoxy)phenyl)isoxazol-3-ol;
5-(4-(2-(6-isopropoxypyridin-2-yl)ethoxy)phenyl)isoxazol-3-ol;
5-(4-(2-(3-methoxyphenyl)ethoxy)phenyl)isoxazol-3-ol;
5-(4-(2-(3-isopropoxyphenyl)ethoxy)phenyl)isoxazol-3-ol;
5-(4-(2-(4-fluoro-3-methoxyphenyl)ethoxy)phenyl)isoxazol-3-ol;
5-(4-(2-(2-phenoxypyridin-4-yl)ethoxy)phenyl)isoxazol-3-ol;
5-(4-(2-(3-(cyclohexyloxy)phenyl)ethoxy)phenyl)isoxazol-3-ol;
5-(4-(2-(2-phenoxyphenyl)ethoxy)phenyl)isoxazol-3-ol;
5-(4-(2-methoxy-2-(3-methoxyphenyl)ethoxy)phenyl)isoxazol-3-ol;
5-(4-(2-hydroxy-2-(3-methoxyphenyl)ethoxy)phenyl)isoxazol-3-ol;
5-(4-(3-phenoxypropoxy)phenyl)isoxazol-3-ol;
5-(4-(2-(3-ethoxyphenyl)ethoxy)phenyl)isoxazol-3-ol;
5-(4-(2-chloro-4-(trifluoromethyl)phenoxy)phenyl)isoxazol-3-ol;
5-(4-(2-chloro-4-(trifluoromethyl)phenoxy)-3-fluorophenoxy)isoxazol-3-ol; and
5-(4-(2-chloro-4-(trifluoromethyl)phenoxy)-3,5-difluorophenoxy)isoxazol-3-ol, and
pharmaceutically acceptable salts thereof.

A process for producing a compound according to an embodiment of the present invention will now be described.

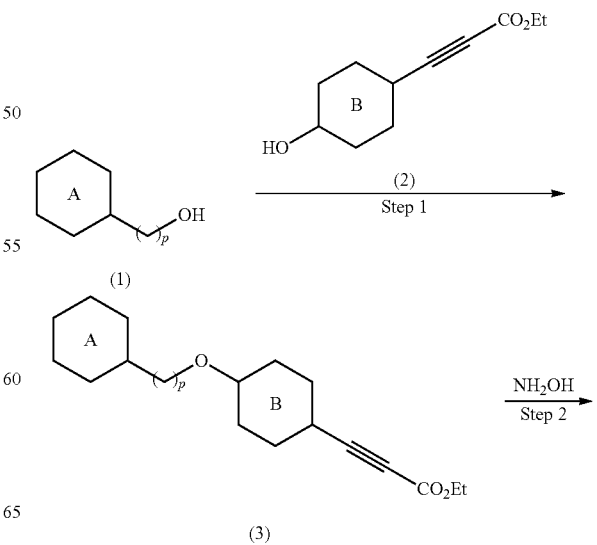

17

-continued

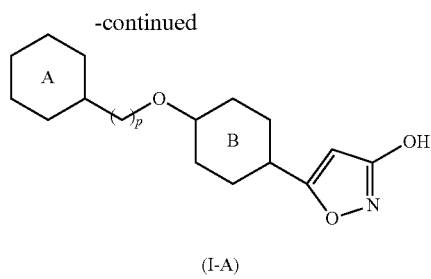

(I-A)

wherein p represents an integer of from 1 to 4; and the other symbols have the same definitions specified above.

(Step 1)

This step is a process for producing a compound (3) by reacting a compound (1) with a compound (2).

The reaction of the compound (1) with the compound (2) is a so-called Mitsunobu reaction, which may be performed by methods as described in documents (e.g., Mitsunobu, O., "The Use of Diethyl Azodicarboxylate and Triphenylphosphine in Synthesis and Transformation of Natural Products," Synthesis 1 (1981), pp. 1-28), methods equivalent thereto or combinations of them with ordinary methods in the presence of phosphine and azo compounds.

An amount of the compound (1) used in this step is generally 1-100 equivalents, preferably 1-5 equivalents, per equivalent of the compound (2).

Examples of compounds (1) used in this step include (2-(cyclopentyloxy)pyridin-3-yl)methanol, (2-phenoxyphenyl)methanol, 2-(5-methyl-2-phenyl-1,3-thiazol-4-yl)ethanol, and the like. Examples of phosphine compounds used in this step include triphenylphosphine, triethylphosphine, and the like.

An amount of the phosphine compound used is generally 1-100 equivalents, preferably 1-5 equivalents, relative to 1 equivalent of the compound (2).

Compounds (2) used in this step include, for example, ethyl-3-(4-hydroxyphenyl)-2-propinoate, ethyl-3-(4-(hydroxymethyl)phenyl)-2-propinoate, ethyl(3-(4-(2-hydroxyethyl)phenyl)-2-propinoate, and the like.

Azo compounds used include ethyl azodicarboxylate, diisopropyl azodicarboxylate, and the like.

An amount of the azo compound used is generally 1-100 equivalents, preferably 1-5 equivalents, relative to 1 equivalent of the compound (2).

The reaction time in this step is generally 0.1-72 hours, preferably 0.5-24 hours.

The reaction temperature in this step is generally 0-200° C., preferably 0-50° C.

Reaction solvents used in this step, but, unless interfering with the reaction, are not limited to, e.g., tetrahydrofuran and diethyl ether.

The compound (3) thus obtained may be subjected to the next step with or without isolation and purification by means of known separation/purification means such as concentration, concentration in vacuo, crystallization, extraction with solvent, re-precipitation and chromatography.

(Step 2)

This step is a process for producing a compound (I-A) according to an embodiment of the present invention by reacting the compound (3) obtained in the step 1 with hydroxyamine in the presence of a base.

Bases used in this step include, for example, sodium hydroxide and potassium hydroxide.

18

An amount of the base used is generally 1-100 equivalents, preferably 1-5 equivalents, per equivalent of the compound (3).

An amount of hydroxyamine used is generally 1-100 equivalents, preferably 1-5 equivalents, per equivalent of the compound (3).

The reaction time in this step is generally 0.1-72 hours, preferably 0.5-24 hours.

The reaction temperature in this step is generally 0-100° C., preferably 0-40° C.

Reaction solvents used in this step, but, unless interfering with the reaction, are not limited to, e.g., methanol and ethanol.

The compound (I-A) thus obtained may be subjected to isolation and purification by means of known separation/purification means such as concentration, concentration in vacuo, crystallization, extraction with solvent, re-precipitation and chromatography.

Furthermore, the compound (2) used may be obtained commercially or may be produced, for example, by a process illustrated below.

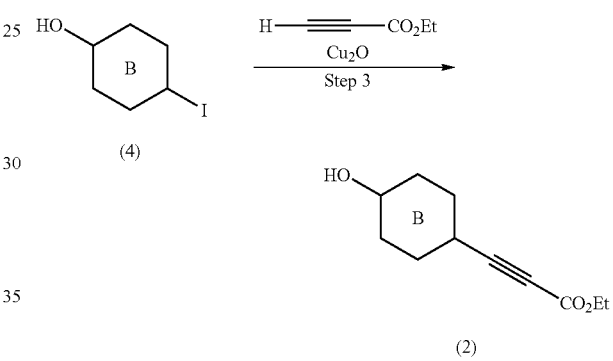

(Step 3)

This step is a process for producing a compound (2) by reacting a compound (4) with ethyl propionate in the presence of copper (II) oxide.

An amount of ethyl propionate used in this step is generally 1-100 equivalents, preferably 1-5 equivalents, relative to 1 equivalent of the compound (4).

Examples of compounds (4) used in this step include 4-iodophenol, 4-iodophenyl methanol, 2-(4-iodophenyl)ethanol, and the like. Methyl propionate may be also used instead of ethyl propionate used in this step.

An amount of copper (II) oxide used in this step is generally 0.1-100 equivalents, preferably 1-5 equivalents, relative to 1 equivalent of the compound (4).

The reaction temperature in this step is generally 0-200° C., preferably 50-120° C.

The reaction time in this step is generally 0-72 hours, preferably 0.5-24 hours.

Reaction solvents used in this step, but, unless interfering with the reaction, are not limited to, e.g., dimethylformamide and N-methylpyrrolidone.

The compound (3) thus obtained may be subjected to the next step with or without isolation and purification by means of known separation/purification means such as concentration, concentration in vacuo, crystallization, extraction with solvent, re-precipitation and chromatography.

Furthermore, the compound (3) may be produced, for example, by the following process:

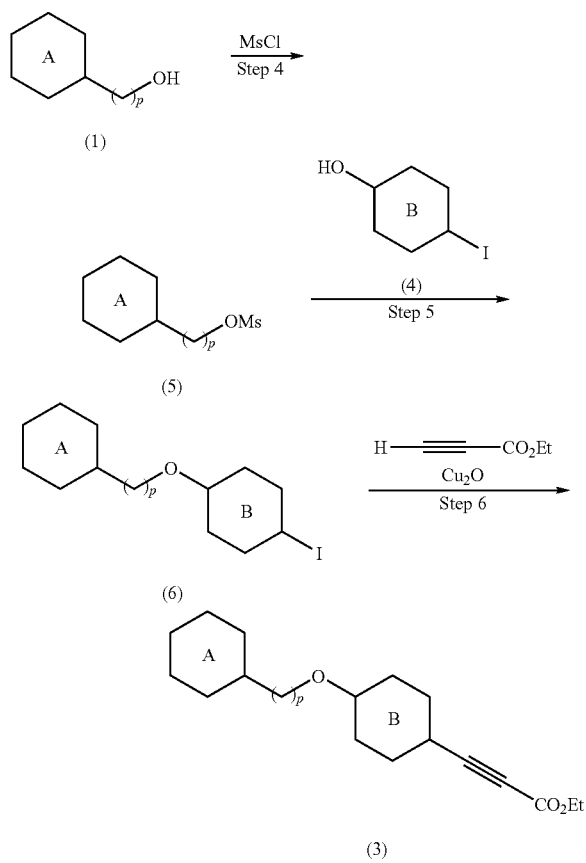

wherein each symbol has the same definition specified above.

(Step 4)

This step is a process for producing a compound (5) by reacting the compound (1) with methanesulfonyl chloride (MsCl) in the presence of a base.

Bases used in this step include, for example, triethylamine, diisopropylethylamine and pyridine.

An amount of the base used in this step is typically 0.1-100 equivalents, preferably 1-5 equivalents, relative to 1 equivalent of the compound (1).

An amount of methanesulfonyl chloride used in this step is generally 1-100 equivalents, preferably 1-5 equivalents, relative to 1 equivalent of the compound (1).

The reaction time in this step is generally 0.1-24 hours, preferably 0.5-3 hours.

The reaction temperature in this step is generally 0-100° C., preferably 0-30° C.

Reaction solvents used in this step, but, unless interfering with the reaction, are not limited to, e.g., ethyl acetate, chloroform and tetrahydrofuran.

The compound (5) thus obtained may be subjected to the next step with or without isolation and purification by means of known separation/purification means such as concentration, concentration in vacuo, crystallization, extraction with solvent, re-precipitation and chromatography.

(Step 5)

This step is a process for producing a compound (6) by reacting the compound (5) with the compound (4) in the presence of a base.

Bases used in this step include, for example, sodium hydride and potassium carbonate.

An amount of the base used in this step is generally 1-100 equivalents, preferably 1-5 equivalents, relative to 1 equivalent of the compound (5).

An amount of the compound (4) used in this step is generally 1-100 equivalents, preferably 1-5 equivalents, relative to 1 equivalent of the compound (5).

The reaction temperature in this step is generally 0-200° C., preferably 0-100° C.

The reaction time in this step is generally 0.1-24 hours, preferably 0.5-3 hours.

Reaction solvents used in this step, but, unless interfering with the reaction, are not limited to, e.g., dimethylformamide and N-methylpyrrolidone.

The compound (6) thus obtained may be subjected to the next step with or without isolation and purification by means of known separation/purification means such as concentration, concentration in vacuo, crystallization, extraction with solvent, re-precipitation and chromatography.

(Step 6)

This step is a process for producing a compound (3) by reacting a compound (6) with ethyl propionate in the presence of copper (II) oxide.

The reaction in this step may be carried out in the same manner as in the above step 3, or according to a method similar to it, or according to a combination thereof with an ordinary method.

The compound (3) thus obtained may be subjected to the next step with or without isolation and purification by means of known separation/purification means such as concentration, concentration in vacuo, crystallization, extraction with solvent, re-precipitation and chromatography.

Furthermore, a compound (I-B) may be produced, for example, by the following process:

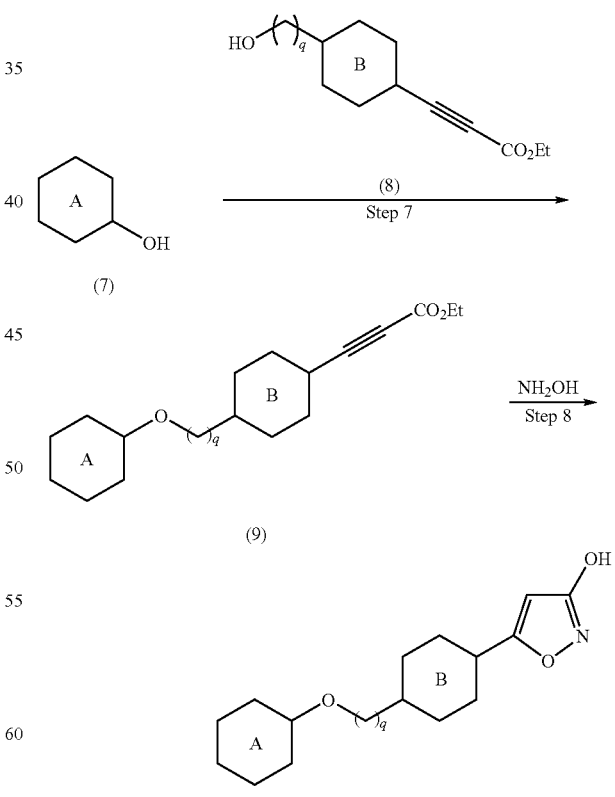

wherein q represents an integer of from 1 to 4; and the other symbols have the same definitions specified above.

(Step 7)

This step is a process for producing a compound (9) by reacting a compound (7) with a compound (8).

This step is a so-called Mitsunobu reaction, which may be carried out in the same manner as in the above step 1, or according to a method similar to it, or according to a combination thereof with an ordinary method.

Compounds (8) used in this step include, for example, ethyl-3-(4-(hydroxymethyl)phenyl)-2-propinoate, ethyl(3-(4-(2-hydroxyethyl)phenyl)-2-propinoate, and the like.

The compound (9) thus obtained may be subjected to the next step with or without isolation and purification by means of known separation/purification means such as concentration, concentration in vacuo, crystallization, extraction with solvent, re-precipitation and chromatography.

(Step 8)

This step is a process for producing a compound (I-B) according to an embodiment of the present invention by reacting the compound (3) obtained in the step 1 with hydroxyamine in the presence of a base.

The reaction in this step may be carried out in the same manner as in the above step 2, or according to a method similar to it, or according to a combination thereof with an ordinary method.

The compound (I-B) thus obtained may be subjected to isolation and purification by means of known separation/purification means such as concentration, concentration in vacuo, crystallization, extraction with solvent, re-precipitation and chromatography.

Furthermore, a compound (I-C) according to an embodiment of the present invention may be produced, for example, by the following process:

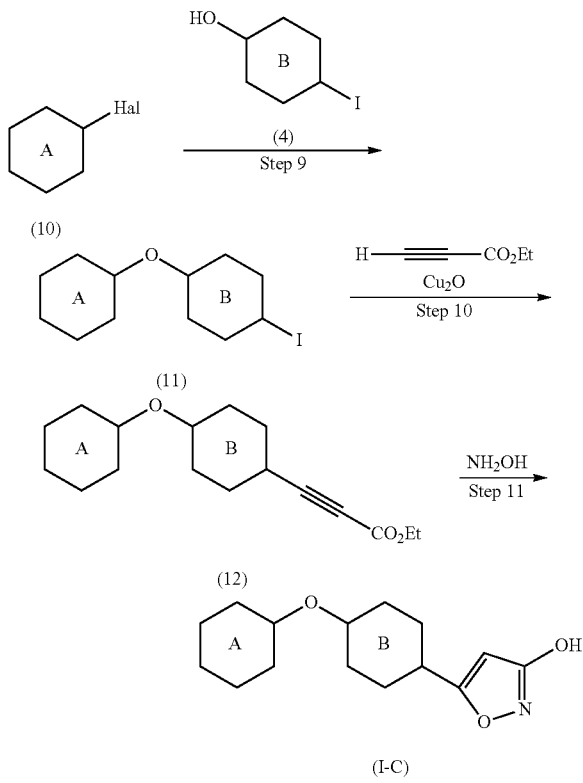

wherein Hal represents a halogen atom; and the other symbols have the same definitions specified above.

(Step 9)

This step is a process for producing a compound (11) by reacting a compound (10) with the compound (4) in the presence of a base.

Bases used in this step include, for example, sodium hydride and potassium carbonate.

An amount of the base used in this step is generally 1-100 equivalents, preferably 1-5 equivalents, relative 1 equivalent of the compound (10).

Compounds (10) used in this step include, for example, 2-chloro-1-fluoro-4-trifluoromethyl)benzene and the like. As the compounds (4) used in this step, ones as in the step 5 may be used.

An amount of the compound (4) used in this step is generally 1-100 equivalents, preferably 1-5 equivalents, relative 1 equivalent of the compound (10).

The reaction time in this step is generally 0.1-24 hours, preferably 0.5-5 hours.

The reaction temperature in this step is generally 0-200° C., preferably 50-120° C.

Reaction solvents used in this step, but, unless interfering with the reaction, are not limited to, e.g., dimethylsulfoxide and dimethylformamide.

The compound (11) thus obtained may be subjected to the next step with or without isolation and purification by means of known separation/purification means such as concentration, concentration in vacuo, crystallization, extraction with solvent, re-precipitation and chromatography.

(Step 10)

This step is a process for producing a compound (12) by reacting the compound (11) with ethyl propionate in the presence of copper (II) oxide.

The reaction in this step may be carried out in the same manner as in the above step 3, or according to a method similar to it, or according to a combination thereof with an ordinary method.

The compound (12) thus obtained may be subjected to the next step with or without isolation and purification by means of known separation/purification means such as concentration, concentration in vacuo, crystallization, extraction with solvent, re-precipitation and chromatography.

(Step 11)

This step is a process for producing a compound (I-C) according to an embodiment of the present invention by reacting a compound (12) with hydroxyamine in the presence of a base.

The reaction in this step may be carried out in the same manner as in the above step 2, or according to a method similar to it, or according to a combination thereof with an ordinary method.

The compound (I-C) thus obtained may be subjected to isolation and purification by means of known separation/purification means such as concentration, concentration in vacuo, crystallization, extraction with solvent, re-precipitation and chromatography.

Compounds of the present invention may exist as their pharmaceutically acceptable salts, and the salts may be produced from the compounds (I) and the compounds of the above-mentioned formula (I-1) or (I-2) which is within the scope of the compounds (I) of the invention in an ordinary method.

The acid-addition salts include, for example, hydrohalides such as hydrochlorides, hydrofluorides, hydrobromides, hydroiodides; inorganic acid salts such as nitrates, perchlorates, sulfates, phosphates, carbonates; lower alkylsulfonates such as methanesulfonates, trifluoromethanesulfonates, ethanesulfonates; arylsulfonates such as benzenesulfonates, p-toluenesulfonates; organic acid salts such as fumarates, succinates, citrates, tartrates, oxalates, maleates; other organic acid-addition salts with amino acid such as glutamates, aspartates.

When the compounds of the invention have an acid group in the molecule, for example, when they have a carboxyl group, then the compounds may be processed with a base so as to convert them into the corresponding pharmaceutically-acceptable salts. The base-addition salts include, for example, alkali metal salts with sodium or potassium; alkaline earth metal salts with calcium or magnesium; ammonium salts; organic base-addition salts with guanidine, triethylamine, dicyclohexylamine, etc Furthermore, the compounds of the invention may also be in any other form of hydrates or solvates of their free compounds or their salts.

In contrast, a salt or ester can be also converted into a free compound by an ordinary method.

Depending on the type of the substituents therein, the compounds of the invention include stereoisomers and tautomers such as optical isomers, diastereomeric isomers and geometrical isomers. Needless-to-say, the compounds of the invention include all these isomers. Further needless-to-say, the compounds of the invention include all mixtures of such isomers.

In producing medicines for prevention and remedy for type II diabetes or diseases or symptoms associated with it, the compounds of formula (I) of the invention may be combined with carrier.

The dose of the compounds of formula (I) of the invention for prevention or remedy for diseases naturally varies, depending on the property of the symptom to which the treatment is directed, the specific compound selected for it and the administration route.

The dose also varies depending on the age, the body weight and the sensitivity of patients.

In general, the daily dose for one-time or plural-times administration may be from about 0.001 mg/kg-body weight to about 100 mg/kg-body weight, preferably from about 0.01 mg/kg-body weight to about 50 mg/kg-body weight, even more preferably from about 0.1 mg/kg-body weight to about 10 mg/kg-body weight. As the case may be, administration of a dose over the range may be necessary.

An example of a suitable dose for oral administration is described. The daily dose for one-time or two- to four-times administration may be at least from about 0.01 mg to at most 2.0 g. Preferably, the daily administration frequency is once or twice a day, and the daily dose is from about 1.0 mg to about 200 mg. More preferably, the daily dose is from about 10 mg to 100 mg for one-time administration a day.

For intravenous administration or oral administration, a typical dose of the compound (I) may be from about 0.001 mg/day/kg-body weight to about 100 mg/day/kg-body weight (preferably from 0.01 mg/day/kg-body weight to about 10 mg/day/kg-body weight), more preferably from about 0.1 mg/day/kg-body weight to 10 mg/day/kg-body weight.

As so mentioned hereinabove, the pharmaceutical composition of the invention comprises a compound of formula (I) and a pharmaceutically-acceptable carrier. The term "composition" is meant to contain not only a product produced by directly or indirectly combining, hybridizing or aggregating 2 or more ingredients, a product produced as a result of dissociation of one or more ingredients, or a compound produced as a result of reaction or interaction of different types of ingredients, but also an active and inactive ingredient of constituting a carrier (pharmaceutically-acceptable vehicle).

As combined with a pharmaceutically-acceptable carrier, the composition of the invention preferably contains a compound of formula (I) in an amount effective for remedy and prevention of type II diabetes and for retardation of the onset of the disease.

For administering the effective dose of the compound of the invention to mammals, especially to humans, employable is any suitable administration route. For example, the route may be oral administration, rectal administration, local administration, intravenous administration, ophthalmic administration, lung administration or nasal administration. Examples of the administration forms are tablets, troches, powders, suspensions, solutions, capsules, creams, aerosols. Preferred are oral tablets.

In preparing oral compositions, usable are any ordinary pharmaceutical media. Their examples are water, glycol, oil, alcohol, fragrant additives, preservatives, colorants. In preparing liquid compositions for oral administration, for example, mentioned are suspensions, elixirs and solutions. Their carriers are, for example, starch, sugar, microcrystalline cellulose, diluent, granulating promoter, lubricant, binder, disintegrator. In preparing solid compositions for oral administration, for example, mentioned are powders, capsules and tablets. Above all, such solid compositions for oral administration are preferred.

In view of the easiness in their administration, tablets and capsules are the most advantageous forms for oral administration. If desired, the tablets may be coated according to standard aqueous or non-aqueous coating techniques.

In addition to the above-mentioned ordinary administration modes for them, the compounds of formula (I) may also be administered according to controlled release systems and/or controlled delivery systems, for example, as in U.S. Pat. Nos. 3,845,770, 3,916,899, 3,536,809, 3,598,123, 3,630,200 and 4,008,719.

The pharmaceutical composition of the invention suitable for oral administration includes capsules, cashews and tablets that contain a predetermined amount of the active ingredient in the form of powders or granules thereof, or in the form of water-soluble liquids, water-insoluble liquids, oil-in-water emulsions or water-in-oil emulsions thereof. These compositions may be prepared in any pharmaceutical methods, and all the methods include a process of combining the active ingredient with a carrier of one or more necessary ingredients.

In general, the active ingredient is uniformly and fully mixed with a liquid carrier, or a well-separated solid carrier or with both the two, and then, if desired, the product is shaped into suitable forms to prepare the composition. For example, tablets are produced through compression and shaping, optionally along with one or more side components. Using a suitable machine, compressed tablets may be produced by mixing the active ingredient optionally with binder, lubricant, inert vehicle, surfactant or dispersant and compressing the resulting mix in any desired manner into powders or granules.

Shaped tablets may be prepared by shaping a mixture of a powdery wet compound and an inert liquid diluent, using a suitable machine.

Preferably, the tablets each contain from about 1 mg to 1 g of the active ingredient; and the cashews and the capsules each contain from about 1 mg to 500 mg of the active ingredient.

Examples of the administration modes of the compounds of formula (I) for pharmaceutical use are as follows:

TABLE 1

| Suspension for Injection (I.M.) | mg/ml |
|---|---|
| compound of formula (I) | 10 |
| methyl cellulose | 5.0 |
| Tween 80 | 0.5 |
| benzyl alcohol | 9.0 |
| benzalkonium chloride | 1.0 |
| water for injection added to make 1.0 ml | |

TABLE 2

| Tablets | mg/tablet |
|---|---|
| compound of formula (I) | 25 |
| methyl cellulose | 415 |
| Tween 80 | 14.0 |
| benzyl alcohol | 43.5 |
| magnesium stearate | 2.5 |
| total | 500 mg |

TABLE 3

| Capsules | mg/capsule |
|---|---|
| compound of formula (I) | 25 |
| lactose powder | 573.5 |
| magnesium stearate | 1.5 |
| total | 600 mg |

TABLE 4

| Aerosol | per one container |
|---|---|
| compound of formula (I) | 24 mg |
| lecithin, NF Liq. Conc. | 1.2 mg |
| trichlorofluoromethane, NF | 4.025 g |
| dichlorodifluoromethane, NF | 12.15 g |

The compounds of formula (I) may be used, as combined with any other drugs usable not only for type II diabetes-associated diseases or symptoms but also for remedy/prevention/retardation of the onset of type II diabetes. The additional drugs may be administered in any administration route and dose generally employed in the art, simultaneously with or separately from the compound of formula (I).

In case where the compound of formula (I) is used along with one or more other drugs, then a pharmaceutical composition comprising the compound of formula (I) and the additional drug is preferred. Accordingly, the pharmaceutical composition of the invention may comprise not only the compound of formula (I) but also one or more such active ingredients. Examples of the active ingredients that may be combined with the compounds of formula (I) are mentioned below, which, however, are not limitative. These may be separately administered or may be administered simultaneously as contained in the same pharmaceutical composition.

(a) other GPR120 agonist,
(b) glucokinase activators,
(c) bis-guanides (e.g., buformin, metoformin, fenformin),
(d) PPAR agonists (e.g., triglytazone, pioglytazone, rosiglytazone),
(e) insulin,
(f) somatostatin,
(g) α-glucosidase inhibitors (e.g., boglybose, miglytol, acarbose),
(h) insulin secretion promoters (e.g., acetohexamide, calbutamide, chlorpropamide, glybomlide, glycrazide, glymerpiride, glypidide, glyquidine, glysoxepide, glyburide, glyhexamide, glypinamide, fenbutamide, trazamide, tolbutamide, tolcyclamide, nateglynide, repaglynide),
(i) DPP-IV (dipeptidyl peptidase IV) inhibitors, and The weight ratio of the compound of formula (I) to the second active ingredient may vary within a broad range, and depends on the effective amount of the individual active ingredients. Accordingly, for example, when the compound of formula (I) is combined with a PPAR agonist, then the weight ratio of the compound of formula (I) to the PPAR agonist may be generally from about 1000/1 to 1/1000, preferably from about 200/1 to 1/200. The combination of the compound of formula (I) and the other active ingredient may be within the above-mentioned range. In any case, an effective amount of the individual ingredients should be in the combination.

The compound according to an embodiment of the present invention has a GPR120 function regulating action, wherein "GPR120 function regulating action" means activation or suppression of the function of a GPR120 receptor. For example, a GPR120 agonist is also included in compounds having the GPR120 function regulating action.

A compound according to an embodiment of the present invention or a pharmaceutically acceptable salt thereof has a GPR120 function regulating action, particularly a GPR120 agonist action, and is useful for treating and/or preventing diabetes mellitus or hyperlipidemia.

It should be understood by those skilled in the art that various modifications, combinations, sub-combinations and alterations may occur depending on design requirements and other factors insofar as they are within the scope of the appended claims or the equivalents thereof.

EXAMPLES

The present invention is described below in more detail referring to Formulation Examples, Examples and Reference Examples, but is not limited thereto.

Formulation Example 1

Ten parts of the compound in accordance with Example 1, 15 parts of heavy magnesium oxide and 75 parts of lactose were blended uniformly to prepare a powder having a particle size of 350 μm or less in powder or granular form. The powder was charged in a capsule container to form a capsule.

Formulation Example 2

After uniformly blending 45 parts of the compound in accordance with Example 1, 15 parts of starch, 16 parts of lactose, 21 parts of crystalline cellulose, 3 parts of polyvinylalcohol and 30 parts of distilled water, the blend was crushed into granules, which were dried and then sieved to form granules having a particle diameter of 177-1410 μm.

Formulation Example 3

After preparing granules in the same manner as in Formulation Example 2, 3 parts of calcium stearate was added to 96 parts of the granules, and the mixture was compression-molded to prepare tablets having a diameter of 10 mm.

Formulation Example 4

To 90 parts of the granules prepared by the method described in Formulation Example 2 was added 10 parts of crystalline cellulose and 3 parts of calcium stearate, and the mixture was compression-molded to form tablets having a diameter of 8 mm, to which a syrup gelatin/precipitated calcium carbonate suspension was added to prepare sugar-coated tablets.

Wakogel (registered trademark) C-300, made by Wako Pure Chemical Industries Ltd., or KP-Sil (Registered Trademark) Silica prepacked column, made by Biotage, was used for the silica gel column chromatography in Examples. Kieselgel™ 60 $F_{254}$, Art. 5744, made by Merck & Co., was used for preparative thin layer chromatography. Chromatorex (registered trademark) NH (100-250 mesh or 200-350 mesh), made by Fuji Silysia Chemical Ltd., was used for basic silica gel column chromatography.

$^1$H-NMR was measured using Gemini (200 MHz, 300 MHz), Mercury (400 MHz) and Inova (400 MHz), made by Varian, using tetramethylsilane as a standard substance. In addition, the mass spectra were measured by electrospray ionization (ESI) or atmospheric pressure chemical ionization (APCI) using Micromass ZQ made by Waters.

The meanings of the abbreviations in Examples are shown below.
i-Bu=isobutyl
n-Bu=n-butyl
t-Bu=tert-butyl
Boc=tert-butoxycarbonyl
Me=methyl
Et=ethyl
Ph=phenyl
i-Pr=isopropyl
n-Pr=n-propyl
$CDCl_3$=heavy chloroform
$CD_3OD$=heavy methanol
DMSO-$d_6$=heavy dimethylsulfoxide The meanings of the abbreviations in the nuclear magnetic resonance spectra are shown below.
s=singlet
d=doublet
dd=double doublet
dt=double triplet
ddd=double double doublet
Sept=septet
t=triplet
m=multiplet
br=broad
brs=broad singlet
q=quartet
J=coupling constant
Hz=hertz Reference Example 1 ethyl 3-(4-hydroxyphenyl)-2-propinoate

To a solution of 4-iodophenol (22.3 g) in dimethylformamide (200 ml) were added 19.5 ml of ethyl propiolate and 14.8 g of copper (I) oxide, and the reaction solution was stirred at 110° C. for 15 hours. The reaction solution was cooled and then filtered through Celite, and the filtrate was vacuum-concentrated. The residue obtained was purified by silica gel column chromatography (eluent: hexane/ethyl acetate (4:1)), followed by recrystallization of the purified residue with hexane/ethyl acetate to afford the title compound as a white solid.

$^1$HNMR (400 MHz, $CDCl_3$) δ: 1.36 (3H, t, J=7.2 Hz), 4.30 (2H, q, J=7.2 Hz), 5.86-6.25 (1H, brm), 6.84 (2H, d, J=8.5 Hz), 7.46 (2H, d, J=8.5 Hz)
ESI-MS Found: m/z 191.1[M+H]+

Reference Example 2 ethyl 3-(4-(hydroxymethyl)phenyl)-2-propinoate

Using 4-iodophenyl methanol, the title compound was obtained as a brown oil by the same method as in Example 1 or in accordance with the method or by combining it with an ordinary method.

$^1$HNMR (400 MHz, $CDCl_3$) δ: 1.37 (3H, q, J=7.3 Hz), 1.99-2.14 (1H, brm), 4.29 (2H, q, J=7.3 Hz), 4.73 (2H, s), 7.37 (2H, d, J=7.9 Hz), 7.57 (2H, d, J=7.9 Hz)
ESI-MS Found: m/z 205.2[M+H]+

Reference Example 3 ethyl 3-(4-(2-hydroxyethyl)phenyl)-2-propinoate

Using 2-(4-iodophenyl)ethanol, the title compound was obtained as a brown oily by the same method as in Example 1 or in accordance with the method or by combining it with an ordinary method.

$^1$HNMR (400 MHz, $CDCl_3$) δ: 1.36 (3H, t, J=7.0 Hz), 2.88 (2H, t, J=6.3 Hz), 3.85-3.91 (2H, m), 4.31 (2H, q, J=7.0 Hz), 7.25 (2H, d, J=8.0 Hz), 7.54 (2H, d, J=8.0 Hz)
ESI-MS Found: m/z 219.2[M+H]+

Reference Example 4

2-fluoro-4-iodophenol

1) Production of 2-fluoro-4-nitrophenylacetate

To a solution of 4-fluoro-2-nitrophenol (10 g) in pyridine (10 ml), 10 ml of acetic anhydride was added, and the reaction solution was stirred overnight at room temperature. To the reaction solution, 100 ml of 5% aqueous hydrochloric acid solution was added, and the reaction solution was stirred at room temperature for 30 minutes. The reaction solution was extracted with chloroform, and the combined organic layers were washed with 5% aqueous hydrochloric acid solution. The organic phase was dried over anhydrous magnesium sulfate, and the solvent was distilled off under reduced pressure. The residue obtained was purified by silica gel column chromatography (eluent: ethyl acetate/hexane (15:85-3:7)) to afford the title compound as a yellow oil.

2) Production of 4-amino-2-fluorophenylacetate

To a solution of 2-fluoro-4-nitrophenylacetate (2.30 g) in ethyl acetate (20 ml), 200 mg of 10% palladium-carbon catalyst was added, and the reaction solution was stirred overnight at room temperature under hydrogen atmosphere. The reaction solution was filtered through Celite, and the filtrate was concentrated under reduced pressure. The residue obtained was purified by silica gel column chromatography (eluent: ethyl acetate/hexane (0:1-2:1)) to afford the title compound as a brown oil.

3) Production of 2-fluoro-4-iodophenylacetate

To a mixed solution of 4-amino-2-fluorophenylacetate (1.0 g) in concentrated hydrochloric acid (4.3 g) and water (50 ml), an aqueous solution (2 ml) of sodium nitrite (500 mg) was added at −2 to −3° C. The reaction solution was further stirred at the same temperature for 30 minutes, followed by adding an aqueous solution (10 ml) of potassium iodide (4.9 g). The reaction solution was stirred at the same temperature for 20 minutes, then the temperature of the reaction solution was allowed to warm to room temperature, and the reaction solution was stirred for 2.5 hours. Sodium hydrogen sulfite was added to the reaction solution till the color of the reaction solution becomes yellow, extracted with diethyl ether, and dried over anhydrous magnesium sulfate. The solvent was distilled off under reduced pressure, and the residue obtained was purified by silica gel column chromatography (eluent: ethyl acetate/hexane (0:1-1:3)) to afford the title compound as a colorless oil.

4) Production of 2-fluoro-4-iodophenol

To a solution of 2-fluoro-4-iodophenylacetate (500 mg) in methanol (3 ml) was added 1.07 ml of 2N aqueous sodium hydroxide. The reaction solution was stirred at room temperature for 40 minutes, followed by vacuum concentration of the reaction solution. The residue obtained was diluted with water, acidified with 10% aqueous citric acid to pH 4, then extracted with ethyl acetate, and dried over anhydrous magnesium sulfate. The solvent was distilled off under reduced pressure to afford the title compound as a colorless oil.
$^1$HNMR (400 MHz, CDCl$_3$) δ: 5.26 (1H, s), 6.77 (1H, t, J=8.8 Hz), 7.30-7.36 (1H, m), 7.39 (1H, d d, J=1.8, 9.8 Hz)
ESI-MS Found: m/z 237.0[M+H]+

Reference Example 5

4-(3-(methoxymethoxy)-5-isoxazolyl)phenol

1) Production of ethyl 3-(4-(benzyloxy)phenyl)-2-propinoate

To a solution of ethyl 3-(4-hydroxyphenyl)-2-propinoate (1.02 g) in acetone (25 ml) obtained in Reference Example 1, 3.69 g of potassium carbonate and 0.64 ml of benzyl bromide were added, and the reaction solution was stirred at 65° C. for 4 hours. The reaction solution was cooled, water was added to the cooled reaction solution, and then the mixture was extracted with chloroform and dried over anhydrous sodium sulfate. The solvent was distilled off under reduced pressure, and the residue obtained was purified by silica gel column chromatography (eluent: ethyl acetate/hexane (10:90-50:50)) to afford the title compound as a white solid.

2) Production of 5-(4-(benzyloxy)phenyl)isoxazol-3-ol

To a solution of ethyl 3-(4-(benzyloxy)phenyl)-2-propinoate (1.46 g) in methanol (30 ml), 1.45 g of hydroxyamine hydrochloride and 6.25 ml of 5M potassium hydroxide methanol were added, and the reaction solution was stirred overnight at room temperature. The solvent was distilled off under reduced pressure, the residue obtained was suspended in water, and the suspension was adjusted to pH 2-3 with a 2N aqueous hydrochloric acid solution. The resultant solid was obtained by filtration to afford the title compound as a light brown solid.

3) Production of 5-(4-(benzyloxy)phenyl)-3-(methoxymethoxy)isoxazole

To a solution of 5-(4-(benzyloxy)phenyl)isoxazol-3-ol (1.38 g) in tetrahydrofuran (30 ml), 2.15 ml of triethylamine and 0.51 ml of methoxymethyl chloride were added, and the reaction solution was stirred overnight at room temperature. A saturated aqueous ammonium chloride solution was added to the reaction solution, and the mixture was extracted with ethyl acetate. The combined organic layers were washed with a saturated saline solution and dried over anhydrous sodium sulfate. The solvent was distilled off under reduced pressure, and the residue obtained was purified by silica gel column chromatography (eluent: ethyl acetate/hexane (10:90-0:100)) to afford the title compound as a light brown solid.

4) Production of 4-(3-(methoxymethoxy)isoxazol-5-yl)phenol

To a mixed solution of 5-(4-(benzyloxy)phenyl)-3-(methoxymethoxy)isoxazole (1.44 g) in methanol (15 ml) and tetrahydrofuran (15 ml), 200 mg of 10% palladium-carbon catalyst was added, and the reaction solution was stirred overnight at room temperature under hydrogen atmosphere. The reaction solution was filtered through Celite, the solvent was distilled off under reduced pressure, and the residue obtained was purified by silica gel column chromatography (eluent: ethyl acetate/hexane (10:90-50:50)) to afford the title compound as a pale yellow solid.
$^1$HNMR (400 MHz, CDCl$_3$) δ: 3.58 (3H, s), 5.35 (2H, s), 6.11 (1H, s), 6.40 (1H, brs), 6.92-6.96 (2H, m), 7.61-7.64 (2H, m)
ESI-MS Found: m/z 222.2[M+H]+

Reference Example 6

Production of 5-(4-hydroxyphenyl)isoxazol-3-ylpivalate

1) Production of 5-(4-(benzyloxy)phenyl)isoxazol-3-ylpivalate

To a solution of 5-(4-(benzyloxy)phenyl)isoxazol-3-ol (4.39 g) obtained in Reference Example 5 (Step 2) in chloroform (80 ml), 6.8 ml of triethylamine and 3.7 ml of pivaloyl chloride were added, and the reaction solution was stirred at room temperature for 1 hour. The reaction solution was diluted with a saturated aqueous ammonium chloride solution, extracted with chloroform, and dried over anhydrous sodium sulfate. The solvent was distilled off under reduced pressure, the residue obtained was suspended in ether, hexane was added, and the resultant solid was obtained by filtration to afford the title compound as a light brown solid.

2) Production of 5-(4-hydroxyphenyl)isoxazol-3-ylpivalate

The title compound was obtained as a pale yellow solid by the same method as in Reference Example 5 (Step 4) using 5-(4-(benzyloxy)phenyl)isoxazol-3-ylpivalate.
$^1$HNMR (400 MHz, CDCl$_3$) δ: 1.38 (9H, s), 6.16 (1H, brs), 6.51 (1H, s), 6.91-6.94 (2H, m), 7.61-7.65 (2H, m)
ESI-MS Found: m/z 262.2[M+H]+

Example 1

5-(4-((2-(cyclopentyloxy)pyridin-3-yl)methoxy)phenyl)isoxazol-3-ol

1) Production of (2-(cyclopentyloxy)pyridin-3-yl)methanol

To a solution of methyl 2-hydroxynicotinate (300 mg) in dimethylformamide (3 ml), 0.42 ml of bromocyclopropane and 542 mg of potassium carbonate were added, and the reaction solution was stirred overnight at 50° C. The reaction solution was cooled, then diluted with a saturated aqueous ammonium chloride solution, and extracted with ethyl acetate. The combined organic layers were washed with a saturated saline solution and dried over anhydrous sodium sulfate. The solvent was distilled off under reduced pressure to afford a crude product as a yellow oil. To a solution of lithium aluminum hydride (143 mg) in tetrahydrofuran (2 ml), a solution of the crude product in tetrahydrofuran 3 ml was added under ice-cooling. The reaction solution was stirred at the same temperature for 1 hour, followed by adding sodium sulfate decahydrate and further stirring the mixture at the same temperature for 1 hour. The reaction solution was Celite-filtered, the filtrate was distilled off under reduced pressure, and the residue obtained was purified by silica gel column chromatography (eluent: hexane/ethyl acetate (95:5-50:50)) to afford the title compound as a colorless oil.

2) Production of 5-(4-((2-(cyclopentyloxy)pyridin-3-yl)methoxy)phenyl)isoxazol-3-ol To a solution of (2-(cyclopentyloxy)pyridin-3-yl)methanol (103 mg) in tetrahydrofuran (2 ml), 132 mg of ethyl 3-(4-hydroxyphenyl)-2-propinoate obtained in Reference Example 1, 280 mg of triphenylphosphine, and 0.485 ml of azodicarboxylic acid diethyl ester (2.2M toluene solution) were added under ice-cooling, and the reaction solution was stirred at room temperature for 1 hour. An excessive amount of methanol was added, then the solvent was distilled off under reduced pressure, and the residue obtained was purified by silica gel column chromatography (eluent: hexane/ethyl acetate (98:2-50:50)) to afford a crude product as a colorless oil. To a mixed solution of crude product obtained (203 mg) in tetrahydrofuran (1 ml) and ethanol (0.5 ml), 0.1 ml of hydroxylamine (50% aqueous solution) and 0.64 ml of 2.5N aqueous sodium hydroxide were added, the reaction solution was stirred overnight at room temperature. A 10% aqueous citric acid was added to the reaction solution, and the mixture was extracted with chloroform. The organic layer was dried over anhydrous sodium sulfate, then the solvent was distilled off under reduced pressure, and the residue obtained was purified through reversed phase medium pressure liquid chromatography [ODS-AS-360-CC (by YMC), mobile phase: water-acetonitrile-0.1% trifluoroacetic acid]. The solvent was distilled off under reduced pressure, the residue obtained was diluted with chloroform and washed with a saturated saline solution, and the organic layer was dried over anhydrous sodium sulfate. The solvent was distilled off under reduced pressure to afford the title compound as a white solid.

$^1$HNMR (400 MHz, CD$_3$OD) δ: 1.64 (2H, m), 1.79-1.82 (4H, m), 1.95 (2H, m), 5.08 (2H, s), 6.17 (1H, s), 6.92-6.95 (1H, m), 7.07 (2H, d, J=8.6 Hz), 7.70 (2H, d, J=8.6 Hz), 7.75-7.76(1H, m), 7.90 (1H, s), 8.07 (1H, d, J=3.7 Hz)

ESI-MS Found: m/z 353.1[M+H]+

Example 2

5-(4-((2-isopropoxypyridin-3-yl)methoxy)phenyl)isoxazol-3-ol

1) Production of methyl 2-hydroxynicotinate

To a solution of 2-hydroxynicotinic acid (3.0 g) in methanol 15 ml, 1 ml of concentrated sulfuric acid was added, and the reaction solution was heated to reflux for 2 hours. The reaction solution was cooled, then the solvent was distilled off under reduced pressure, and the residue obtained was diluted with water and extracted with chloroform. The combined organic layers were washed with a saturated aqueous sodium bicarbonate solution and dried over anhydrous sodium sulfate. The solvent was distilled off under reduced pressure to afford the title compound as a pale pink solid.

2) Production of (2-isopropoxypyridin-3-yl)methanol

To a solution of methyl 2-hydroxynicotinate (250 mg) in dimethylformamide (3 ml), 0.459 ml of 2-bromopropane and 676 mg of potassium carbonate were added, and the reaction solution was stirred at 50° C. for 5 hours and at 70° C. for 3 hours. The reaction solution was cooled, then a saturated aqueous ammonium chloride solution was added, and the mixture was extracted with ethyl acetate. The combined organic layers were washed with a saturated saline solution and dried over anhydrous sodium sulfate. The solvent was distilled off under reduced pressure to afford a crude product as a colorless oil. To a solution of lithium aluminum hydride (247 mg) in tetrahydrofuran (2 ml), a solution of the crude product in tetrahydrofuran 3 ml was added under ice-cooling. The reaction solution was stirred for 2 hours under ice-cooling, followed by adding sodium sulfate decahydrate and further stirring the mixture at the same temperature for 1 hour. The reaction solution was Celite-filtered, the filtrate was distilled off under reduced pressure, and the residue obtained was purified by silica gel column chromatography (eluent: hexane/ethyl acetate (98:2-50:50)) to afford the title compound as a colorless oil.

3) Production of ethyl 3-(4-((2-isopropoxypyridin-3-yl)methoxy)phenyl)prop-2-enoate To a solution of (2-isopropoxypyridin-3-yl)methanol (106 mg) in ethyl acetate (1.5 ml), 0.176 ml of triethylamine and 0.1 ml of methanesulfonyl chloride were added under ice-cooling, and the reaction solution was stirred for 30 minutes. A saturated saline solution was added to the reaction solution, and the mixture was extracted with ethyl acetate. The combined organic layers were washed with a saturated saline solution and then dried over anhydrous sodium sulfate, and the solvent was distilled off under reduced pressure to afford a crude product. To a solution of the resultant crude product in dimethylformamide (2 ml), ethyl 3-(4-hydroxyphenyl)-2-propinoate (181 mg) obtained in Reference Example 1 and sodium hydride (51 mg) were added under ice-cooling, and the reaction solution was stirred at room temperature for 1 hour. A 10% aqueous citric acid was added to the reaction solution, followed by extracting the mixture with ethyl acetate. The combined organic layers were washed with a saturated saline solution and dried over anhydrous sodium sulfate. The solvent was distilled off under reduced pressure, and the residue obtained was purified by silica gel column chromatography (eluent: hexane/ethyl acetate (98:2-50:50)) to afford the title compound as a colorless oil.

4) Production of 5-(4-((2-isopropoxypyridin-3-yl)methoxy)phenyl)isoxazol-3-ol

To a mixed solution of 3-(4-((2-isopropoxypyridine)-3-yl)methoxy)phenyl)propynoic acid ethyl (126 mg) in tetrahydrofuran (1 ml) and ethanol (0.5 ml), 0.066 ml of hydroxylamine (50% aqueous solution) and 0.445 ml of 2.5N aqueous sodium hydroxide were added, and the reaction solution was stirred overnight at room temperature. A 10% aqueous citric acid was added to the reaction solution, and the mixture was extracted with chloroform and dried over anhydrous sodium sulfate. The solvent was distilled off under reduced pressure, and the residue obtained was purified by silica gel column chromatography (eluent: chloroform/methanol (99:1-90:10)) to afford the title compound as a pale yellow solid.

$^1$HNMR (400 MHz, DMSO-$d_6$) δ: 1.30 (6H, d, J=6.3 Hz), 5.09 (2H, s), 5.31-5.33 (1H, m), 6.41 (1H, s), 6.98-6.99 (1H, m), 7.13 (2H, d, J=8.8 Hz), 7.73-7.79 (3H, m), 8.14 (1H, s), 11.28 (1H, s)

ESI-MS Found: m/z 327.3[M+H]+

Example 3

5-(4-((6-phenoxypyridin-2-yl)methoxy)phenyl)isoxazol-3-ol

1) Production of 2-((4-iodophenoxy)methyl)-6-phenoxypyridine

To a solution of (6-phenoxypyridin-2-yl)methanol (100 mg) in ethyl acetate (4 ml), triethylamine (0.103 ml) and methanesulfonyl chloride (0.062 ml) were added under ice-cooling, the reaction solution was stirred at the same temperature for 1 hour. The reaction solution was diluted with ethyl acetate, washed with water, and dried over anhydrous magnesium sulfate. The solvent was distilled off under reduced pressure to afford a crude product as a brown oil. To a solution of 4-iodophenol in dimethylformamide (1 ml), 24 mg of sodium hydride was added under ice-cooling, and the reaction solution was stirred at room temperature for 1 hour. The reaction solution was cooled to 0° C., a solution of the crude product in dimethylformamide (1 ml) was added, and the reaction solution was stirred at room temperature for 2 hours. The reaction solution was diluted with a saturated saline solution, extracted with diethyl ether, and dried over anhydrous magnesium sulfate. The solvent was distilled off under reduced pressure, and the residue obtained was purified by silica gel column chromatography (eluent: ethyl acetate/hexane (0:100-20:80)) to afford the title compound as a white solid.

2) Production of ethyl 3-(4-((6-phenoxypyridin-2-yl)methoxy)phenyl)prop-2-enoate To a solution of 2-((4-iodophenoxy)methyl)-6-phenoxypyridine (160 mg) in dimethylformamide (2 ml), 0.116 ml of ethyl propiolate and 69 mg of copper (II) oxide were added, and the reaction solution was stirred at 110° C. for 15 hours. The reaction solution was cooled and then Celite-filtered, and the filtrate was distilled off under reduced pressure. The residue obtained was purified by silica gel column chromatography (eluent: hexane/ethyl acetate (0:100-20:80-33/67)) to afford the title compound as a colorless oil.

3) Production of 5-(4-((6-phenoxypyridin-2-yl)methoxy)phenyl)isoxazol-3-ol

To a solution of ethyl 3-(4-((6-phenoxypyridin-2-yl)methoxy)phenyl)prop-2-enoate (20.2 mg) in ethanol (1 ml), 0.05 ml of 50% aqueous hydroxylamine solution and 0.03 ml of 2N aqueous sodium hydroxide were added, and the reaction solution was stirred overnight at room temperature. The reaction solution was acidified with 10% aqueous citric acid, then extracted with chloroform, and dried over anhydrous magnesium sulfate. The solvent was distilled off under reduced pressure, and residue obtained was purified by preparative thin layer chromatography (Kieselgel™ 60 $F_{254}$, Art5744, made by Merck & Co., chloroform/methanol (8:1)) to afford the title compound as a white solid.

$^1$HNMR (400 MHz, CDCl$_3$) δ: 5.13 (2H, s), 6.09 (1H, brs), 6.76 (1H, d, J=8.3 Hz), 7.02 (2H, d, J=8.3 Hz), 7.15 (2H, d, J=8.0 Hz), 7.19-7.25 (2H, m), 7.41 (2H, t, J=8.0 Hz), 7.64-7.72 (3H, m)

ESI-MS Found: m/z 361.0[M+H]+

Example 4

5-(4-((5-phenylisoxazol-3-yl)methoxy)phenyl)isoxazol-3-ol

1) Production of (5-phenylisoxazol-3-yl)methanol

To a solution of 5-phenylisoxazol-3-carboxylic acid (551 mg) in tetrahydrofuran (15 ml), 3.7 ml of borane-tetrahydrofuran complex (1.17M tetrahydrofuran solution) was added, and the reaction solution was stirred at 80° C. for 10 hours. Water and a saturated aqueous sodium hydrogen carbonate solution were added to the reaction solution, and the mixture was extracted with chloroform and dried over anhydrous sodium sulfate. The solvent was distilled off under reduced pressure, and the residue obtained was purified by silica gel column chromatography (eluent: ethyl acetate/hexane (10:90-50:50)) to afford the title compound as a white solid.

2) Production of 5-(4-((5-phenylisoxazol-3-yl)methoxy)phenyl)isoxazol-3-ylpivalate To a solution of (5-phenylisoxazol-3-yl)methanol (25 mg) and 5-(4-hydroxyphenyl)isoxazol-3-ylpivalate (37 mg) obtained in Reference Example 6 in tetrahydrofuran (5 ml), 0.078 ml of diethyl azodicarboxylate (45% toluene solution) and 45 mg of triphenylphosphine were added, and the reaction solution was stirred overnight at room temperature. The solvent was distilled off under reduced pressure, and the residue obtained was purified by silica gel column chromatography (eluent: ethyl acetate/hexane (10:90-30:70)) to afford the title compound as a white solid.

3) Production of 5-(4-((5-phenylisoxazol-3-yl)methoxy)phenyl)isoxazol-3-ol

To a solution of 5-(4-((5-phenylisoxazol-3-yl)methoxy)phenyl)isoxazol-3-ylpivalate (21 mg) in methanol (2 ml), 0.4 ml of 5M potassium hydroxide methanol solution was added, and the reaction solution was stirred at room temperature for 1 hour. The reaction solution was neutralized, then extracted with chloroform, and dried over anhydrous sodium sulfate. The solvent was distilled off under reduced pressure, and the residue obtained was purified through reversed phase medium pressure liquid chromatography (ODS-AS-360-CC (by YMC), mobile phase: water-acetonitrile-0.1% trifluoroacetic acid). The solvent of the resultant fraction was distilled off under reduced pressure to afford the title compound as a white solid.

$^1$HNMR (400 MHz, CD$_3$OD) δ: 5.25 (2H, s), 6.00 (1H, s), 6.91 (1H, s), 7.10-7.14 (2H, m), 7.46-7.52 (3H, m), 7.66-7.69 (2H, m), 7.83-7.86 (2H, m)

ESI-MS Found: m/z 335.4[M+H]+

Example 5

5-(4-((2-(3-fluorophenoxy)pyridin-3-yl)methoxy)phenyl)isoxazol-3-ol

The title compound was obtained as a white solid by the same method as in Example 2 (Step 3 and 4) or in accordance with the method or by combining it with an ordinary method, using (2-(3-fluorophenoxy)pyridin-3-yl)methanol.

¹HNMR (400 MHz, DMSO-$d_6$) δ: 5.26 (2H, s), 6.38 (1H, s), 6.96-6.99 (1H, m), 7.01-7.07 (2H, m), 7.15 (2H, d, J=8.8 Hz), 7.19 (1H, dd, J=7.3, 5.0 Hz), 7.38-7.44 (1H, m), 7.72 (2H, d, J=8.8 Hz), 7.97 (1H, dd, J=7.3, 1.5 Hz), 8.10 (1H, dd, J=5.0, 1.5 Hz)

ESI-MS Found: m/z 379.3[M+H]+

Example 6

5-(4-((2-phenylpyridin-3-yl)methoxy)phenyl)isoxazol-3-ol

The title compound was obtained as a white solid by the same method as in Example 1 (Step 2) or in accordance with the method or by combining it with an ordinary method, using (2-phenyl-3-pyridinyl)methanol.

¹HNMR (400 MHz, DMSO-$d_6$) δ: 5.12 (2H, s), 6.40 (1H, s), 7.04 (2H, d, J=8.6 Hz), 7.40-7.75 (8H, m), 8.06 (1H, d, J=7.4 Hz), 8.68 (1H, d, J=4.7 Hz), 11.15-11.41 (1H, brm)

ESI-MS Found: m/z 345.2[M+H]+

Example 7

5-(3-fluoro-4-((2-phenoxypyridin-3-yl)methoxy)phenyl)isoxazol-3-ol

1) Production of (2-phenoxypyridin-3-yl)methanol

To a solution of 2-phenoxynicotinic acid (2.0 g) in tetrahydrofuran (20 ml), 9.5 ml of borane-tetrahydrofuran complex (1.17M tetrahydrofuran solution) was added, and the reaction solution was stirred overnight at 50° C. The reaction solution was cooled, 14 ml of 1N aqueous sodium hydroxide was added under ice-cooling, and the reaction solution was stirred for 1 hour. The reaction solution was diluted with saturated aqueous ammonium solution, extracted with diethyl ether, and dried over anhydrous magnesium sulfate. The solvent was distilled off under reduced pressure, and the residue obtained was purified by silica gel column chromatography (eluent: ethyl acetate/hexane (0:100-50:50)) to afford the title compound as a colorless oil.

2) Production of 5-(3-fluoro-4-((2-phenoxypyridin-3-yl)methoxy)phenyl)isoxazol-3-ol The title compound was obtained as a white solid by the same method as in Example 3 or in accordance with the method or by combining it with an ordinary method, using (2-phenoxypyridin-3-yl)methanol and 2-fluoro-4-iodophenol obtained in Reference Example 4.

¹HNMR (400 MHz, DMSO-$d_6$) δ: 5.37 (2H, s), 6.51 (1H, s), 7.07-7.25 (4H, m), 7.35-7.50 (3H, m), 7.60 (1H, d, J=8.4 Hz), 7.72 (1H, dd, J=12.1, 1.5 Hz), 7.98 (1H, dd, J=7.4, 1.5 Hz), 8.10 (1H, dd, J=4.9, 1.5 Hz)

ESI-MS Found: m/z 379.2[M+H]+

Example 8

5-(3-fluoro-4-((2-phenoxypyridin-3-yl)methoxy)phenyl)isoxazol-3-ol

The title compound was obtained as a white solid by the same method as in Example 5 or in accordance with the method or by combining it with an ordinary method, using (2-(2-fluorophenoxy)pyridin-3-yl)methanol.

¹HNMR (400 MHz, DMSO-$d_6$) δ: 5.31 (2H, s), 6.39 (1H, s), 7.16-7.20 (3H, m), 7.22-7.37 (4H, m), 7.73 (2H, d, J=8.8 Hz), 7.99 (1H, dd, J=7.4, 1.9 Hz), 8.06 (1H, dd, J=5.0, 1.9 Hz)

ESI-MS Found: m/z 379.3[M+H]+

Example 9

5-(6-((2-phenoxybenzyl)oxy)pyridin-3-yl)isoxazol-3-ol

1) Production of 5-iodo-2-((2-phenoxybenzyl)oxy)pyridine

To a solution of 2-chloro-5-iodopyridine in dimethylacetamide (2 ml), 300 mg of potassium tert-butoxy and 535 mg of (2-phenoxyphenyl)methanol were added, and the reaction solution was stirred at 110° C. for 4 hours. The reaction solution was cooled, then diluted with a saturated saline solution, extracted with diethyl ether, and dried over magnesium sulfate. The solvent was distilled off under reduced pressure, and the residue obtained was purified by silica gel column chromatography (eluent: ethyl acetate/hexane (0:100-10:90)) to afford the title compound as a white solid.

2) Production of 5-(6-((2-phenoxybenzyl)oxy)pyridin-3-yl)isoxazol-3-ol

The title compound was obtained as a white solid by the same method as in Example 3 or in accordance with the method or by combining it with an ordinary method, using 5-iodo-2-((2-phenoxybenzyl)oxy)pyridine.

¹HNMR (400 MHz, DMSO-$d_6$) δ: 5.42 (2H, s), 6.51 (1H, s), 6.89-6.98 (4H, m), 7.10 (1H, t, J=7.6 Hz), 7.19 (1H, t, J=7.6 Hz), 7.32-7.40 (3H, m), 7.58 (1H, d, J=7.6 Hz), 8.07 (1H, dd, J=8.5, 2.1 Hz), 8.59 (1H, d, J=2.1 Hz), 11.42 (1H, brs)

ESI-MS Found: m/z 361.3[M+H]+

Example 10

5-(5-((2-phenoxybenzyl)oxy)pyridin-2-yl)isoxazol-3-ol

1) Production of 2-bromo-5-((2-phenoxybenzyl)oxy)pyridine

To a solution of 6-bromopyridin-3-ol (1.76 g) in tetrahydrofuran (20 ml), 3.20 g of triphenylphosphine, 5.52 ml of diethyl azodicarboxylate (45% toluene solution) and 2.43 g of (2-phenoxyphenyl)methanol were added, and the reaction solution was stirred overnight at room temperature. The reaction solvent was distilled off under reduced pressure, and the residue obtained was purified by silica gel column chromatography (eluent: ethyl acetate/hexane (0:100-15:85)) to afford the title compound as a yellow oil.

2) Production of ethyl (2E)-3-(5-((2-phenoxybenzyl)oxy)pyridin-2-yl)acrylate

To a solution of 2-bromo-5-((2-phenoxybenzyl)oxy)pyridine (1.0 g) in dimethylformamide (7 ml), 1.26 g of ethyl (2E)-3-(tributylstannyl)acrylate and 350 mg of tetrakis triphenylphosphine palladium were added, and the reaction solution was stirred overnight at 100° C. under nitrogen atmosphere. The reaction solution was cooled, then 15 ml of a saturated aqueous potassium fluoride solution was added, and the reaction solution was stirred for 1 hour, followed by removing insoluble matters by filtration through Celite and the filtrate was concentrated under reduced pressure. The residue obtained was diluted with water, extracted with diethyl ether, and dried over magnesium sulfate. The solvent was distilled off under reduced pressure, and the residue obtained was purified by silica gel column chromatography (eluent: ethyl acetate/hexane (0:100-25:75-30:70)) to afford the title compound as a yellow solid.

3) Production of ethyl 2,3-dibromo-3-(5-((2-phenoxybenzyl)oxy)-2-pyridinyl)propanoate To a solution of ethyl (2E)-3-(5-((2-phenoxybenzyl)oxy)pyridin-2-yl)acrylate (200 mg) in carbon tetrachloride (3 ml), 0.027 ml of bromine was added, and the reaction solution was stirred at room temperature for 2 hours. The reaction solution was concentrated under reduced pressure, and the residue obtained was purified by silica gel column chromatography (eluent: ethyl acetate/hexane (8:92-30:70)) to afford the title compound as a colorless oil.

4) Production of 5-(5-((2-phenoxybenzyl)oxy)pyridin-2-yl)isoxazol-3-ol

To a solution of ethyl 2,3-dibromo-3-(5-((2-phenoxybenzyl)oxy)-2-pyridinyl)propanoate (159.3 mg) in tetrahydrofuran (1 ml), 32 mg of hydroxyamine hydrochloride, 0.6 ml of 2.5N sodium hydroxide/methanol solution and 0.078 ml of water were added, and the reaction solution was stirred at room temperature for 2 hours and then heated to reflux overnight. The reaction solution was cooled, then diluted with water, acidified with 10% aqueous citric acid, then extracted with chloroform, and dried over anhydrous magnesium sulfate. The solvent was distilled off under reduced pressure, and the residue obtained was purified through reversed phase medium pressure liquid chromatography (ODS-AS-360-CC (by YMC), mobile phase: water-acetonitrile-0.1% trifluoroacetic acid). The solvent of the resultant fraction was distilled off under reduced pressure, and then purification by preparative thin layer chromatography (Kieselgel™ 60 $F_{254}$, Art5744, made by Merck & Co., chloroform/methanol (9:1)) was carried out to afford the title compound as a white solid.
$^1$HNMR (400 MHz, DMSO-$d_6$) δ: 5.25 (2H, s), 6.41 (1H, s), 6.92 (1H, d, J=7.8 Hz), 6.97 (2H, d, J=7.8 Hz), 7.12 (1H, t, J=7.4 Hz), 7.21 (1H, t, J=7.4 Hz), 7.32-7.42 (3H, m), 7.56 (1H, dd, J=8.7, 2.8 Hz), 7.59-7.64 (1H, m), 7.79 (1H, d, J=8.7 Hz), 8.34 (1H, d, J=2.8 Hz), 11.21-11.63 (1H, m)
ESI-MS Found: m/z 361.1[M+H]+

Example 11

5-(4-((2-phenoxypyridin-4-yl)methoxy)phenyl)isoxazol-3-ol

1) Production of (2-bromopyridin-4-yl)methanol

To a solution of 2-bromoisonicotinic acid (678 mg) in tetrahydrofuran (30 ml), 8.4 ml of borane-tetrahydrofuran complex (1.17M tetrahydrofuran solution) was added, and the reaction solution was stirred overnight at room temperature. To the reaction solution was added 7.9 ml of 1N aqueous sodium hydroxide, and the mixture was stirred for 2 hours. The reaction solution was diluted with a saturated aqueous sodium chloride solution, extracted with diethyl ether, and dried over anhydrous magnesium sulfate. The solvent was distilled off under reduced pressure, and the residue obtained was purified by silica gel column chromatography (eluent: chloroform/(chloroform/methanol (9:1)) (100:0-0:100)) to afford the title compound as a white crystal.

2) Production of (2-phenoxypyridin-4-yl)methanol

At 190° C., (2-bromopyridin-4-yl)methanol (550 mg), phenol (330 mg) and potassium carbonate (450 mg) were stirred for 30 minutes. To the reaction solution was added 330 mg of phenol, and the mixture was stirred at the same temperature for further 30 minutes. To the reaction solution were added 700 mg of phenol and 450 mg of potassium carbonate, and the mixture was stirred at the same temperature for further 1 hour. The reaction solution was cooled, then diluted with water, extracted with ethyl acetate, and dried over anhydrous magnesium sulfate. The solvent was distilled off under reduced pressure, and the residue obtained was purified by silica gel column chromatography (eluent: ethyl acetate/hexane (0:100-100:0)) to afford the title compound as a brown oil.

3) Production of 5-(4-((2-phenoxypyridin-4-yl)methoxy)phenyl)isoxazol-3-ol

The title compound was obtained as a white solid by the same method as in Example 3 or in accordance with the method or by combining it with an ordinary method, using (2-phenoxypyridin-4-yl)methanol.
$^1$HNMR (400 MHz, CDCl$_3$) δ: 5.14 (2H, s), 6.11 (1H, s), 6.97-7.08 (4H, m), 7.14 (2H, d, J=7.5 Hz), 7.22 (1H, t, J=7.5 Hz), 7.41 (2H, t, J=7.9 Hz), 7.69 (2H, d, J=8.8 Hz), 8.21 (1H, d, J=5.3 Hz)
ESI-MS Found: m/z 361.2[M+H]+

Example 12

5-(4-((2-phenoxypyridin-3-yl)methoxy)phenyl)isoxazol-3-ol

The title compound was obtained as a white solid by the same method as in Example 3 or in accordance with the method or by combining it with an ordinary method, using (2-phenoxypyridin-3-yl)methanol.
$^1$HNMR (400 MHz, CDCl$_3$) δ: 5.26 (2H, s), 6.03 (1H, s), 7.02-7.06 (3H, m), 7.11-7.13 (2H, m), 7.19 (1H, dd, J=7.4, 7.4 Hz), 7.39 (2H, dd, J=7.4, 7.4 Hz), 7.65 (2H, d, J=8.8 Hz), 7.87-7.88 (1H, m), 8.08-8.09 (1H, m)
ESI-MS Found: m/z 361.0[M+H]+

Example 13

5-(3,5-difluoro-4-((2-phenoxypyridin-3-yl)methoxy)phenyl)isoxazol-3-ol

The title compound was obtained as a white solid by the same method as in Example 3 or in accordance with the method or by combining it with an ordinary method, using (2-phenoxypyridin-3-yl)methanol and 2,6-difluoro-4-iodophenol.
$^1$HNMR (400 MHz, CDCl$_3$) δ: 5.43 (2H, s), 6.16 (1H, s), 7.05 (1H, dd, J=7.4, 5.0 Hz), 7.08-7.10 (2H, m), 7.19-7.21 (1H, m), 7.28 (2H, d, J=8.8 Hz), 7.38-7.40 (2H, m), 7.93 (1H, dd, J=7.4, 2.0 Hz), 8.13 (1H, dd, J=5.0, 2.0 Hz)
ESI-MS Found: m/z 397.1[M+H]+

Example 14

5-(4-((2-(4-fluorophenoxy)pyridin-3-yl)methoxy)phenyl)isoxazol-3-ol

The title compound was obtained as a white solid by the same method as in Example 3 or in accordance with the method or by combining it with an ordinary method, using (2-(4-fluorophenoxy)pyridin-3-yl)methanol.

$^1$HNMR (400 MHz, CDCl$_3$) δ: 5.29 (2H, s), 6.37 (1H, s), 7.15-7.26 (7H, m), 7.73 (2H, d, J=8.8 Hz), 7.97 (1H, dd, J=7.6, 2.0 Hz), 8.08 (1H, dd, J=5.0, 2.0 Hz)

ESI-MS Found: m/z 379.3[M+H]+

Example 15

5-(4-((2-(isopropylthio)pyridin-3-yl)methoxy)phenyl)isoxazol-3-ol

1) Production of (2-(isopropylthio)pyridin-3-yl)methanol

To a solution of 2-mercaptonicotinic acid (700 mg) in dimethylformamide (7 ml), 1.35 ml of 2-iodopropane and 541 mg of sodium hydride were added under ice-cooling, and the reaction solution was stirred at room temperature for 4 hours, at 60° C. for 2 hours. The reaction solution was cooled, then diluted with a saturated aqueous ammonium chloride solution, and extracted with ethyl acetate. The combined organic layers were washed with a saturated saline solution and then dried over anhydrous sodium sulfate. The solvent was distilled off under reduced pressure to afford a crude product as a yellow oil. To a solution of lithium aluminum hydride (428 mg) in tetrahydrofuran (7 ml), a solution of the crude product in tetrahydrofuran (3 ml) was added under ice-cooling, and the reaction solution was stirred at the same temperature for 30 minutes. To the reaction solution was added sodium sulfate decahydrate, and the mixture was further stirred at the same temperature for 1 hour. The reaction solution was Celite-filtered, the filtrate was distilled off under reduced pressure, and the residue obtained was purified by silica gel column chromatography (eluent: hexane/ethyl acetate (95:5-50:50)) to afford the title compound as a colorless oil.

2) Production of 5-(4-((2-(isopropylthio)pyridin-3-yl)methoxy)phenyl)isoxazol-3-ol The title compound was obtained as a white solid by the same method as in Example 6 or in accordance with the method or by combining it with an ordinary method, using (2-(isopropylthio)pyridin-3-yl)methanol.

$^1$HNMR (400 MHz, CDCl$_3$) δ: 1.44 (6H, d, J=6.8 Hz), 4.19-4.22 (1H, m), 5.07 (2H, d, J=9.2 Hz), 6.10 (1H, s), 7.04-7.06 (3H, m), 7.68-7.70 (3H, m), 8.44 (1H, d, J=3.7 Hz)

ESI-MS Found: m/z 343.4[M+H]+

Example 16

5-(4-((2-isopropoxybenzyl)oxy)phenyl)isoxazol-3-ol

1) Production of (2-isopropoxyphenyl)methanol

To a solution of 2-hydroxybenzaldehyde (0.5 ml) in dimethylformamide (5 ml), 1.35 ml of 2-bromopropane and 1.98 g of potassium carbonate were added, and the reaction solution was stirred overnight at room temperature. To the reaction solution was added 1N hydrochloric acid, and the mixture was extracted with ethyl acetate. The combined organic layers were washed with a saturated saline solution and dried over anhydrous sodium sulfate. The solvent was distilled off under reduced pressure to afford a crude product as a yellow oil. To a solution of the crude product in methanol (5 ml), 362 mg of sodium borohydride was added under ice-cooling, and the reaction solution was stirred at room temperature for 30 minutes. To the reaction solution was added 10% aqueous citric acid, and the mixture was extracted with ethyl acetate. The combined organic layers were washed with a saturated saline solution and dried over anhydrous sodium sulfate. The solvent was distilled off under reduced pressure, and the residue obtained was purified by silica gel column chromatography (eluent: hexane/ethyl acetate (98:2-50:50)) to afford the title compound as a colorless oil.

2) Production of 5-(4-((2-isopropoxybenzyl)oxy)phenyl)isoxazol-3-ol

The title compound was obtained as a white solid by the same method as in Example 6 or in accordance with the method or by combining it with an ordinary method, using (2-isopropoxyphenyl)methanol.

$^1$HNMR (400 MHz, CDCl$_3$) δ: 1.36 (6H, d, J=6.1 Hz), 4.61-4.63 (1H, m), 5.16 (2H, s), 6.08 (1H, s), 6.92-6.96 (2H, m), 7.06 (2H, d, J=8.8 Hz), 7.28 (1H, d, J=6.7 Hz), 7.43 (1H, d, J=7.4 Hz), 7.66 (2H, d, J=8.8 Hz)

ESI-MS Found: m/z 326.2[M+H]+

Example 17

5-(4-((2-(pyridin-3-yloxy)benzyl)oxy)phenyl)isoxazol-3-ol

The title compound was obtained as a white solid by the same method as in Example 16 or in accordance with the method or by combining it with an ordinary method, using 2-fluorobenzaldehyde and 3-hydroxypyridine.

$^1$HNMR (400 MHz, CDCl$_3$) δ: 5.19 (2H, s), 6.06 (1H, s), 6.95-6.98 (3H, m), 7.31-7.32 (3H, m), 7.34-7.36 (1H, m), 7.60-7.64 (3H, m), 8.40 (2H, d, J=9.6 Hz)

ESI-MS Found: m/z 361.2[M+H]+

Example 18

5-(4-((3-fluoro-2-phenoxybenzyl)oxy)phenyl)isoxazol-3-ol

The title compound was obtained as a white solid by the same method as in Example 16 or in accordance with the method or by combining it with an ordinary method, using 2,3-difluorobenzaldehyde and phenol.

$^1$HNMR (400 MHz, DMSO-d$_6$) δ: 5.13 (2H, s), 6.39 (1H, s), 6.88 (2H, d, J=7.6 Hz), 6.97 (2H, d, J=9.0 Hz), 7.06 (1H, s), 7.32-7.34 (2H, m), 7.40 (1H, s), 7.45-7.48 (2H, m), 7.67 (2H, d, J=9.0 Hz)

ESI-MS Found: m/z 378.1[M+H]+

Example 19

5-(4-((2-fluoro-6-phenoxybenzyl)oxy)phenyl)isoxazol-3-ol

The title compound was obtained as a yellow oil by the same method as in Example 16 or in accordance with the method or by combining it with an ordinary method, using 2,6-difluorobenzaldehyde and phenol.
$^1$HNMR (400 MHz, CDCl$_3$) δ: 5.25 (2H, s), 6.08 (1H, s), 6.69 (1H, d, J=8.4 Hz), 6.92 (1H, m), 7.00-7.04 (2H, m), 7.13-7.15 (1H, m), 7.26-7.28 (2H, m), 7.34 (3H, t, J=7.9 Hz), 7.64 (2H, d, J=8.8 Hz)
ESI-MS Found: m/z 378.1[M+H]+

Example 20

5-(4-((2-(2,6-difluorophenoxy)pyridin-3-yl)methoxy)phenyl)isoxazol-3-ol

1) Production of (2-(2,6-difluorophenoxy)pyridin-3-yl)methanol

To a solution of 2-chloronicotinic acid ethyl (0.5 ml) in dimethylformamide (5 ml), 658 mg of 2,6-difluorophenol and 1.65 g of cesium carbonate were added, and the reaction solution was stirred overnight at 100° C. The reaction solution was cooled, then 1N hydrochloric acid was added, and the mixture was extracted with ethyl acetate. The combined organic layers were washed with a saturated saline solution and dried over anhydrous sodium sulfate. The solvent was distilled off under reduced pressure to afford a crude product as a brown oil. To a solution of lithium aluminum hydride (256 mg) in tetrahydrofuran (5 ml), a solution of the crude product in tetrahydrofuran (3 ml) was added under ice-cooling, and the reaction solution was stirred at room temperature for 2 hours. To the reaction solution was added sodium sulfate decahydrate, and the mixture was stirred at the same temperature for 1 hour. The reaction solution was Celite-filtered, the filtrate was distilled off under reduced pressure, and the residue obtained was purified by silica gel column chromatography (eluent: hexane/ethyl acetate (95:5-50:50)) to afford the title compound as a pale pink solid.

2) Production of 5-(4-((2-(2,6-difluorophenoxy)pyridin-3-yl)methoxy)phenyl)isoxazol-3-ol The title compound was obtained as a white solid by the same method as in Example 5 or in accordance with the method or by combining it with an ordinary method, using (2-(2,6-difluorophenoxy)pyridin-3-yl)methanol.
$^1$HNMR (400 MHz, DMSO-d$_6$) δ: 5.35 (2H, s), 6.44 (1H, s), 7.22-7.32 (6H, m), 7.77 (2H, d, J=8.4 Hz), 8.07-8.11 (2H, m)
ESI-MS Found: m/z 397.1[M+H]+

Example 21

5-(4-((5-fluoro-2-phenoxybenzyl)oxy)phenyl)isoxazol-3-ol

The title compound was obtained as a white solid by the same method as in Example 16 or in accordance with the method or by combining it with an ordinary method, using 2,5-difluorobenzaldehyde and phenol.
$^1$HNMR (400 MHz, CDCl$_3$) δ: 5.17 (2H, s), 6.08 (1H, s), 6.94-7.02 (7H, m), 7.32-7.36 (3H, m), 7.65 (2H, d, J=8.8 Hz)
ESI-MS Found: m/z 378.1[M+H]+

Example 22

5-(4-((3-isopropoxybenzyl)oxy)phenyl)isoxazol-3-ol

1) Production of (3-isopropoxyphenyl)methanol

To a solution of methyl 3-hydroxybenzoate (500 mg) in dimethylformamide (5 ml), 0.463 ml of 2-bromopropane and 197 mg of sodium hydride were added under ice-cooling, and the reaction solution was stirred at room temperature for 5 hours. To the reaction solution was added 10% aqueous citric acid, and the mixture was extracted with ethyl acetate. The combined organic layers were washed with a saturated saline solution and dried over anhydrous sodium sulfate. The solvent was distilled off under reduced pressure to afford a crude product as a yellow oil. To a solution of lithium aluminum hydride (250 mg) in tetrahydrofuran (3 ml), a solution of the crude product in tetrahydrofuran (2 ml) was added under ice-cooling, and the reaction solution was stirred at room temperature for 1 hour. To the reaction solution was added sodium sulfate decahydrate, and the mixture was stirred at the same temperature for 1 hour. The reaction solution was Celite-filtered, and the filtrate was distilled off under reduced pressure. The residue obtained was purified by silica gel column chromatography (eluent: hexane/ethyl acetate (98:2-30:70)) to afford the title compound as a colorless oil.

2) Production of 5-(4-((3-isopropoxybenzyl)oxy)phenyl)isoxazol-3-ol

The title compound was obtained as a white solid by the same method as in Example 5 or in accordance with the method or by combining it with an ordinary method, using (3-isopropoxyphenyl)methanol.
$^1$HNMR (400 MHz, CDCl$_3$) δ: 1.34 (6H, d, J=6.1 Hz), 4.55-4.58 (1H, m), 5.08 (2H, s), 6.08 (1H, s), 6.86 (1H, d, J=9.6 Hz), 6.97-7.04 (4H, m), 7.28 (1H, t, J=7.1 Hz), 7.66 (2H, d, J=8.8 Hz)
ESI-MS Found: m/z 326.1[M+H]+

Example 23

5-(4-((3-phenoxypyridin-2-yl)methoxy)phenyl)isoxazol-3-ol

1) Production of 6-chloro-3-fluoropyridin-2-carboxylic acid methyl ester

To a solution of 6-chloro-3-fluoropyridin-2-carboxylic acid (250 mg) in methanol (3 ml), 0.3 ml of concentrated sulfuric acid was added, and the reaction solution was heated to reflux for 2.5 hours. The reaction solution was cooled, and then the solvent was distilled off under reduced pressure. To the residue obtained was added 1N aqueous sodium hydroxide, and the mixture was extracted with ethyl acetate. The combined organic layers were washed with a saturated saline solution and dried over anhydrous sodium sulfate. The solvent was distilled off under reduced pressure to afford the title compound as a white solid.

2) Production of (6-chloro-3-phenoxypyridin-2-yl)methanol

To a solution of 6-chloro-3-fluoropyridin-2-carboxylic acid methyl ester (245 mg) in dimethylformamide (3 ml), 200 mg of phenol and 393 mg of potassium carbonate were added, and the reaction solution was stirred at 100° C. for 1.5 hours. The reaction solution was cooled, then 1N hydrochloric acid was added, and the mixture was extracted with ethyl acetate. The combined organic layers were washed with a saturated saline solution and dried over anhydrous sodium sulfate. The solvent was distilled off under reduced pressure to afford a crude product as a brown oil. To a solution of the crude product in toluene (5 ml), 9.9 ml of diisobutylaluminum hydride (1.0M hexane solution) was added at −78° C., and the reaction solution was stirred for 2 hours while increasing the temperature of the reaction solution to room temperature. To the reaction solution were added water and 10% aqueous citric acid sequentially, and the mixture was extracted with ethyl acetate. The combined organic layers were washed with a saturated saline solution and dried over anhydrous sodium sulfate. The solvent was distilled off under reduced pressure, and the residue obtained was purified by silica gel column chromatography (eluent: hexane/ethyl acetate (98:2-50:50)) to afford the title compound as a pale yellow oil.

3) Production of (3-phenoxypyridin-2-yl)methanol

To a solution of (6-chloro-3-phenoxypyridin-2-yl)methanol (88 mg) in ethanol (1.5 ml), 10 mg of 10% palladium-carbon catalyst was added, and the reaction solution was stirred for 20 hours under hydrogen atmosphere. The catalyst was filtered off through Celite, and the filtrate was distilled off under reduced pressure to afford the title compound as a yellow solid.

4) Production of 5-(4-((3-phenoxypyridin-2-yl)methoxy)phenyl)isoxazol-3-ol

The title compound was obtained as a pale yellow solid by the same method as in Example 5 or in accordance with the method or by combining it with an ordinary method, using (3-phenoxypyridin-2-yl)methanol.
$^1$HNMR (400 MHz, CDCl$_3$) δ: 5.37 (2H, s), 6.03 (1H, s), 7.01 (2H, d, J=7.6 Hz), 7.05 (2H, d, J=8.8 Hz), 7.17 (1H, t, J=7.6 Hz), 7.26-7.28 (2H, m), 7.37 (2H, t, J=8.0 Hz), 7.61 (2H, d, J=8.8 Hz), 8.43 (1H, s)
ESI-MS Found: m/z 361.2[M+H]+

Example 24

5-(4-((2-isobutylpyridin-3-yl)methoxy)phenyl)isoxazol-3-ol

1) Production of (2-isobutylpyridin-3-yl)methanol

To a solution of (2-bromopyridin-3-yl)methanol (100 mg) in tetrahydrofuran (1 ml), 36 mg of dichloro(1,1'-bis(diphenylphosphino)ferrocene)nickel(II) and 0.8 ml of isobutyl magnesium bromide (2.0M diethyl ether solution) were added under ice-cooling, and the reaction solution was stirred at the same temperature for 4 hours. To the reaction solution was added saturated aqueous ammonium chloride solution, and the mixture was extracted with ethyl acetate. The combined organic layers were washed with a saturated saline solution and dried over anhydrous sodium sulfate. The solvent was distilled off under reduced pressure, and the residue obtained was purified by silica gel column chromatography (eluent: hexane/ethyl acetate (98:2-50:50)) to afford the title compound as a yellow oil.

2) Production of 5-(4-((2-isobutylpyridin-3-yl)methoxy)phenyl)isoxazol-3-ol

The title compound was obtained as a pale yellow solid by the same method as in Example 6 or in accordance with the method or by combining it with an ordinary method, using (2-isobutylpyridin-3-yl)methanol.
$^1$HNMR (400 MHz, CD$_3$OD) δ: 0.95 (6H, d, J=6.7 Hz), 1.29 (1H, m), 2.77 (2H, d, J=7.0 Hz), 5.21 (2H, s), 6.20 (1H, s), 7.13 (2H, d, J=8.8 Hz), 7.31-7.32 (1H, m), 7.74 (2H, d, J=8.8 Hz), 7.93 (1H, d, J=8.0 Hz), 8.44-8.46 (1H, m)
ESI-MS Found: m/z 325.1[M+H]+

Example 25

5-(4-((3-phenoxybenzyl)oxy)phenyl)isoxazol-3-ol

The title compound was obtained as a white solid by the same method as in Example 6 or in accordance with the method or by combining it with an ordinary method, using (3-phenoxyphenyl)methanol.
$^1$HNMR (400 MHz, CDCl$_3$) δ: 5.08 (2H, s), 6.10 (1H, s), 7.02-7.06 (6H, m), 7.13 (1H, t, J=6.8 Hz), 7.33-7.41 (4H, m), 7.68 (2H, d, J=8.8 Hz)
ESI-MS Found: m/z 360.1[M+H]+

Example 26

5-(3,5-difluoro-4-((2-phenoxybenzyl)oxy)phenyl)isoxazol-3-ol

The title compound was obtained as a white solid by the same method as in Example 3 or in accordance with the method or by combining it with an ordinary method, using 2,6-difluoro-4-iodophenol.
$^1$HNMR (400 MHz, CDCl$_3$) δ: 5.37 (2H, s), 6.13 (1H, s), 6.86 (1H, d, J=8.2 Hz), 6.93 (2H, d, J=8.6 Hz), 7.09 (1H, t, J=7.4 Hz), 7.15 (1H, t, J=7.4 Hz), 7.20-7.35 (5H, m), 7.69 (1H, d, J=7.4 Hz)
ESI-MS Found: m/z 396.0[M+H]+

Example 27

5-(4-((2-phenoxybenzyl)oxy)phenyl)isoxazol-3-ol

The title compound was obtained as a white solid by the same method as in Example 3 or in accordance with the method or by combining it with an ordinary method, using 4-iodophenol.
$^1$HNMR (400 MHz, CDCl$_3$) δ: 5.23 (2H, s), 6.07 (1H, s), 6.93 (1H, d, J=8.2 Hz), 7.01 (4H, m), 7.12 (1H, t, J=7.4 Hz), 7.16 (1H, t, J=7.4 Hz), 7.26-7.40 (3H, m), 7.57 (1H, d, J=7.4 Hz), 7.64 (2H, d, J=8.8 Hz)
ESI-MS Found: m/z 360.0[M+H]+

Example 28

5-(3-fluoro-4-((2-phenoxybenzyl)oxy)phenyl)isoxazol-3-ol

The title compound was obtained as a white solid by the same method as in Example 3 or in accordance with the method or by combining it with an ordinary method, using 2-fluoro-4-iodophenol obtained in Reference Example 4.
$^1$HNMR (400 MHz, CDCl$_3$) δ: 5.29 (2H, s), 6.09 (1H, s), 6.91 (1H, d, J=8.0 Hz), 7.01 (2H, m), 7.04-7.19 (3H, m), 7.24-7.48 (5H, m), 7.60 (1H, d, J=7.6 Hz)
ESI-MS Found: m/z 378.0[M+H]+

Example 29

5-(4-((2-phenoxybenzyl)oxy)benzyl)isoxazol-3-ol

1) Production of (2-phenoxyphenyl)methanol

To a solution of 2-phenoxybenzoic acid (20.8 g) in tetrahydrofuran (400 ml), 14.6 ml of borane-tetrahydrofuran complex (1M tetrahydrofuran solution) was added, and the reaction solution was stirred at 50° C. for 4 hours. The reaction solution was cooled, then water was added, and the mixture was extracted with chloroform. The combined organic layers were washed with 1N aqueous sodium hydroxide and dried over anhydrous sodium sulfate. The solvent was distilled off under reduced pressure to afford the title compound as a colorless oil.

2) Production of methyl(4-((2-phenoxybenzyl)oxy)phenyl)acetate

To a solution of (2-phenoxyphenyl)methanol (1.43 g) in tetrahydrofuran (25 ml), 1.19 g of methyl(4-hydroxyphenyl) acetate, 2.82 g of triphenylphosphine, and 4.86 ml of diethyl azodicarboxylate (45% toluene solution) were added, and the reaction solution was stirred at room temperature for 30 minutes. The reaction solvent was distilled off under reduced pressure, and the residue obtained was purified by silica gel column chromatography (eluent: ethyl acetate/hexane (5:95-30:70)) to afford the title compound as a colorless oil.

3) Production of ethyl 3-oxo-4-(4-((2-phenoxybenzyl)oxy)phenyl)butanoate

To a mixed solution of methyl(4-((2-phenoxybenzyl)oxy) phenyl)acetate (150 mg) in methanol (2.5 ml) and tetrahydrofuran (1.5 ml), 0.43 ml of 5N aqueous sodium hydroxide was added, and the reaction solution was stirred at room temperature for 1 hour. To the reaction solution was added 10% aqueous citric acid, and the mixture was extracted with chloroform. The combined organic layers were washed with a saturated saline solution and dried over anhydrous magnesium sulfate. The solvent was distilled off under reduced pressure to afford a crude product as a colorless oil. To a solution of the crude product in chloroform (2 ml), 64 mg of Meldrum's acid, 84 mg of 1-ethyl-3-(3-dimethylaminopropyl)carbodiimide hydrochloride, and 110 mg of 4-dimethylaminopyridine were added, and the reaction solution was stirred overnight at room temperature. The reaction solution was diluted with chloroform and water, washed with 5% aqueous citric acid and a saturated saline solution sequentially, and dried over anhydrous magnesium sulfate. The solvent was distilled off under reduced pressure, and the residue obtained was purified by silica gel column chromatography (eluent: chloroform/methanol (98:2)) to afford a colorless oil. To a solution of the resultant oil (100 mg) in toluene (2 ml) was added 0.12 ml of ethanol, and the reaction solution was heated to reflux for 5 hours. The reaction solvent was distilled off under reduced pressure, and the residue obtained was purified by silica gel column chromatography (eluent: hexane/ethyl acetate (90:10-70:30)) to afford the title compound as a colorless oil.

4) Production of N-hydroxy-3-oxo-4-(4-((2-phenoxybenzyl)oxy)phenyl)butanamide

To a solution of ethyl 3-oxo-4-(4-((2-phenoxybenzyl)oxy) phenyl)butanoate (40 mg) in 1,4-dioxan (0.12 ml), 9 mg of hydroxylammonium chloride and 0.1 ml of 2.5N sodium hydroxide were added under ice-cooling, and the reaction solution was stirred at 0° C. for 1.5 hours. Concentrated hydrochloric acid (0.07 ml) was further added, and the reaction solution was stirred at room temperature for 20 minutes. The reaction solution was extracted with chloroform, the combined organic layers were washed with a saturated saline solution and dried over anhydrous magnesium sulfate. The solvent was distilled off under reduced pressure, and the residue obtained was purified by preparative thin layer chromatography (Kieselgel™ 60 $F_{254}$, Art5744, made by Merck & Co., hexane/ethyl acetate (1:1) to afford the title compound as a yellow oil.

5) Production of 5-(4-((2-phenoxybenzyl)oxy)benzyl)isoxazol-3-ol

To a solution of N-hydroxy-3-oxo-4-(4-((2-phenoxybenzyl)oxy)phenyl)butanamide (17.2 mg) in acetic acid (0.2 ml), 0.05 ml of concentrated hydrochloric acid was added, and the reaction solution was stirred overnight at room temperature. The solvent was distilled off under reduced pressure, and the residue obtained was purified by preparative thin layer chromatography (Kieselgel™ 60 $F_{254}$, Art5744, made by Merck & Co., hexane/ethyl acetate (1:1) to afford the title compound as a yellow oil.

$^1$HNMR (400 MHz, CDCl$_3$) δ: 3.88 (2H, s), 5.14 (2H, s), 5.58 (1H, s), 6.91 (3H, m), 6.98 (2H, m), 7.11 (4H, m), 7.26 (1H, m), 7.33 (2H, m), 7.57 (1H, m)

ESI-MS Found: m/z 374[M+H]+

Example 30

5-(4-(2-(5-methyl-2-phenyl-1,3-thiazol-4-yl)ethoxy) phenyl)isoxazol-3-ol

1) Production of 3-(methoxymethoxy)-5-(4-(2-(5-methyl-2-phenyl)-1,3-thiazol-4-yl)ethoxy)phenyl) isoxazole The title compound was obtained as a yellow solid by the same method as in Example 4 (Step 2) or in accordance with the method or by combining it with an ordinary method, using 2-(5-methyl-2-phenyl-1,3-thiazol-4-yl)ethanol (98 mg) and 4-(3-(methoxymethoxy)isoxazol-5-yl)phenol (98 mg) obtained in Reference Example 5.

2) Production of 5-(4-(2-(5-methyl-2-phenyl-1,3-thiazol-4-yl)ethoxy)phenyl)isoxazol-3-ol To a solution of 3-(methoxymethoxy)-5-(4-(2-(5-methyl-2-phenyl)-1,3-thiazol-4-yl)ethoxy)phenyl)isoxazole (56 mg) in tetrahydrofuran (2 ml), 0.5 ml of 5N hydrochloric acid was added, and the reaction solution was stirred overnight at room temperature. The solvent was distilled off under reduced pressure, and the residue obtained was purified through reversed phase medium pressure liquid chromatography (ODS-AS-360-CC (by YMC), mobile phase: water-acetonitrile-0.1% trifluoroacetic acid). The solvent of the resultant fraction was distilled off under reduced pressure to afford the title compound as a pale yellow solid.

$^1$HNMR (400 MHz, DMSO-d$_6$) δ: 2.44 (3H, s), 3.14 (2H, t, J=6.6 Hz), 4.36 (2H, t, J=6.6 Hz), 6.38 (1H, s), 7.04-7.07 (2H, m), 7.42-7.48 (3H, m), 7.68-7.72 (2H, m), 7.83-7.85 (2H, m)

ESI-MS Found: m/z 379.2[M+H]+

Example 31

5-(4-((5-phenylisoxazol-4-yl)methoxy)phenyl)isoxazol-3-ol

The title compound was obtained as a pale yellow solid by the same method as in Example 4 or in accordance with the method or by combining it with an ordinary method, using 5-phenylisoxazol-4-carboxylic acid.

$^1$HNMR (400 MHz, CD$_3$OD) δ: 5.14 (2H, s), 6.04 (1H, brs), 7.06 (2H, dd, J=7.0, 2.1 Hz), 7.49-7.52 (3H, m), 7.66 (2H, dd, J=7.0, 2.1 Hz), 7.74-7.77 (2H, m), 8.54 (1H, s)

ESI-MS Found: m/z 335.4[M+H]+

Example 32 benzyl(3-(4-(3-hydroxyisoxazol-5-yl)phenoxy)propyl)carbamate

The title compound was obtained as a pale yellow solid by the same method as in Example 6 or in accordance with the method or by combining it with an ordinary method, using benzyl (3-hydroxypropyl)carbamate.

$^1$HNMR (400 MHz, CD$_3$OD) δ: 1.94-2.00 (2H, m), 3.32 (2H, t, J=6.1 Hz), 4.05 (2H, t, J=6.1 Hz), 5.06 (2H, s), 6.15 (1H, s), 6.99 (2H, d, J=8.8 Hz), 7.25-7.34 (5H, m), 7.66 (2H, d, J=8.8 Hz)

ESI-MS Found: m/z 369.3[M+H]+

Example 33

5-(4-(2-(5-methyl-2-phenyl-1,3-oxazol-4-yl)ethoxy)phenyl)isoxazol-3-ol

The title compound was obtained as a pale yellow solid by the same method as in Example 30 or in accordance with the method or by combining it with an ordinary method, using 2-(5-methyl-2-phenyl-1,3-oxazol-4-yl)ethanol.

$^1$HNMR (400 MHz, DMSO-d$_6$) δ: 2.36 (3H, s), 2.95 (2H, t, J=6.6 Hz), 4.27 (2H, t, J=6.6 Hz), 6.38 (1H, s), 7.04-7.07 (2H, m), 7.46-7.51 (3H, m), 7.68-7.72 (2H, m), 7.89-7.92 (2H, m)

ESI-MS Found: m/z 363.2[M+H]+

Example 34

5-(4-(2-(3-((6-fluoropyridin-3-yl)oxy)phenyl)ethoxy)phenyl)isoxazol-3-ol

1) Production of 2-(3-((6-fluoropyridin-3-yl)oxy)phenyl)ethanol

To a solution of 3-(2-hydroxyethyl)phenol (142.5 mg) in chloroform (5 ml), 279 mg of (6-fluoro-3-pyridinyl)boronic acid, 0.043 ml of triethylamine, 681 mg of copper acetate, and 500 mg of 4A molecular sieve were added, and the reaction solution was stirred at room temperature for 6 days. The reaction solution was filtered through Celite, and the filtrate was diluted with water, extracted with chloroform, and dried over anhydrous magnesium sulfate. The reaction solvent was distilled off under reduced pressure, and the residue obtained was purified by silica gel column chromatography (eluent: ethyl acetate/hexane (0:100-50:50-75/25)) to afford the title compound as a yellow oil.

2) Production of 5-(4-(2-(3-((6-fluoropyridin-3-yl)oxy)phenyl)ethoxy)phenyl)isoxazol-3-ol The title compound was obtained as a white solid by the same method as in Example 4 (Step 2) or in accordance with the method or by combining it with an ordinary method, using 2-(3-((6-fluoropyridin-3-yl)oxy)phenyl)ethanol.

$^1$HNMR (400 MHz, DMSO-d$_6$) δ: 3.06 (2H, t, J=6.7 Hz), 4.26 (2H, t, J=6.7 Hz), 6.40 (1H, s), 6.88-6.94 (1H, m), 7.00-7.08 (3H, m), 7.15 (1H, d, J=7.9 Hz), 7.23 (1H, dd, J=8.9, 3.2 Hz), 7.35 (1H, t, J=7.9 Hz), 7.65-7.75 (3H, m), 8.04 (1H, s), 11.29 (1H, brs)

ESI-MS Found: m/z 393.1[M+H]+

Example 35

5-(6-(2-(3-isopropoxyphenyl)ethoxy)pyridin-3-yl)isoxazol-3-ol

1) Production of methyl(3-hydroxyphenyl)acetate

To a solution of 3-hydroxyphenylacetate (2.0 g) in methanol (10 ml), 250 mg of tosic acid monohydrate and 2.9 ml of trimethoxymethane were added, and the reaction solution was heated to reflux for 5 hours. The reaction solution was cooled, and then the solvent was distilled off under reduced pressure. The residual residue was diluted with diethyl ether, washed with a saturated aqueous sodium bicarbonate solution, and dried over anhydrous magnesium sulfate. The solvent was distilled off under reduced pressure, and the residue obtained was purified by silica gel column chromatography (eluent: ethyl acetate/hexane (0:100-50:50)) to afford the title compound as a colorless oil.

2) Production of methyl(3-isopropoxyphenyl)acetate

To a solution of methyl(3-hydroxyphenyl)acetate (200 mg) in tetrahydrofuran (5 ml), 0.15 ml of isopropyl alcohol, 480 mg of triphenylphosphine, and 0.82 ml of diethyl azodicarboxylate (45% toluene solution) were added, and the reaction solution was stirred overnight at room temperature. The reaction solvent was distilled off under reduced pressure, and the residue obtained was purified by silica gel column chromatography (eluent: ethyl acetate/hexane (0:100-25:75-60/40)) to afford the title compound as a colorless oil.

3) Production of 2-(3-isopropoxyphenyl)ethanol

To a solution of methyl(3-isopropoxyphenyl)acetate (280 mg) in tetrahedron (5 ml), 52 mg of lithium aluminum hydride was added under ice-cooling, and the reaction solution was stirred at the same temperature for 25 minutes. To the reaction solution was added sodium sulfate decahydrate, and the mixture was stirred at room temperature for 2 hours. The reaction solution was filtered, and then the filtrate was distilled off under reduced pressure. The residue obtained was purified by silica gel column chromatography (eluent: ethyl acetate/hexane (0:100-50:50) to afford the title compound as a colorless oil.

4) Production of 5-(6-(2-(3-isopropoxyphenyl)ethoxy)pyridin-3-yl)isoxazol-3-ol

The title compound was obtained as a yellow oil by the same method as in Example 6 or in accordance with the method or by combining it with an ordinary method, using 5-iodo-2-pyridinol and 2-(3-isopropoxyphenyl)ethanol.

$^1$HNMR (400 MHz, DMSO-d$_6$) δ: 1.23 (6H, d, J=5.9 Hz), 2.99 (2H, t, J=6.7 Hz), 4.46-4.61 (3H, m), 6.51 (1H, s), 6.75 (1H, d, J=7.6 Hz), 6.82 (2H, d, J=7.6 Hz), 6.91 (1H, d, J=8.6 Hz), 7.18 (1H, t, J=7.6 Hz), 8.06 (1H, dd, J=8.6, 2.0 Hz), 8.61 (1H, d, J=2.0 Hz), 11.42 (1H, brs)

ESI-MS Found: m/z 341.4[M+H]+

Example 36

5-(4-(2-(3-ethoxyphenoxy)ethyl)phenyl)isoxazol-3-ol

The title compound was obtained as a yellow oil by the method as in Example 6, methods equivalent thereto or combinations of them with usual methods, using ethyl(3-(4-(2-hydroxyethyl)phenyl)-2-propinoate obtained in Reference Example 3 and 3-ethoxyphenol.

$^1$HNMR (400 MHz, DMSO-$d_6$) δ: 1.28 (3H, t, J=7.0 Hz), 3.06 (2H, t, J=6.7 Hz), 3.96 (2H, q, J=7.0 Hz), 4.18 (2H, t, J=6.7 Hz), 6.42-6.52 (4H, m), 7.13 (1H, t, J=8.1 Hz), 7.44 (2H, d, J=8.1 Hz), 7.72 (2H, d, J=8.1 Hz), 11.35 (1H, brs)

ESI-MS Found: m/z 326.4[M+H]+

Example 37

5-(4-(2-(3-nitrophenyl)ethoxy)phenyl)isoxazol-3-ol

The title compound was obtained as a white solid by the same method as in Example 6 or in accordance with the method or by combining it with an ordinary method, using 2-(3-nitrophenyl)ethanol.

$^1$HNMR ((400 MHz, DMSO-$d_6$) δ: 3.21 (2H, t, J=6.6 Hz), 4.32 (2H, t, J=6.6 Hz), 6.38 (1H, s), 7.04 (2H, d, J=8.8 Hz), 7.61 (1H, t, J=7.9 Hz), 7.70 (2H, d, J=8.8 Hz), 7.82 (1H, d, J=7.9 Hz), 8.07-8.12 (1H, m), 8.23 (1H, brs), 11.29 (1H, brs)

ESI-MS Found: m/z 327.4[M+H]+

Example 38

5-(4-(2-(3-(phenoxyphenyl)ethoxy)phenyl)isoxazol-3-ol

1) Production of 2-(3-phenoxyphenyl)ethanol

To a solution of (3-phenoxyphenyl)acetic acid (1.157 g) in tetrahydrofuran (23 ml), 6.5 ml of borane-tetrahydrofuran complex (1.17M tetrahydrofuran solution) was added, and the reaction solution was stirred at room temperature for 2 hours. To the reaction solution was added water, and the mixture was extracted with chloroform and dried over anhydrous sodium sulfate. The solvent was distilled off under reduced pressure, and the residue obtained was purified by silica gel column chromatography (eluent: ethyl acetate/hexane (10:90-80/20)) to afford the title compound as a colorless oil.

2) Production of 5-(4-(2-(3-(phenoxyphenyl)ethoxy)phenyl)isoxazol-3-ol

The title compound was obtained as a white solid by the same method as in Example 4 (Step 2 and 3) or in accordance with the method or by combining it with an ordinary method, using 2-(3-phenoxyphenyl)ethanol.

$^1$HNMR (400 MHz, CDCl$_3$) δ: 3.09 (2H, t, J=6.8 Hz), 4.21 (2H, t, J=6.8 Hz), 6.08 (1H, s), 6.86-6.98 (4H, m), 6.99-7.06 (3H, m), 7.11 (1H, t, J=7.2 Hz), 7.28-7.36 (3H, m), 7.62-7.68 (2H, m)

ESI-MS Found: m/z 374.2[M+H]+

Example 39

5-(4-(1-naphthylmethoxy)phenyl)isoxazol-3-ol

The title compound was obtained as a yellow oil by the same method as in Example 6 or in accordance with the method or by combining it with an ordinary method, using 1-naphthalenemethanol.

$^1$HNMR (400 MHz, DMSO-$d_6$) δ: 5.62 (2H, s), 6.41 (1H, s), 7.22 (2H, d, J=8.6 Hz), 7.47-7.63 (3H, m), 7.69 (1H, d, J=7.4 Hz), 7.75 (2H, d, J=8.6 Hz), 7.91-8.01 (2H, m), 8.09 (1H, d, J=7.4 Hz), 11.32 (1H, s)

ESI-MS Found: m/z 318.2[M+H]+

Example 40

5-(4-(2-(6-(4-fluorophenyl)pyridin-2-yl)ethoxy)phenyl)isoxazol-3-ol

1) Production of 5-(4-(2-(6-chloropyridin-2-yl)ethoxy)phenyl)isoxazol-3-ol

The title compound was obtained as a brown solid by the same method as in Example 6 or in accordance with the method or by combining it with an ordinary method, using 2-(6-chloro-2-pyridinyl)ethanol reported in U.S. Pat. No. 5,741,796 (A2).

2) 5-(4-(2-(6-(4-fluorophenyl)pyridin-2-yl)ethoxy)phenyl)isoxazol-3-ol

To a solution of 5-(4-(2-(6-chloropyridin-2-yl)ethoxy)phenyl)isoxazol-3-ol (46.5 mg) in dimethoxyethane ethylene glycol dimethyl ether (3 ml), 18 mg of tetrakis triphenylphosphine palladium, 31 mg of 4-fluorophenylboronic acid and 0.2 ml of 2M aqueous sodium carbonate solution were added, and the reaction solution was stirred at 90° C. for 2 hours. The reaction solution was cooled, then diluted with a saturated saline solution, extracted with ethyl acetate, and dried over anhydrous magnesium sulfate. The solvent was distilled off under reduced pressure, and the residue obtained was purified through reversed phase medium pressure liquid chromatography (ODS-AS-360-CC (by YMC), mobile phase: water-acetonitrile-0.1% trifluoroacetic acid). The solvent of the resultant fraction was diluted with ethyl acetate, washed with saturated sodium bicarbonate water, and then dried over anhydrous magnesium sulfate. The solvent was distilled off under reduced pressure, and the residue obtained was purified by preparative thin layer chromatography (Kieselgel™ 60 F$_{254}$, Art5744, made by Merck & Co., methanol/chloroform (1:9)) to afford the title compound as a brown solid.

$^1$HNMR (400 MHz, DMSO-$d_6$) δ: 3.27 (2H, t, J=6.6 Hz), 4.50 (2H, t, J=6.6 Hz), 6.38 (1H, s), 7.06 (2H, d, J=8.6 Hz), 7.24-7.37 (3H, m), 7.70 (2H, d, J=8.6 Hz), 7.78-7.86 (2H, m), 8.13 (2H, dd, J=8.6, 6.0 Hz), 11.26 (1H, brs)

ESI-MS Found: m/z 377.2[M+H]+

Example 41

5-(4-(2-(3-isopropylamino)phenyl)ethoxy)phenyl)isoxazol-3-ol

1) Production of 5-(4-(2-(3-nitrophenyl)ethoxy)phenyl)-3-isoxazolyl pivalate

To a solution of 5-(4-(2-(3-nitrophenyl)ethoxy)phenyl)isoxazol-3-ol (117 mg) obtained in Example 37 in chloroform (5 ml), 0.15 ml of triethylamine and 0.052 ml of pivaloyl chloride were added, and the reaction solution was stirred at room temperature for 2 hours. The reaction solution was diluted with ethyl acetate, washed with a saturated saline solution, and dried over anhydrous magnesium sulfate. The solvent was distilled off under reduced pressure, and the residue obtained was purified by silica gel column chromatography (eluent: ethyl acetate/hexane (0:1-1:3)) to afford the title compound as a white solid.

2) Production of 5-(4-(2-(3-aminophenyl)ethoxy) phenyl)-3-isoxazolyl pivalate

To a solution of 5-(4-(2-(3-nitrophenyl)ethoxy)phenyl)-3-isoxazolyl pivalate (100 mg) in ethyl acetate (5 ml), 13 mg of 10% palladium-carbon catalyst was added, and the reaction solution was stirred at room temperature for 1 hour under hydrogen atmosphere. The catalyst was filtered off through Celite, then the filtrate was distilled off under reduced pressure, and the residue obtained was purified by silica gel column chromatography (eluent: ethyl acetate/hexane (0:100-25:75-30:70)) to afford the title compound as a yellow oil.

3) Production of 5-(4-(2-(3-(isopropylamino)phenyl) ethoxy)phenyl)-3-isoxazolyl pivalate To a solution of 5-(4-(2-(3-aminophenyl)ethoxy)phenyl)-3-isoxazolyl pivalate (27.6 mg) in methanol (1 ml), 0.020 ml of acetone, 19.2 mg of sodium cyanoborohydride and 0.05 ml of acetic acid were added, and the reaction solution was stirred at room temperature for 2 hours. The reaction solution was diluted with saturated aqueous hydrogen carbonate sodium, extracted with chloroform, and dried over anhydrous magnesium sulfate. The solvent was distilled off under reduced pressure, and the residue obtained was purified by preparative thin layer chromatography (Kieselgel™ 60 $F_{254}$, Art5744, made by Merck & Co., ethyl acetate/hexane (50:50)) to afford the title compound as a colorless oil.

4) Production of 5-(4-(2-(3-(isopropylamino)phenyl) ethoxy)phenyl)isoxazol-3-ol

To a solution of 5-(4-(2-(3-(isopropylamino)phenyl) ethoxy)phenyl)-3-isoxazolyl pivalate (24.9 mg) in methanol (1 ml), 0.05 ml of 4N aqueous sodium hydroxide was added, and the reaction solution was stirred at room temperature for 1 hour. To the reaction solution was added 10% aqueous citric acid, and the mixture was extracted with chloroform and dried over anhydrous magnesium sulfate. The solvent was distilled off under reduced pressure, and the residue obtained was purified by preparative thin layer chromatography (Kieselgel™ 60 $F_{254}$, Art5744, made by Merck & Co., chloroform/methanol (90:10)) to afford the title compound as a colorless amorphous matter.

$^1$HNMR (400 MHz, CDCl$_3$) δ: 1.22 (6H, d, J=6.3 Hz), 3.03 (2H, t, J=7.2 Hz), 3.57-3.69 (1H, m), 4.20 (2H, t, J=7.2 Hz), 5.50-6.19 (1H, brm), 6.07 (1H, s), 6.46-6.55 (2H, m), 6.60 (1H, d, J=7.4 Hz), 6.95 (2H, d, J=9.0 Hz), 7.12 (1H, t, J=7.7 Hz), 7.64 (2H, d, J=9.0 Hz)
ESI-MS Found: m/z 339.4[M+H]+

Example 42

5-(4-(2-(3-(6-fluoropyridin-3-yl)phenyl)ethoxy)phenyl)isoxazol-3-ol

The title compound was obtained as a white solid by the same method as in Example 41 (Step 2) or in accordance with the method or by combining it with an ordinary method, using 2-(3-bromophenyl)ethanol and (6-fluoropyridin-3-yl)boronic acid.

$^1$HNMR (400 MHz, DMSO-d$_6$) δ: 3.14 (2H, t, J=6.8 Hz), 4.33 (2H, t, J=6.8 Hz), 6.40 (1H, s), 7.08 (2H, d, J=9.0 Hz), 7.30 (1H, dd, J=8.0, 2.2 Hz), 7.37-7.49 (2H, m), 7.59 (1H, d, J=8.0 Hz), 7.68-7.75 (3H, m), 8.30 (1H, dt, J=2.2, 8.0 Hz), 8.57 (1H, brs), 11.29 (1H, brs)
ESI-MS Found: m/z 377.2[M+H]+

Example 43

5-(4-(2-(3-(methoxymethyl)phenyl)ethoxy)phenyl)isoxazol-3-ol

1) Production of methyl(3-(methoxymethyl)phenyl)acetate

To a solution of ethyl(3-(bromomethyl)phenyl)acetate (1.78 g) in carbon tetrachloride (80 ml), 1.78 g of N-bromosuccinimide and 100 mg of benzoyl peroxide were added, and the reaction solution was heated overnight at reflux. The reaction solution was cooled, then the solvent was distilled off under reduced pressure, and the residue obtained was purified by silica gel column chromatography (eluent: ethyl acetate/hexane (0:100-10:90)) to afford a crude product. To a solution of the crude product (304 mg) in methanol (1 ml), 0.3 ml of sodium methoxide (25% methanol solution) was added, and the reaction solution was stirred at room temperature for 1.5 hours. The reaction solution was diluted with ethyl acetate, washed with a saturated aqueous ammonium chloride solution and a saturated saline solution sequentially, and dried over anhydrous magnesium sulfate. The solvent was distilled off under reduced pressure, and the residue obtained was purified by preparative thin layer chromatography (Kieselgel™ 60 $F_{254}$, Art5744, made by Merck & Co., ethyl acetate/hexane (20:80)) to afford the title compound as a colorless oil.

2) Production of 2-(3-methoxymethyl)phenylethanol

To a solution of methyl(3-(methoxymethyl)phenyl)acetate (78.6 mg) in tetrahydrofuran (3 ml), 19 mg of lithium aluminum hydride was added under ice-cooling, and the reaction solution was stirred at the same temperature for 15 minutes. To the reaction solution was added sodium hydrogensulfate decahydrate, and the reaction solution was stirred overnight at room temperature. The reaction solution was filtered, and the filtrate was concentrated under reduced pressure. The residue obtained was purified by silica gel column chromatography (eluent: ethyl acetate/hexane (0:100-60:40)) to afford the title compound as a colorless oil.

3) Production of 5-(4-(2-(3-(methoxymethyl)phenyl) ethoxy)phenyl)isoxazol-3-ol

The title compound was obtained as a white solid by the same method as in Example 6 or in accordance with the method or by combining it with an ordinary method, using 2-(3-methoxymethyl)phenylethanol.

$^1$HNMR (400 MHz, DMSO-d$_6$) δ: 3.04 (2H, t, J=6.7 Hz), 3.27 (3H, s), 4.24 (2H, t, J=6.7 Hz), 4.38 (2H, s), 6.38 (1H, s), 7.04 (2H, d, J=8.6 Hz), 7.20-7.13 (1H, m), 7.21-7.33 (3H, m), 7.33 (2H, d, J=8.6 Hz), 11.15-11.39 (1H, brm)
ESI-MS Found: m/z 326.2[M+H]+

Example 44

5-(4-(2-(3-propylphenoxy)ethyl)phenyl)isoxazol-3-ol

The title compound was obtained as a white solid by the same method as in Example 6 or in accordance with the method or by combining it with an ordinary method, using 3-propylphenol and ethyl (3-(4-(2-hydroxyethyl)phenyl)-2-propinoate obtained in Reference Example 6.

$^1$HNMR (400 MHz, DMSO-$d_6$) δ: 0.86 (3H, t, J=7.4 Hz), 1.47-1.61 (2H, m), 2.44-2.52 (2H, m), 3.06 (2H, t, J=6.6 Hz), 4.18 (2H, t, J=6.6 Hz), 6.49 (1H, s), 6.68-6.77 (3H, m), 7.15 (1H, t, J=8.0 Hz), 7.45 (2 H, d, J=8.0 Hz), 7.72 (2H, d, J=8.0 Hz), 11.36 (1H, s)

ESI-MS Found: m/z 324.2[M+H]+

Example 45

5-(4-((3-phenoxyphenoxy)methyl)phenyl)isoxazol-3-ol

The title compound was obtained as a white solid by the same method as in Example 6 or in accordance with the method or by combining it with an ordinary method, using 3-phenoxyphenol and ethyl 3-(4-(hydroxymethyl)phenyl)-2-propinoate obtained in Reference Example 2.

$^1$HNMR (400 MHz, DMSO-$d_6$) δ: 5.16 (2H, s), 6.53-6.58 (2H, m), 6.66 (1H, t, J=2.2 Hz), 6.81 (1H, dd, J=8.1, 2.2 Hz), 7.01 (2H, d, J=8.1 Hz), 7.15 (1H, t, J=7.7 Hz), 7.29 (1H, t, J=8.1 Hz), 7.39 (2H, t, J=7.7 Hz), 7.55 (2H, d, J=8.1 Hz), 7.81 (2H, d, J=8.1 Hz)

ESI-MS Found: m/z 360.2[M+H]+

Example 46

5-(4-(2-(2-fluoro-5-methoxyphenyl)ethoxy)phenyl)isoxazol-3-ol

1) Production of 2-(2-fluoro-5-methoxyphenyl)ethanol

To a mixed solution of 2-fluoro-5-methoxybenzaldehyde (0.8 ml) in tetrahydrofuran (4 ml) and dimethylsulfoxide (4 ml), 1.97 g of trimethylsulfonium iodide and 308 mg of sodium hydride were added under ice-cooling, and the reaction solution was stirred at room temperature for 2 hours. To the reaction solution was added a saturated aqueous ammonium chloride solution, and the mixture was extracted with ethyl acetate. The combined organic layers were washed with a saturated saline solution and dried over anhydrous sodium sulfate. The solvent was distilled off under reduced pressure, and the residue obtained was purified by silica gel column chromatography (eluent: hexane/ethyl acetate (98:2-50:50)) to afford a crude product as a colorless oil. To a solution of the crude product in tetrahydrofuran (2 ml), 200 mg of Sodium cyanoborohydride and 0.4 ml of trifluoroborane-diethylether complex were added under ice-cooling, and the reaction solution was stirred at room temperature for 2 hours. To the reaction solution was added 10% aqueous citric acid, and the mixture was extracted with chloroform and dried over anhydrous sodium sulfate. The solvent was distilled off under reduced pressure, and the residue obtained was purified by silica gel column chromatography (eluent: hexane/ethyl acetate (95:5-30/70)) to afford the title compound as a colorless oil.

2) Production of 5-(4-(2-(2-fluoro-5-methoxyphenyl)ethoxy)phenyl)isoxazol-3-ol

The title compound was obtained as a white solid by the same method as in Example 6 or in accordance with the method or by combining it with an ordinary method, using 2-(2-fluoro-5-methoxyphenyl)ethanol.

$^1$HNMR (400 MHz, CDCl$_3$) δ: 3.13 (2H, t, J=7.0 Hz), 3.79 (3H, s), 4.23 (2H, t, J=7.0 Hz), 6.08 (1H, s), 6.72-6.76 (1H, m), 6.81-6.84 (1H, m), 6.95-6.98 (3H, m), 7.66 (2H, d, J=9.0 Hz)

ESI-MS Found: m/z 330.4[M+H]+

Example 47

5-(4-(2-(2-isopropoxypyridin-4-yl)ethoxy)phenyl)isoxazol-3-ol

1) Production of 2-(2-isopropoxypyridin-4-yl)ethanol

To a solution of 4-methylpyridin-2-ol (1.0 g) in chloroform (10 ml), 1.37 ml of 2-iodopropane and 3.8 g of silver carbonate (II) were added, and the reaction solution was stirred at room temperature for 24 hours. The reaction solution was Celite-filtered, and the filtrate was distilled off under reduced pressure to afford a crude product as a yellow oil. To a solution of the crude product in tetrahydrofuran (8 ml), 7.2 ml of N-butyllithium (1.5M hexane solution) was added at –78° C., and the reaction solution was stirred at the same temperature for 30 minutes and then stirred at room temperature for 15 minutes. The reaction solution was recooled to –78° C., 324 mg of paraformaldehyde was added, and the reaction solution was stirred for 3 hours while increasing the temperature of the reaction solution to room temperature. To the reaction solution was added a saturated aqueous ammonium chloride solution, and the mixture was extracted with ethyl acetate. The combined organic layers were washed with a saturated saline solution and dried over anhydrous sodium sulfate. The solvent was distilled off under reduced pressure, and the residue obtained was purified by silica gel column chromatography (eluent: hexane/ethyl acetate (98:2-50/50)) to afford the title compound as a yellow oil.

2) Production of 5-(4-(2-(2-isopropoxypyridin-4-yl)ethoxy)phenyl)isoxazol-3-ol

The title compound was obtained as a white solid by the same method as in Example 6 or in accordance with the method or by combining it with an ordinary method, using 2-(2-isopropoxypyridin-4-yl)ethanol.

$^1$HNMR (400 MHz, CDCl$_3$) δ: 1.35 (6H, d, J=6.3 Hz), 3.05 (2H, t, J=6.6 Hz), 4.23 (2H, t, J=6.6 Hz), 5.27-5.30 (1H, m), 6.09 (1H, s), 6.62 (1H, s), 6.78 (1H, d, J=4.9 Hz), 6.95 (2H, d, J=8.8 Hz), 7.65 (2H, d, J=8.8 Hz), 8.09 (1H, d, J=4.9 Hz)

ESI-MS Found: m/z 341.4[M+H]+

Example 48

5-(4-(2-(6-isopropoxypyridin-2-yl)ethoxy)phenyl)isoxazol-3-ol

The title compound was obtained as a white solid by the same method as in Example 50 or in accordance with the method or by combining it with an ordinary method, using 6-methylpyridin-2-ol.

¹HNMR (400 MHz, CDCl₃) δ: 1.33 (6H, d, J=6.3 Hz), 3.16 (2H, t, J=6.7 Hz), 4.41 (2H, t, J=6.7 Hz), 5.25-5.28 (1H, m), 6.09 (1H, s), 6.53-6.55 (1H, m), 6.77 (1H, d, J=7.2 Hz), 6.97 (2H, d, J=8.8 Hz), 7.47-7.50 (1H, m), 7.66 (2H, d, J=8.8 Hz)

ESI-MS Found: m/z 341.4[M+H]+

Example 49

5-(4-(2-(3-methoxyphenyl)ethoxy)phenyl)isoxazol-3-ol

1) Production of 2-(3-((tert-butyl(dimethyl)silyl)oxy)phenyl)ethanol

To a solution of 3-hydroxyphenylacetic acid (1.5 g) in dimethylformamide (15 ml), 3.4 g of imidazole and 4.5 g of tert-butyldimethylchlorosilane was added, and the reaction solution was stirred overnight at room temperature. The reaction solution was diluted with water and extracted with ethyl acetate. The combined organic layers were washed with a saturated saline solution and then dried over anhydrous sodium sulfate. The solvent was distilled off under reduced pressure to afford a crude product as a brown oil. To a solution of lithium aluminum hydride (748 mg) in tetrahydrofuran (10 ml), a solution of the crude product in tetrahydrofuran (5 ml) was added under ice-cooling, and the reaction solution was stirred at the same temperature for 1 hour. To the reaction solution was added sodium sulfate decahydrate, the mixture was stirred at the same temperature for further 1 hour and then Celite-filtered, and the filtrate was distilled off under reduced pressure. The residue was purified by silica gel column chromatography (eluent: hexane/ethyl acetate (98:2-50/50)) to afford the title compound as a yellow oil.

2) Production of ethyl 3-(4-(2-(3-((tert-butyl(dimethyl)silyl)oxy)phenyl)ethoxy)phenyl)propionate To a solution of 2-(3-((tert-butyl(dimethyl)silyl)oxy)phenyl)ethanol (926 mg) in tetrahydrofuran (8 ml), 838 mg of ethyl 3-(4-hydroxyphenyl)-2-propinoate obtained in Reference Example 1, 1.93 g of triphenylphosphine and 3.34 ml of diethyl azodicarboxylate (2.2M toluene solution) were added under ice-cooling, and the reaction solution was stirred at room temperature for 1 hour. To the reaction solution was added methanol, the solvent was distilled off under reduced pressure, and the residue obtained was purified by silica gel column chromatography (eluent: hexane/ethyl acetate (98:2-50/50)) to afford the title compound as a pink oil.

3) Production of ethyl 3-(4-(2-(3-hydroxyphenyl)ethoxy)phenyl)ethyl propionate To a solution of ethyl 3-(4-(2-(3-((tert-butyl(dimethyl)silyl)oxy)phenyl)ethoxy)phenyl)propionate (1.56 g) in dimethylformamide (10 ml), 426 mg of potassium fluoride and 0.186 ml of hydrogen bromide (48%) were added, and the reaction solution was stirred overnight at room temperature. The reaction solution was diluted with water and extracted with ethyl acetate. The combined organic layers were washed with a saturated saline solution and then dried over anhydrous sodium sulfate. The solvent was distilled off under reduced pressure, and the residue obtained was purified by silica gel column chromatography (eluent: hexane/ethyl acetate (98:2-50/50)) to afford the title compound as a colorless oil.

4) Production of 5-(4-(2-(3-methoxyphenyl)ethoxy)phenyl)isoxazol-3-ol

To a solution of ethyl 3-(4-(2-(3-hydroxyphenyl)ethoxy)phenyl)propionate (120 mg) in dimethylformamide (1.5 ml), 0.048 ml of iodomethane and 31 mg of sodium hydride were added, and the reaction solution was stirred at room temperature for 30 minutes. To the reaction solution was added a saturated aqueous ammonium chloride solution, and the mixture was extracted with ethyl acetate. The combined organic layers were washed with a saturated saline solution and then dried over anhydrous sodium sulfate, and the solvent was distilled off under reduced pressure. The residue obtained was purified by silica gel column chromatography (eluent: hexane/ethyl acetate (98:2-50/50)) to afford the title compound as a colorless oil.

5) Production of ethyl 5-(4-(2-(3-methoxyphenyl)ethoxy)phenyl)isoxazol-3-ol To a mixed solution of ethyl 3-(4-(2-(3-methoxyphenyl)ethoxy)phenyl)propionate (75 mg) in tetrahydrofuran (1 ml) and ethanol (0.5 ml), 0.041 ml of hydroxylamine (50% aqueous solution) and 0.277 ml of 2.5N aqueous sodium hydroxide were added, and the reaction solution was stirred overnight at room temperature. To the reaction solution was added 10% aqueous citric acid, and the mixture was extracted with chloroform and dried over anhydrous sodium sulfate. The solvent was distilled off under reduced pressure, and the residue obtained was purified by preparative thin layer chromatography (Kieselgel™ 60 F₂₅₄, Art5744, made by Merck & Co., ethyl acetate/hexane (25:75)) to afford the title compound as a white solid.

¹HNMR (400 MHz, CDCl₃) δ: 3.10 (2H, t, J=6.9 Hz), 3.81 (3H, s), 4.22 (2H, t, J=6.9 Hz), 6.08 (1H, s), 6.80 (1H, d, J=8.4 Hz), 6.84 (1H, s), 6.88 (1H, d, J=7.6 Hz), 6.95 (2H, d, J=8.6 Hz), 7.24-7.26 (1H, m), 7.76 (2H, d, J=8.6 Hz)

ESI-MS Found: m/z 312.1[M+H]+

Example 50

5-(4-(2-(3-isopropoxyphenyl)ethoxy)phenyl)isoxazol-3-ol

The title compound was obtained as a white solid by the same method as in Example 46 (Step 4 and 5) or in accordance with the method or by combining it with an ordinary method, using isopropanol.

¹HNMR (400 MHz, CDCl₃) δ: 1.34 (6H, d, J=6.1 Hz), 3.08 (2H, t, J=7.0 Hz), 4.21 (2H, t, J=7.0 Hz), 4.55-4.56 (1H, m), 6.08 (1H, s), 6.77-6.79 (1H, m), 6.83-6.86 (2H, m), 6.95 (2H, d, J=8.6 Hz), 7.22 (1H, t, J=7.8 Hz), 7.65 (2H, d, J=8.6 Hz)

ESI-MS Found: m/z 340.1[M+H]+

Example 51

5-(4-(2-(4-fluoro-3-methoxyphenyl)ethoxy)phenyl)isoxazol-3-ol

The title compound was obtained as a white solid by the same method as in Example 46 or in accordance with the method or by combining it with an ordinary method, using 4-fluoro-3-methoxybenzaldehyde.

¹HNMR (400 MHz, CDCl₃) δ: 3.08 (2H, t, J=6.8 Hz), 3.91 (3H, s), 4.21 (2H, t, J=6.8 Hz), 6.09 (1H, s), 6.82 (1H, s), 6.90 (1H, d, J=7.8 Hz), 6.96 (2H, d, J=8.6 Hz), 7.00-7.05 (1H, m), 7.66 (2H, d, J=8.6 Hz)

ESI-MS Found: m/z 330.4[M+H]+

Example 52

5-(4-(2-(2-phenoxypyridin-4-yl)ethoxy)phenyl)isoxazol-3-ol

1) Production of 2-phenoxyisonicotinaldehyde

To a solution of 2-chloro-4-cyanopyridine (1.5 g) in dimethylformamide (10 ml), 1.52 g of phenol and 2.2 g of potassium carbonate were added, and the reaction solution was stirred overnight at 120° C. The reaction solution was cooled, then 1N hydrochloric acid was added, and the mixture was extracted with ethyl acetate. The combined organic layers were washed with a saturated saline solution and then dried over anhydrous sodium sulfate. The solvent was distilled off under reduced pressure, and the residue obtained was purified by silica gel column chromatography (eluent: hexane/ethyl acetate (98:2-50/50), chloroform/methanol (99.5:0.5-92:8)) to afford a crude product as a white solid. To a solution of the crude product in toluene (10 ml), 15 ml of diisobutylaluminum hydride (1.0M toluene solution) was added at −78° C., and the reaction solution was stirred at the same temperature for 2 hours. To the reaction solution were added water and a saturated aqueous ammonium chloride solution sequentially, and the mixture was extracted with ethyl acetate. The combined organic layers were washed with a saturated saline solution and then dried over anhydrous sodium sulfate. The solvent was distilled off under reduced pressure, and the residue obtained was purified by silica gel column chromatography (eluent: hexane/ethyl acetate (98:2-50/50)) to afford the title compound as a yellow oil.

2) Production of 4-oxiran-2-yl-phenoxypyridine

To a solution of 2-phenoxyisonicotinaldehyde (378 mg) in tetrahydrofuran (4 ml), 0.228 ml of diiodomethane and 3.8 ml of methyllithium (1.0M diethyl ether solution) were added under ice-cooling, and the reaction solution was stirred at the same temperature for 1 hour. To the reaction solution was added 10% aqueous citric acid, and the mixture was extracted with ethyl acetate. The combined organic layers were washed with a saturated saline solution and then dried over anhydrous sodium sulfate. The solvent was distilled off under reduced pressure, and the residue obtained was purified by silica gel column chromatography (eluent: hexane/ethyl acetate (98:2-50/50)) to afford the title compound as a yellow oil.

3) Production of 2-(2-phenoxypyridin-4-yl)ethanol

To a solution of 4-oxiran-2-yl-phenoxypyridine (168 mg) in methanol (2 ml), 20 mg of 10% palladium-carbon catalyst was added, and the reaction solution was stirred overnight at room temperature under hydrogen atmosphere. The reaction solution was Celite-filtered, and the filtrate was distilled off under reduced pressure to afford the title compound as a colorless oil.

4) Production of 5-(4-(2-(2-phenoxypyridin-4-yl)ethoxy)phenyl)isoxazol-3-ol The title compound was obtained as a white solid by the same method as in Example 6 or in accordance with the method or by combining it with an ordinary method, using 2-(2-phenoxypyridin-4-yl)ethanol.

$^1$HNMR (400 MHz, CDCl$_3$) δ: 3.09 (2H, t, J=5.8 Hz), 4.26 (2H, t, J=5.8 Hz), 6.15 (1H, s), 6.86 (1H, s), 6.95 (2H, d, J=8.4 Hz), 7.06-7.08 (3H, m), 7.18-7.20 (1H, m), 7.37-7.39 (2H, m), 7.65 (2H, d, J=8.4 Hz), 8.03-8.04 (1H, m)

ESI-MS Found: m/z 375.1[M+H]+

Example 53

5-(4-(2-(3-(cyclohexyloxy)phenyl)ethoxy)phenyl)isoxazol-3-ol

The title compound was obtained as a yellow oil by the same method as in Example 6 or in accordance with the method or by combining it with an ordinary method, using cyclohexanol.

$^1$HNMR (400 MHz, CDCl$_3$) δ: 1.26-1.36 (4H, m), 1.52-1.54 (2H, m), 1.78-1.81 (2H, m), 1.98-2.05 (2H, m), 3.07 (2H, t, J=7.0 Hz), 4.20-4.23 (2H, m), 6.07 (1H, s), 6.78-6.80 (1H, m), 6.82-6.84 (2H, m), 6.94 (2H, d, J=8.6 Hz), 7.21 (1H, t, J=8.0 Hz), 7.64 (2H, d, J=8.6 Hz)

ESI-MS Found: m/z 380.2[M+H]+

Example 54

5-(4-(2-(2-phenoxyphenyl)ethoxy)phenyl)isoxazol-3-ol

1) Production of 2-phenoxybenzaldehyde

To a solution of 2-fluorobenzaldehyde (0.5 ml) in dimethylformamide (5 ml), 676 mg of phenol and 993 mg of potassium carbonate were added, and the reaction solution was stirred overnight at 100° C. The reaction solution was cooled, then 1N hydrochloric acid was added, and the mixture was extracted with ethyl acetate. The combined organic layers were washed with a saturated saline solution and dried over anhydrous sodium sulfate. The solvent was distilled off under reduced pressure, and the residue obtained was purified by silica gel column chromatography (eluent: hexane/ethyl acetate (98:2-50/50)) to afford the title compound as a pale yellow oil.

2) Production of 2-(2-phenoxyphenyl)ethanol

To a solution of 2-phenoxybenzaldehyde (535 mg) in tetrahydrofuran (5 ml), 0.326 ml of diiodomethane and 5.4 ml of methyllithium (1.0M diethyl ether solution) were added under ice-cooling, and the reaction solution was stirred at the same temperature for 30 minutes and then at room temperature for 1 hour. To the reaction solution was added water, and the mixture was extracted with ethyl acetate. The combined organic layers were washed with a saturated saline solution and dried over anhydrous sodium sulfate. The solvent was distilled off under reduced pressure to afford a crude product as a yellow oil. To a solution of the crude product in tetrahydrofuran (5 ml), 284 mg of sodium cyanoborohydride and 0.569 ml of trifluoroborane-diethyl ether complex were added under ice-cooling, and the reaction solution was stirred at the same temperature for 50 minutes. To the reaction solution was added a saturated saline solution, and the mixture was extracted with ethyl acetate. The combined organic layers were washed with a saturated saline solution and dried over anhydrous sodium sulfate. The solvent was distilled off under reduced pressure, and the residue obtained was purified by silica gel column chromatography (eluent: hexane/ethyl acetate (95:5-50/50)) to afford the title compound as a colorless oil.

3) Production of 5-(4-(2-(2-phenoxyphenyl)ethoxy)phenyl)isoxazol-3-ol

The title compound was obtained as a white solid by the same method as in Example 6 or in accordance with the method or by combining it with an ordinary method, using 2-(2-phenoxyphenyl)ethanol.

$^1$HNMR (400 MHz, CDCl$_3$) δ: 3.16 (2H, t, J=7.0 Hz), 4.24 (2H, t, J=7.0 Hz), 6.06 (1H, s), 6.91 (3H, d, J=8.4 Hz), 6.96 (2H, d, J=8.0 Hz), 7.07-7.13 (2H, m), 7.23 (1H, t, J=9.3 Hz), 7.31-7.38 (3H, m), 7.61 (2H, d, J=8.4 Hz)

ESI-MS Found: m/z 374.2[M+H]+

Example 55

5-(4-(2-methoxy-2-(3-methoxyphenyl)ethoxy)phenyl)isoxazol-3-ol

1) Production of 1-(2-(4-iodophenoxy)-1-methoxyethyl)-3-methoxybenzene

To a solution of 2-(4-iodophenoxy)-1-(3-methoxyphenyl)ethanol (215 mg) in dimethylformamide (2 ml), 0.072 ml of iodomethane and 46 mg of sodium hydride were added under ice-cooling, and the reaction solution was stirred at room temperature for 30 minutes. To the reaction solution was added an aqueous saturated ammonium chloride solution, and the mixture was extracted with ethyl acetate. The combined organic layers were washed with a saturated saline solution and then dried over anhydrous sodium sulfate. The solvent was distilled off under reduced pressure, and the residue obtained was purified by silica gel column chromatography (eluent: hexane/ethyl acetate (98:2-50/50)) to afford the title compound as a colorless oil.

2) Production of 5-(4-(2-methoxy-2-(3-methoxyphenyl)ethoxy)phenyl)isoxazol-3-ol

The title compound was obtained as a pale yellow solid by the same method as in Example 3 or in accordance with the method or by combining it with an ordinary method, using 1-(2-(4-iodophenoxy)-1-methoxyethyl)-3-methoxybenzene.

$^1$HNMR (400 MHz, CDCl$_3$) δ: 3.37 (3H, s), 3.84 (3H, s), 4.03-4.06 (1H, m), 4.18-4.22 (1H, m), 4.59 (1H, dd, J=7.9, 3.4 Hz), 6.08 (1H, s), 6.90 (1H, d, J=8.2 Hz), 6.96-6.99 (4H, m), 7.32 (1H, t, J=7.8 Hz), 7.64 (2H, d, J=8.8 Hz)

ESI-MS Found: m/z 342.4[M+H]+

Example 56

5-(4-(2-hydroxy-2-(3-methoxyphenyl)ethoxy)phenyl)isoxazol-3-ol

To a solution of 2-bromo-1-(3-methoxyphenyl)ethanone (200 mg) in dimethylformamide (3 ml), 212 mg of 4-(3-(methoxymethoxy)isoxazol-5-yl)phenol obtained in Reference Example 5 and 241 mg of potassium carbonate were added, and the reaction solution was stirred at 80° C. for 1 hour. The reaction solution was cooled, then 1N hydrochloric acid was added, and the mixture was extracted with ethyl acetate. The combined organic layers were washed with a saturated saline solution and dried over anhydrous sodium sulfate. The solvent was distilled off under reduced pressure to afford a crude product as an orange-colored solid. To a solution of the crude product in methanol (2 ml) and chloroform (2 ml), 46 mg of sodium borohydride was added under ice-cooling, and the reaction solution was stirred at the same temperature for 1 hour. To the reaction solution was added 10% aqueous citric acid, and the mixture was extracted with chloroform and dried over anhydrous sodium sulfate. The solvent was distilled off under reduced pressure to afford a crude product as a yellow oil. The crude product was dissolved in 2 ml of 4N hydrochloric acid-dioxane solution, and the reaction solution was stirred at room temperature for 90 minutes. The solvent was distilled off under reduced pressure, and the residue obtained was purified through reversed phase medium pressure liquid chromatography (mobile phase: water-acetonitrile-0.1% trifluoroacetic acid).

The solvent of the resultant fraction was distilled off under reduced pressure, and was purified by preparative thin layer chromatography (Kieselgel™ 60 F$_{254}$, Art5744, made by Merck & Co., chloroform/methanol (10:1) to afford the title compound as a pale yellow solid.

$^1$HNMR (400 MHz, CDCl$_3$) δ: 3.85 (3H, s), 4.06-4.17 (2H, m), 5.15 (1H, d, J=6.3 Hz), 6.10 (1H, s), 6.90 (1H, d, J=7.6 Hz), 6.99 (2H, d, J=8.6 Hz), 7.00-7.05 (2H, m), 7.33 (1H, t, J=7.8 Hz), 7.67 (2H, d, J=8.6 Hz)

ESI-MS Found: m/z 328.4[M+H]+

Example 57

5-(4-(3-phenoxypropoxy)phenyl)isoxazol-3-ol

Production of 1-(3-bromopropoxy)-4-iodobenzene

To a solution of 4-iodophenol (1.0 g) in dimethylformamide (10 ml), 273 mg of sodium hydride and 0.603 ml of 1,3-dibromopropane were added under ice-cooling, and the reaction solution was stirred at room temperature for 1 hour. To the reaction solution was added 10% aqueous citric acid, and the mixture was extracted with ethyl acetate. The combined organic layers were washed with a saturated saline solution and dried over anhydrous sodium sulfate. The solvent was distilled off under reduced pressure, and the residue obtained was purified by silica gel column chromatography (eluent: hexane/ethyl acetate (98:2-50/50)) to afford the title compound as a colorless oil.

2) Production of 1-iodo-4-(3-phenoxypropoxy)benzene

To a solution of 1-(3-bromopropoxy)-4-iodobenzene (277 mg) in dimethylformamide (3 ml), 115 mg of phenol and 49 mg of sodium hydride were added under ice-cooling, and the reaction solution was stirred at room temperature for 1 hour. To the reaction solution was added 10% aqueous citric acid, and the mixture was extracted with ethyl acetate. The combined organic layers were washed with a saturated saline solution and dried over anhydrous sodium sulfate. The solvent was distilled off under reduced pressure, and the residue obtained was purified by silica gel column chromatography (eluent: hexane/ethyl acetate (98:2-50/50)) to afford the title compound as a colorless oil.

3) Production of 5-(4-(3-phenoxypropoxy)phenyl)isoxazol-3-ol

The title compound was obtained as a white solid by the same method as in Example 3 or in accordance with the method or by combining it with an ordinary method, using 1-iodo-4-(3-phenoxypropoxy)benzene.

$^1$HNMR (400 MHz, CDCl$_3$) δ: 2.27-2.33 (2H, m), 4.17-4.25 (4H, m), 6.09 (1H, s), 6.92-7.00 (5H, m), 7.31 (2H, d, J=7.6 Hz), 7.67 (2H, d, J=9.0 Hz)

ESI-MS Found: m/z 312.1[M+H]+

Example 58

5-(4-(2-(3-ethoxyphenyl)ethoxy)phenyl)isoxazol-3-ol

The title compound was obtained as a pale yellow solid by the same method as in Example 50 (Steps 4 and 5) or in accordance with the method or by combining it with an ordinary method, using iodoethane.

$^1$HNMR (400 NHz, CDCl$_3$) δ: 1.42 (3H, t, J=7.0 Hz), 3.09 (2H, t, J=6.9 Hz), 4.04 (2H, t, J=6.9 Hz), 4.22 (2H, q, J=7.0 Hz), 6.08 (1H, s), 6.79 (1H, d, J=8.4 Hz), 6.84-6.87 (2H, m), 6.95 (2H, d, J=8.8 Hz), 7.22 (1H, d, J=7.8 Hz), 7.65 (2H, d, J=8.8 Hz)

ESI-MS Found: m/z 326.1[M+H]+

Example 59

5-(4-(2-chloro-4-(trifluoromethyl)phenoxy)phenyl)isoxazol-3-ol

1) Production of 2-chloro-1-(4-iodophenoxy)-4-(trifluoromethyl)benzene

To a solution of 4-iodophenol (200 mg) in dimethylsulfoxide (1 ml), 218 mg of 2-chloro-1-fluoro-4-(trifluoromethyl)benzene and 251 mg of potassium carbonate were added, and the reaction solution was stirred at 120° C. for 3 hours. The reaction solution was cooled, ethyl acetate was added, the insoluble matter was filtered off, and the filtrate was washed with water and a saturated saline solution and dried over an anhydrous magnesium sulfate. The solvent was distilled off under reduced pressure, and the residue obtained was purified by silica gel column chromatography (eluent: hexane/ethyl acetate (98:2-80/20)) to afford the title compound as a colorless oil.

2) Production of 5-(4-(2-chloro-4-(trifluoromethyl)phenoxy)phenyl)isoxazol-3-ol The title compound was obtained as a white solid by the same method as in Example 3 or in accordance with the method or by combining it with an ordinary method, using 2-chloro-1-(4-iodophenoxy)-4-(trifluoromethyl)benzene.

$^1$HNMR (400 MHz, CDCl$_3$) δ: 6.17 (1H, s), 7.08 (3H, m), 7.54 (2H, m), 7.78 (3H, m)

ESI-MS Found: m/z 356.0[M+H]+

Example 60

5-(4-(2-chloro-4-(trifluoromethyl)phenoxy)-3-fluorophenoxy)isoxazol-3-ol

The title compound was obtained as a white solid by the same method as in Example 59 or in accordance with the method or by combining it with an ordinary method, using 2-fluoro-4-iodophenol.

$^1$HNMR (400 MHz, CDCl$_3$) δ: 6.23 (1H, s), 6.99 (1H, d, J=8.2 Hz), 7.12 (1H, t, J=8.2 Hz), 7.46-7.58 (2H, m), 7.61 (1H, dd, J=10.8, 2.2 Hz), 7.78 (1H, d, J=2.2 Hz)

ESI-MS Found: m/z 374.0[M+H]+

Example 61

5-(4-(2-chloro-4-(trifluoromethyl)phenoxy)-3,5-difluorophenoxy)isoxazol-3-ol The title compound was obtained as a white solid by the same method as in Example 59 or in accordance with the method or by combining it with an ordinary method, using 2,6-difluoro-4-iodophenol.

$^1$HNMR (400 MHz, CDCl$_3$) δ: 6.28 (1H, s), 6.83 (1H, d, J=8.8 Hz), 7.45 (3H, m), 7.76 (1H, d, J=2.1 Hz)

ESI-MS Found: m/z 392.0[M+H]+

The usefulness of the compound encompassed by formula (I) for a medicament is shown in tests described below.

The usefulness of the compound according to an embodiment of the present invention was assessed for a medicament by described methods of the following in vitro tests:

Test 1: Cloning of Genes

Primers were synthesized in the domains on the opposite sides of the base sequences of the ORFs of the known GPCR and GPR120 in GenBank Accession NOs. NM 181745 (human) and NM 181748 (mouse), and the genes were cloned by RT-PCR. The base sequences of the primers used are described below. The restriction enzymes, BamHI and EcoRI, recognition sites were introduced for subcloning, respectively.

```
hGPR120_F01:
                                         (SEQ ID NO: 1)
AGGATCCGCCGCCATGTCCCCTGAATGCGCGCGGGCAG hGPR102_R01:
                                         (SEQ ID NO: 2)
CGAATTCTTAGCCAGAAATAATCGACAAGTCATTTC mGPR120_F01:
                                         (SEQ ID NO: 3)
AGGATCCGCCGCCATGTCCCCTGAGTGTGCACAGACGAC mGPR120_R01:
                                         (SEQ ID NO: 4)
CGAATTCTTAGCTGGAAATAACAGACAAGTCATTTC
```

As samples for PCR, human small intestine Marathon-ready cDNA (CLONTECH, current corporate name: TaKaRa) and cDMA obtained by reverse transcription of mouse BAT-derived RNA were used for human and mouse GPR120 receptor genes, respectively.

Using KOD Plus (TOYOBO) for PCR, 30 cycles of 94° C. for 2 minutes, 94° C. for 15 seconds, 55° C. for 30 seconds and 68° C. for 1 minute were carried out to effect reaction, followed by addition of 0.5 units of ExTaq (TaKaRa) and incubation at 72° C. for 10 minutes to carry out A-addition reaction to terminals. For mouse PCR, 35 cycles were carried out on the condition of a final DMSO concentration of 2%.

Cloning of amplified PCR products was carried out using pCR2.1-TOPO TA cloning kit (Invitrogen). For verification of base sequences, electrophoresis was carried out using Big-Dye Terminator Cycle Sequencing Ready Reaction Kit Ver. 3.0 and 377 DNA Sequencer (Applied Biosystems) to determine the base sequences. The human GPR120 gene was 16 amino acids shorter than the sequence registered as GenBank Accession NO. NM 181745.

The GPR120 receptor genes cloned into pCR2.1-TOPO vectors, into which the restriction enzymes, BamHI and EcoRI, recognition sites were introduced, were excised from the vectors by the enzymes and subcloned into the BamHI and EcoRI recognition sites of eucaryotic expression vector EF1/V5-His B (Invitrogen).

Test 2: Production of Expression Cells

Using Lipofectamine 2000 (Invitrogen), cDNA of GPR120 receptor was transfected into CHO/NFAT-BLA cells, and drug-resistant cells were isolated to obtain GPR120 stable expression strains. The GPR120-expressed CHO cells were cultured in DMEM/F12 medium containing 10% fetal bovine serum, 100 units/ml penicillin, 0.1 mg/ml streptomycin sulfate, 250 µg/ml Zeocin, 500 µg/mL Geneticin and 15 mM HEPES.

Test 3: Measurement of Intracellular Calcium Concentration

On the day before the measurement day, 4 µM Fluo-4 AM (fluorescence calcium indicator reagent) was incubated to be introduced into the human GPR120 expression CHO cells plated at 20000 cells per well of a 96-well black plate (ViewPlate; Packard) in the presence of 2.5 mM probenecid in a $CO_2$ incubator for 1 hour. To the cells was added the test compound diluted with HBSS solution containing 20 mM HEPES and 2.5 mM probenecid. Variations in the intracellular calcium concentration were measured by Fluorescence Imaging Plate Reader (FLIPR; Molecular Devices) to examine the agonist action, and $EC_{50}$ values were calculated.

The GPR120 agonist action of the compound groups encompassed by the compound according to an embodiment of the present invention is as follows.

TABLE 5

| Example | IC50 (µM) |
|---------|-----------|
| 3 | 0.18 |
| 9 | 0.18 |
| 15 | 0.07 |
| 26 | 0.30 |
| 33 | 0.62 |
| 36 | 0.10 |
| 38 | 0.25 |
| 41 | 0.15 |
| 43 | 0.28 |
| 45 | 0.17 |

The above results exhibit that a compound according to an embodiment of the present invention or a pharmaceutically acceptable salt thereof has a GPR120 agonist action and is useful for treating and/or preventing diabetes mellitus or hyperlipidemia.

What is claimed is:

1. A compound of formula (I-1):

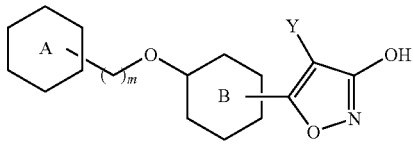

or a pharmaceutically acceptable salt thereof, wherein:

represents phenyl or 5- to 6-membered heteroaryl substituted with same or different 1 to 4 groups selected from the group consisting of:
lower alkyl, cycloalkyl, lower alkylthio, lower alkoxy, cycloalkylthio, lower alkylamino, cycloalkylamino, nitro, halogen atom, cyano, lower alkylsulfonyl, phenoxy, phenyl and heteroaryloxy;

represents a divalent group in which 2 hydrogen atoms are eliminated from benzene, pyridine, pyrazine, pyrimidine or pyridazine optionally substituted with same or different, 1 to 4 groups selected from the group consisting of:
halogen atom, lower alkyl, lower alkoxy, cyano and lower alkylsulfonyl;
m is an integer of 0 to 2; and
when m is 1 or 2, chain of

is optionally substituted with same or different, 1 to 2 hydroxy or lower alkyl; and
Y is hydrogen atom, lower alkyl optionally substituted with same or different, 1 to 3 lower alkoxy or halogen atom, lower alkoxy or halogen atom.

2. The compound according to claim 1, or a pharmaceutically acceptable salt thereof, wherein:

is phenyl, pyridinyl, oxazolyl, isoxazolyl or thiazolyl substituted with same or different, 1 to 4 groups selected from the group consisting of:
lower alkoxy, cycloalkyl, lower alkylthio, lower alkyl, cycloalkylthio, lower alkylamino, cycloalkylamino, nitro, halogen atom, cyano and lower alkylsulfonyl; and

is a divalent group in which 2 hydrogen atoms are eliminated from benzene, pyridine, pyrazine, pyrimidine or pyridazine optionally substituted with same or different, 1 to 4 groups selected from the group consisting of: halogen atom, lower alkyl, lower alkoxy, cyano and lower alkylsulfonyl.

3. The compound according to claim 1, or a pharmaceutically acceptable salt thereof, wherein:

is phenyl, pyridinyl, oxazolyl, isoxazolyl or thiazolyl substituted with same or different, 1 to 4 groups selected from the group consisting of:
lower alkoxy, cycloalkyl, lower alkylthio, lower alkyl, cycloalkylthio, lower alkylamino, cycloalkylamino, nitro, halogen atom, cyano and lower alkylsulfonyl; and

is a divalent group in which 2 hydrogen atoms are eliminated from benzene, pyridine, pyrazine, pyrimidine or pyridazine optionally substituted with same or different, 1 to 4 groups selected from the group consisting of:
lower alkoxy, cycloalkyl, lower alkylthio, lower alkyl, cycloalkylthio, lower alkylamino, cycloalkylamino, nitro, halogen atom, cyano and lower alkylsulfonyl;
provided that the compound of formula (I) does not include the case where

is phenyl optionally substituted with same or different, 1 to 4 groups selected from the group consisting of:
lower alkoxy, cycloalkyl, lower alkylthio, lower alkyl, cycloalkylthio, lower alkylthio, cycloalkylamino, nitro, halogen atom, cyano and lower alkylsulfonyl; and

is a divalent group in which 2 hydrogen atoms are eliminated from benzene optionally substituted with same or different, 1 to 4 groups selected from the group consisting of:
halogen atom, lower alkyl, lower alkoxy, cyano and lower alkylsulfonyl.

4. A pharmaceutical composition comprising a compound of claim 1 in combination with a pharmaceutically acceptable carrier.

5. A compound selected from the group consisting of
(1) 5-(4-((2-(cyclopentyloxy)pyridin-3-yl)methoxy)phenyl)isoxazol-3-ol;
(2) 5-(4-((2-isopropoxypyridin-3-yl)methoxy)phenyl)isoxazol-3-ol;
(3) 5-(4-((6-phenoxypyridin-2-yl)methoxy)phenyl)isoxazol-3-ol;
(4) 5-(4-((5-phenylisoxazol-3-yl)methoxy)phenyl)isoxazol-3-ol;
(5) 5-(4-(2-(3-fluorophenoxy)pyridin-3-yl)methoxy)phenyl)isoxazol-3-ol;
(6) 5-(4-((2-phenylpyridin-3-yl)methoxy)phenyl)isoxazol-3-ol;
(7) 5-(3-fluoro-4-((2-phenoxypyridin-3-yl)methoxy)phenyl)isoxazol-3-ol;
(8) 5-(3-fluoro-4-((2-phenoxypyridin-3-yl)methoxy)phenyl)isoxazol-3-ol;
(9) 5-(6-((2-phenoxybenzyl)oxy)pyridin-3-yl)isoxazol-3-ol;
(10) 5-(5-((2-phenoxybenzyl)oxy)pyridin-2-yl)isoxazol-3-ol;
(11) 5-(4-((2-phenoxypyridin-4-yl)methoxy)phenyl)isoxazol-3-ol;
(12) 5-(4-((2-phenoxypyridin-3-yl)methoxy)phenyl)isoxazol-3-ol;
(13) 5-(3,5-difluoro-4-((2-phenoxypyridin-3-yl)methoxy)phenyl)isoxazol-3-ol;
(14) 5-(4-((2-(4-fluorophenoxy)pyridin-3-yl)methoxy)phenyl)isoxazol-3-ol;
(15) 5-(4-((2-(isopropylthio)pyridin-3-yl)methoxy)phenyl)isoxazol-3-ol;
(16) 5-(4-((2-isopropoxybenzyl)oxy)phenyl)isoxazol-3-ol;
(17) 5-(4-((2-(pyridin-3-yloxy)benzyl)oxy)phenyl)isoxazol-3-ol;
(18) 5-(4-((3-fluoro-2-phenoxybenzyl)oxy)phenyl)isoxazol-3-ol;
(19) 5-(4-((2-fluoro-6-phenoxybenzyl)oxy)phenyl)isoxazol-3-ol;
(20) 5-(4-((2-(2,6-difluorophenoxy)pyridin-3-yl)methoxy)phenyl)isoxazol-3-ol;
(21) 5-(4-((5-fluoro-2-phenoxybenzyl)oxy)phenyl)isoxazol-3-ol;
(22) 5-(4-((3-isopropoxybenzyl)oxy)phenyl)isoxazol-3-ol;
(23) 5-(4-((3-phenoxypyridin-2-yl)methoxy)phenyl)isoxazol-3-ol;
(24) 5-(4-((2-isobutylpyridin-3-yl)methoxy)phenyl)isoxazol-3-ol;
(25) 5-(4-((3-phenoxybenzyl)oxy)phenyl)isoxazol-3-ol;
(26) 5-(3,5-difluoro-4-((2-phenoxybenzyl)oxy)phenyl)isoxazol-3-ol;
(27) 5-(4-((2-phenoxybenzyl)oxy)phenyl)isoxazol-3-ol;
(28) 5-(3-fluoro-4-((2-phenoxybenzyl)oxy)phenyl)isoxazol-3-ol;
(29) 5-(4-((2-phenoxybenzyl)oxy)benzyl)isoxazol-3-ol;
(30) 5-(4-(2-(5-methyl-2-phenyl-1,3-thiazol-4-yl)ethoxy)phenyl)isoxazol-3-ol;
(31) 5-(4-((5-phenylisoxazol-4-yl)methoxy)phenyl)isoxazol-3-ol;
(32) benzyl(3-(4-(3-hydroxyisoxazol-5-yl)phenoxy)propyl)carbamate;
(33) 5-(4-(2-(5-methyl-2-phenyl-1,3-oxazol-4-yl)ethoxy)phenyl)isoxazol-3-ol;
(34) 5-(4-(2-(3-((6-fluoropyridin-3-yl)oxy)phenyl)ethoxy)phenyl)isoxazol-3-ol;
(35) 5-(6-(2-(3-isopropoxyphenyl)ethoxy)pyridin-3-yl)isoxazol-3-ol;
(36) 5-(4-(2-(3-ethoxyphenoxy)ethyl)phenyl)isoxazol-3-ol;
(37) 5-(4-(2-(3-nitrophenyl)ethoxy)phenyl)isoxazol-3-ol;
(38) 5-(4-(2-(3-(phenoxyphenyl)ethoxy)phenyl)isoxazol-3-ol;
(39) 5-(4-(1-naphthylmethoxy)phenyl)isoxazol-3-ol;
(40) 5-(4-(2-(6-(4-fluorophenyl)pyridin-2-yl)ethoxy)phenyl)isoxazol-3-ol;
(41) 5-(4-(2-(3-isopropylamino)phenyl)ethoxy)phenyl)isoxazol-3-ol;
(42) 5-(4-(2-(3-(6-fluoropyridin-3-yl)phenyl)ethoxy)phenyl)isoxazol-3-ol;
(43) 5-(4-(2-(3-(methoxymethyl)phenyl)ethoxy)phenyl)isoxazol-3-ol;
(44) 5-(4-(2-(3-propylphenoxy)ethyl)phenyl)isoxazol-3-ol;
(45) 5-(4-((3-phenoxyphenoxy)methyl)phenyl)isoxazol-3-ol;
(46) 5-(4-(2-(2-fluoro-5-methoxyphenyl)ethoxy)phenyl)isoxazol-3-ol;
(47) 5-(4-(2-(2-isopropoxypyridin-4-yl)ethoxy)phenyl)isoxazol-3-ol;
(48) 5-(4-(2-(6-isopropoxypyridin-2-yl)ethoxy)phenyl)isoxazol-3-ol;
(49) 5-(4-(2-(3-methoxyphenyl)ethoxy)phenyl)isoxazol-3-ol;
(50) 5-(4-(2-(3-isopropoxyphenyl)ethoxy)phenyl)isoxazol-3-ol;
(51) 5-(4-(2-(4-fluoro-3-methoxyphenyl)ethoxy)phenyl)isoxazol-3-ol;
(52) 5-(4-(2-(2-phenoxypyridin-4-yl)ethoxy)phenyl)isoxazol-3-ol;
(53) 5-(4-(2-(3-(cyclohexyloxy)phenyl)ethoxy)phenyl)isoxazol-3-ol;
(54) 5-(4-(2-(2-phenoxyphenyl)ethoxy)phenyl)isoxazol-3-ol;
(55) 5-(4-(2-methoxy-2-(3-methoxyphenyl)ethoxy)phenyl)isoxazol-3-ol;
(56) 5-(4-(2-hydroxy-2-(3-methoxyphenyl)ethoxy)phenyl)isoxazol-3-ol;
(57) 5-(4-(3-phenoxypropoxy)phenyl)isoxazol-3-ol;
(58) 5-(4-(2-(3-ethoxyphenyl)ethoxy)phenyl)isoxazol-3-ol;
(59) 5-(4-(2-chloro-4-(trifluoromethyl)phenoxy)phenyl)isoxazol-3-ol;
(60) 5-(4-(2-chloro-4-(trifluoromethyl)phenoxy)-3-fluorophenoxy)isoxazol-3-ol; and
(61) 5-(4-(2-chloro-4-(trifluoromethyl)phenoxy)-3,5-difluorophenoxy)isoxazol-3-ol, and
pharmaceutically acceptable salts thereof.

* * * * *

SEQUENCE LISTING

<160> NUMBER OF SEQ ID NOS: 4

<210> SEQ ID NO 1
<211> LENGTH: 38
<212> TYPE: DNA
<213> ORGANISM: Human

<400> SEQUENCE: 1
aggatccgcc gccatgtccc ctgaatgcgc gcgggcag         38

<210> SEQ ID NO 2
<211> LENGTH: 36
<212> TYPE: DNA
<213> ORGANISM: Human

<400> SEQUENCE: 2
cgaattctta gccagaaata atcgacaagt catttc           36

<210> SEQ ID NO 3
<211> LENGTH: 39
<212> TYPE: DNA
<213> ORGANISM: Mouse

<400> SEQUENCE: 3
aggatccgcc gccatgtccc ctgagtgtgc acagacgac        39

<210> SEQ ID NO 4
<211> LENGTH: 36
<212> TYPE: DNA
<213> ORGANISM: Mouse

<400> SEQUENCE: 4
cgaattctta gctggaaata acagacaagt catttc           36